United States Patent
Pretorius et al.

(10) Patent No.: US 12,257,417 B2
(45) Date of Patent: Mar. 25, 2025

(54) DEVICES AND METHODS FOR PROVIDING A BOLUS DOSE IN A MICROFLUIDIC CIRCUIT OF A PUMP

(71) Applicant: Cequr SA, Horw (CH)

(72) Inventors: Hermanus Stephanus Pretorius, Derry, NH (US); Robert Farra, Acton, MA (US); Kenneth Barnett, Waltham, MA (US); David Piper, Leominster, MA (US); Russell Ford, Palo Alto, CA (US); Edward G. Solomon, Menlo Park, CA (US); Peter Holst, Los Altos, CA (US); Lawrence Smith, Boulder, CO (US)

(73) Assignee: CEQUR SA, Horw (CH)

( * ) Notice: Subject to any disclaimer, the term of this patent is extended or adjusted under 35 U.S.C. 154(b) by 979 days.

(21) Appl. No.: 17/231,075

(22) Filed: Apr. 15, 2021

(65) Prior Publication Data
US 2021/0228801 A1    Jul. 29, 2021

Related U.S. Application Data

(63) Continuation of application No. 16/401,178, filed on May 2, 2019, now Pat. No. 11,007,317.
(Continued)

(51) Int. Cl.
*A61M 5/168*   (2006.01)
*A61B 5/00*    (2006.01)
(Continued)

(52) U.S. Cl.
CPC ....... *A61M 5/16804* (2013.01); *A61B 5/4839* (2013.01); *A61M 5/16881* (2013.01);
(Continued)

(58) Field of Classification Search
CPC .......... A61M 5/16804; A61M 5/16881; A61M 5/1424; A61M 5/14248; A61M 5/16809;
(Continued)

(56) References Cited

U.S. PATENT DOCUMENTS

| | | |
|---|---|---|
| 5,839,467 A | 11/1998 | Saaski et al. |
| 5,845,787 A | 12/1998 | Dunnavant, Jr. |

(Continued)

FOREIGN PATENT DOCUMENTS

| | | |
|---|---|---|
| WO | 2006108775 A2 | 10/2006 |
| WO | 2007108987 A2 | 9/2007 |

OTHER PUBLICATIONS

International Search Report and Written Opinion for PCT/EP2019/061309, dated Jul. 15, 2019 (15 pages).
(Continued)

*Primary Examiner* — Nathan R Price
*Assistant Examiner* — Fatimata Sahra Diop
(74) *Attorney, Agent, or Firm* — Eversheds Sutherland (US) LLP

(57) ABSTRACT

Devices and methods for administering a medication in fluid form, the systems and methods including a basal flow path and a bolus flow path in parallel to the basal flow path. The bolus flow path includes a combined piston pump and rotatable valve. The piston pump is configured to prevent partial dosing of a bolus dose.

19 Claims, 38 Drawing Sheets

Related U.S. Application Data

(60) Provisional application No. 62/665,825, filed on May 2, 2018.

(51) Int. Cl.
*A61M 5/142* (2006.01)
*A61M 5/145* (2006.01)

(52) U.S. Cl.
CPC ....... *A61M 5/1424* (2013.01); *A61M 5/14248* (2013.01); *A61M 2005/14506* (2013.01); *A61M 5/16809* (2013.01); *A61M 5/16854* (2013.01); *A61M 2205/502* (2013.01); *A61M 2205/7545* (2013.01)

(58) Field of Classification Search
CPC .... A61M 5/16854; A61M 2005/14506; A61M 2205/502; A61M 2205/7545; A61B 5/4839; F01C 1/104
See application file for complete search history.

(56) References Cited

U.S. PATENT DOCUMENTS

| | | |
|---|---|---|
| 6,619,311 B2 | 9/2003 | O'Connor et al. |
| 6,644,944 B2 | 11/2003 | Karp |
| 6,845,968 B2 | 1/2005 | Killeen et al. |
| 6,878,271 B2 | 4/2005 | Gilbert et al. |
| 6,890,093 B2 | 5/2005 | Karp et al. |
| 7,431,052 B2 | 10/2008 | Gravesen et al. |
| 7,517,335 B2 | 4/2009 | Gravesen et al. |
| 7,520,295 B2 | 4/2009 | Rasmussen et al. |
| 7,603,898 B2 | 10/2009 | Speldrich |
| 7,632,247 B2 | 12/2009 | Adams |
| 7,713,258 B2 | 5/2010 | Adams et al. |
| 7,713,262 B2 | 5/2010 | Adams et al. |
| 7,771,391 B2 | 6/2010 | Carter |
| 7,815,609 B2 | 10/2010 | Hines et al. |
| 7,846,132 B2 | 12/2010 | Gravesen et al. |
| 7,887,756 B2 | 2/2011 | McAvoy et al. |
| 7,927,306 B2 | 4/2011 | Cross et al. |
| 7,931,621 B2 | 4/2011 | Cross et al. |
| 7,938,801 B2 | 5/2011 | Hawkins et al. |
| 7,976,493 B2 | 7/2011 | Carter et al. |
| 7,976,500 B2 | 7/2011 | Adams et al. |
| 7,976,505 B2 | 7/2011 | Hines et al. |
| 8,062,256 B2 | 11/2011 | Carter et al. |
| 8,109,912 B2 | 2/2012 | Alferness et al. |
| 8,114,064 B2 | 2/2012 | Alferness et al. |
| 8,128,596 B2 | 3/2012 | Carter |
| 8,128,597 B2 | 3/2012 | Cross et al. |
| 8,162,923 B2 | 4/2012 | Adams et al. |
| 8,226,606 B2 | 7/2012 | Adams et al. |
| 8,226,607 B2 | 7/2012 | Carter et al. |
| 8,230,744 B2 | 7/2012 | Gravesen et al. |
| 8,231,572 B2 | 7/2012 | Carter et al. |
| 8,231,577 B2 | 7/2012 | Carter et al. |
| 8,246,581 B2 | 8/2012 | Adams et al. |
| 8,361,030 B2 | 1/2013 | Carter |
| 8,409,151 B2 | 4/2013 | Hawkins et al. |
| 8,449,504 B2 | 5/2013 | Carter et al. |
| 8,540,673 B2 | 9/2013 | Hines et al. |
| 8,547,239 B2 | 10/2013 | Peatfield et al. |
| 8,613,719 B2 | 12/2013 | Karratt et al. |
| 8,672,873 B2 | 3/2014 | Gravesen et al. |
| 8,679,694 B2 | 3/2014 | Zimmermann et al. |
| 8,696,630 B2 | 4/2014 | Carter et al. |
| 8,753,315 B2 | 6/2014 | Alferness et al. |
| 8,758,308 B2 | 6/2014 | Alferness et al. |
| 8,894,612 B2 | 11/2014 | Hawkins et al. |
| 8,905,974 B2 | 12/2014 | Carter et al. |
| 8,945,064 B2 | 2/2015 | Gravesen et al. |
| 9,005,189 B2 | 4/2015 | Gravesen et al. |
| 9,022,972 B2 | 5/2015 | Gravesen et al. |
| 9,039,654 B2 | 5/2015 | Gravesen et al. |
| 9,174,009 B2 | 11/2015 | Peatfield et al. |
| 9,211,378 B2 | 12/2015 | Boit et al. |
| 9,387,288 B2 | 7/2016 | Karratt et al. |
| 9,651,039 B2 | 5/2017 | Mathies et al. |
| 9,694,147 B2 | 7/2017 | Peatfield et al. |
| 9,713,674 B2 | 7/2017 | Carter et al. |
| 9,867,929 B2 | 1/2018 | Searle et al. |
| 9,968,747 B2 | 5/2018 | Gravesen et al. |
| 10,226,588 B2 | 3/2019 | Peatfield et al. |
| 10,258,741 B2 | 4/2019 | Gravesen et al. |
| 2009/0088689 A1 | 4/2009 | Carter |
| 2011/0319861 A1 | 12/2011 | Wilk |
| 2012/0101451 A1* | 4/2012 | Boit .................... A61M 39/223 417/490 |
| 2014/0052096 A1* | 2/2014 | Searle ................. A61M 5/1452 604/67 |
| 2014/0180210 A1* | 6/2014 | Niklaus ................... F04B 53/14 604/152 |
| 2014/0311912 A1 | 10/2014 | Shih et al. |
| 2015/0367066 A1 | 2/2015 | Gravesen et al. |
| 2016/0008536 A1 | 1/2016 | Gravesen et al. |
| 2016/0038940 A1 | 1/2016 | Babcock |
| 2017/0191892 A1 | 7/2017 | Winzeler et al. |
| 2018/0200412 A1 | 7/2018 | Dang et al. |
| 2018/0240236 A1 | 8/2018 | Bazargan et al. |

OTHER PUBLICATIONS

Written Opinion of the International Preliminary Examining Authority for PCT/EP2019/061309, dated Mar. 18, 2020 (7 pages).
International Preliminary Report on Patentability for PCT/EP2019/061309, dated Aug. 4, 2020 (16 pages).

* cited by examiner

DEVICES AND METHODS FOR PROVIDING A BOLUS DOSE IN A MICROFLUIDIC CIRCUIT OF A PUMP

CROSS-REFERENCE TO RELATED APPLICATIONS

This application claims priority to, the benefit of, and is a continuation application of U.S. patent application Ser. No. 16/401,178, file May 2, 2019, which claims priority to and the benefit of U.S. Provisional Patent Application No. 62/665,825, filed May 2, 2018, which are both hereby incorporated by reference herein in their entireties.

FIELD OF THE DISCLOSURE

The disclosure generally relates to bolus dosing of a medicament and more particularly relates to systems and methods for providing a bolus dose in a microfluidic circuit of a pump device, such as a wearable patch pump.

BACKGROUND

Insulin pumps may provide a user with constant basal delivery and bolus dosing of medicament (e.g., insulin). Bolus dosing can be activated by the user at any time, but is typically initiated during mealtime. Current bolus dosing systems and methods may have performance, user interface, and manufacturing issues. For example, the valves of a bolus delivery system may become stuck or leak, doses may not be delivered, or the delivered dose may be incorrect (e.g., partial dosing, which is undesirable, or the bolus delivery system may have difficulty accurately delivering microliter doses). Moreover, current systems may fail to reset, preventing the administration of future bolus doses.

Furthermore, for most if not all drugs (e.g., insulin) the bolus delivery system should not have a failure mode in which the reservoir contents may flow directly into the patient. In addition, material selection for pump components may be a concern in need of addressing. For example, the wetted materials of construction of the pump need to be suitably compatible with the medicament.

BRIEF SUMMARY

Devices and methods for administering a medication in fluid form are provided. In one aspect, the device includes a basal flow path; and a bolus flow path in parallel to the basal flow path, wherein the bolus flow path comprises an inlet check valve, a first outlet check valve downstream of the inlet check valve, and a piston pump disposed between the inlet check valve and the first outlet check valve, wherein the piston pump is configured to prevent partial dosing of a bolus dose. In some embodiments, the piston pump comprises: a button comprising a resilient arm attached to a protrusion; a piston in mechanical communication with the protrusion, wherein the piston comprises a first channel having a dispensing lip and a second channel having a filling lip, wherein the protrusion is configured to move between the first channel and the second channel to engage the fill lip or the dispense lip; and a track configured to move the protrusion between the first channel and the second channel. In some embodiments, the piston pump includes a bolus chamber comprising an inlet and an outlet; the piston is at least partially disposed within the bolus chamber, wherein the piston comprises a first position and a second position; and a spring is disposed about the button, wherein the spring is configured to bias the button in an extended position, which corresponds to the first position of the piston. The device may further include a fill port disposed upstream of the basal flow path and the bolus flow path; a filter disposed upstream of the basal flow path and the bolus flow path; and a cannula disposed downstream of the basal flow path and the bolus flow path. In some embodiments, the device is part of a wearable patch pump for administering insulin to a patient.

In another aspect, a method for pumping a bolus dose of a fluid in a microfluidic circuit is provided. In some embodiments, the method includes: (i) depressing a button to move a piston disposed at least partially within a bolus chamber from a first position to a second position; (ii) filling the bolus chamber with the bolus dose when a protrusion attached to a resilient arm of the button reaches a distal end of a track, which corresponds to the second position of the piston; and (iii) releasing the button to move the piston disposed at least partially within the bolus chamber from the second position to the first position to increase a pressure within the bolus chamber to deliver the bolus dose. The method may further include preventing partial dosing of the bolus dose by preventing filling the bolus chamber with the bolus dosage until the piston is moved to the second position. In some embodiments, the method includes (a) flexing, by the track when the button is depressed, the resilient arm towards the second channel; (b) moving, by the resilient arm when the protrusion reaches a distal end of the track, the protrusion towards the first channel; and (c) moving, by the resilient arm when the protrusion reaches a proximal end of the track, the protrusion towards the second channel. In some embodiments, the inlet of the bolus chamber does not align with a fluidic inlet for filling the bolus chamber with the bolus dose until the protrusion reaches the distal end of the track, at which point the protrusion is directed against the dispense lip, wherein the protrusion pushes the piston via the spring in order to dispense a bolus dose. In some embodiments, the delivered bolus dose has a volume variation that is within ±10% of a targeted bolus dose volume.

In still another aspect, the device for administering a bolus dose includes: a bolus flow path; and a piston pump disposed along the bolus flow path and configured to prevent partial dosing of a bolus dose, wherein the piston pump comprises a button comprising a resilient arm attached to a protrusion, a piston in mechanical communication with the protrusion, wherein the piston comprises a first channel having a dispensing lip and a second channel having a filling lip, wherein the protrusion is configured to move between the first channel and the second channel to engage the fill lip or the dispense lip, and a track configured to move the protrusion between the first channel and the second channel. The piston pump may include a bolus chamber comprising an inlet and an outlet, the piston may be at least partially disposed within the bolus chamber, wherein the piston comprises a first position and a second position, and a spring may be disposed about the button, wherein the spring is configured to bias the button in an extended position, which corresponds to the first position of the piston.

In some methods for operating this device, the method includes: depressing the button from the extended position to move the piston from the first position to the second position and thereby fill the bolus chamber with the bolus dose via the inlet; and then releasing the button to permit the spring to bias the button back to the extended position and thereby move the piston to the first position and allow the bolus dose to flow from the bolus chamber via the outlet to a cannula. In some embodiments, the bolus dose has a volume variation that is within ±10% of a targeted bolus dose volume.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Improved devices, systems, and methods have been developed for providing a bolus dose in a microfluidic circuit of a drug delivery device, such as an insulin pump. In embodiments, the drug delivery device is in the form of a wearable patch pump, which a patient (i.e., a user) can adhere to his or her skin for self-administering medication over a number of days. The bolus dose is in a liquid form, e.g., a pure liquid, a solution, or possibly a suspension. The term "fluid" as used herein generally refers to liquids, i.e., incompressible fluids.

The improved designs disclosed herein may advantageously provide more reliable and accurate dosing compared to conventional bolus pumps in patch pump systems. For example, in some embodiments, the bolus dose delivery system includes one or more push buttons that provide a bolus dose of about 20 µl of insulin or the like within a targeted +/−10% bolus dose volume variation margin (and ideally within +/−5%). The frequency of doses can be as fast as 2 Hz. In some instances, the bolus dose delivery system can be operated up to 200 times over a 3-day period, with 100 times being typical. The volume of the delivered dose is independent of the force or speed that the button is actuated. Ideally, the button stroke is no more than 7 mm, with a maximum force of 25 N, and priming is not required. However, if necessary, priming the bolus dose delivery systems may require no more than 3 button strokes. The design of the button inhibits unintentional dosing and provides feedback when a dose is administered. The bolus dose delivery system will not deliver a partial dose. In addition, the bolus dose delivery system is configured for fail-safe operation, in that the system does not include a bypass or short circuit from the reservoir to the delivery outlet, e.g., the cannula. The various components of the bolus dose delivery system are shock and vibration resistant, as well as temperature and humidity resistant for transportation purposes.

Illustrative Embodiments

Figure 1:
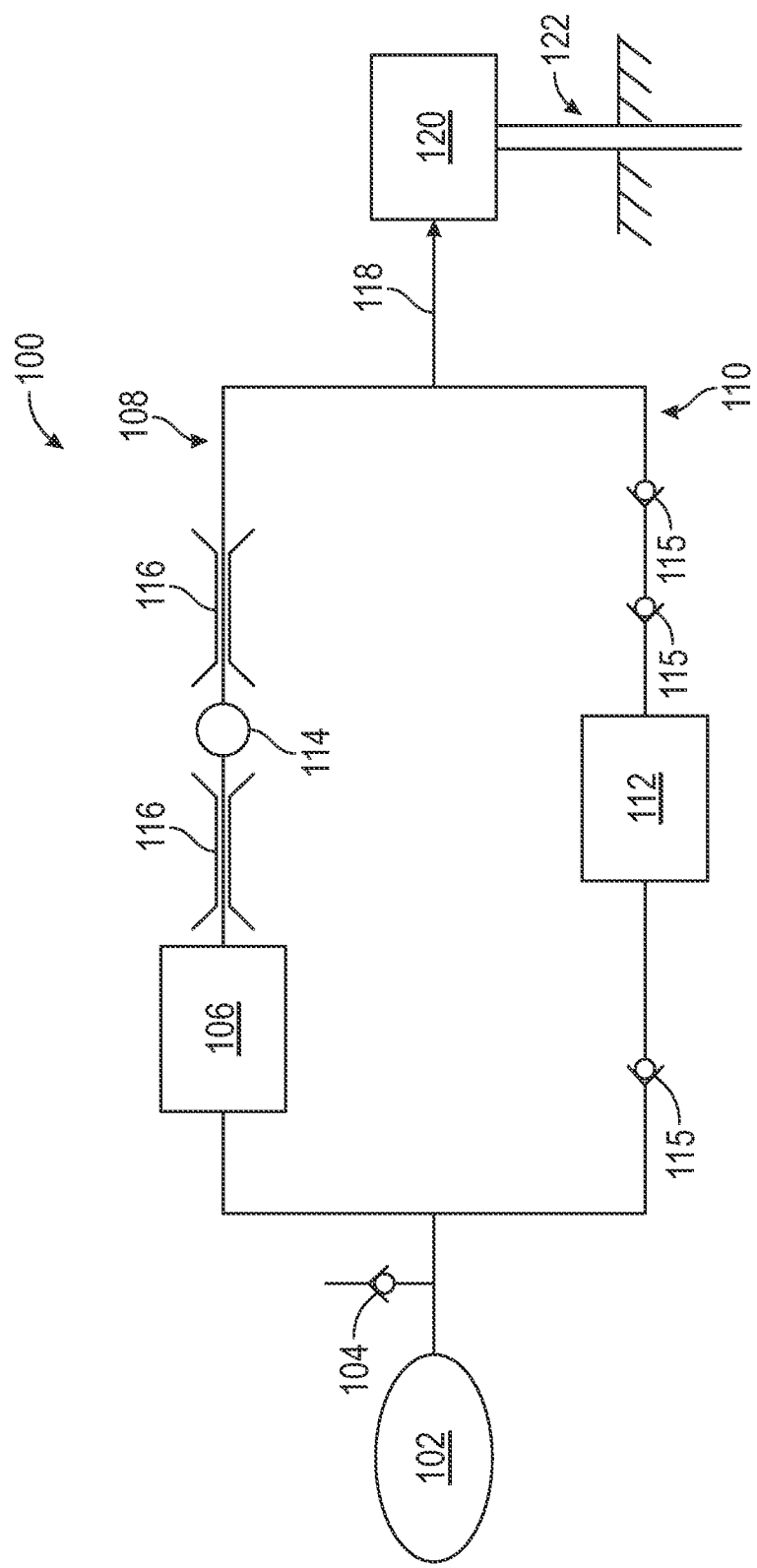
FIG. 1 depicts a microfluidic circuit of a fluid medicament delivery device in accordance with one or more embodiments of the disclosure.

FIG. 1 depicts a microfluidic circuit 100 of a fluid drug delivery device (e.g., an insulin pump or the like). In certain embodiments, the microfluidic circuit 100 includes a reservoir 102 configured to hold a quantity of a liquid drug formulation. The reservoir 102 may be filled with any suitable fluid. In some embodiments, the fluid comprises a drug, such as insulin. In some embodiments, the reservoir 102 comprises an elastomeric bladder. A fill port 104 is used to introduce the drug formulation into the microfluidic circuit 100. Introducing the drug formulation via the fill port 104 fills the reservoir 102.

During use, the insulin (or other drug) is forced from the reservoir 102, due to contraction of the elastomeric bladder, into two parallel flow paths. The first flow path is a basal flow path 108, and the second flow path is a bolus flow path 110. In certain embodiments, a filter 106 is disposed along the basal flow path 108. In other instances, the filter 106 is configured to filter fluid in both the basal flow path 108 and the bolus flow path 110. For example, the filter 106 is located upstream of both the basal flow path 108 and the bolus flow path 110.

The basal flow path 108 delivers a constant dose of insulin to a user. The bolus flow path 110, on the other hand, delivers a bolus dose of insulin to the user (e.g., a human patient) as needed or desired by the user upon actuation of a bolus delivery system 112 via a bolus button or the like. Any number of systems and methods may be used to deliver the bolus dose via the bolus flow path 110. In some embodiments, the basal flow path 108 may be omitted.

The basal flow path 108 includes a pressure sensor 114 or other flow sensor in communication with the basal flow path 108. Two flow restrictors 116 are disposed along the basal flow path 108. In other embodiments, one or more than two flow restrictors may be included in the basal flow path. In some embodiments, one or more flow restrictors may be included in the bolus flow path 110. In some instances, a flow restrictor 116 is omitted from the bolus flow path 110, and the filter 106 is disposed along the basal flow path 108. The flow restrictors 116 may be configured to limit the rate of fluid flow through the basal flow path 108 and/or the bolus flow path 110. In certain embodiments, the flow restrictors 116 are in the form of capillary tubes or the like. In some instances, the basal flow path 108 includes two flow restrictors 116 in series. In such instances, the pressure sensor 114 is disposed between the flow restrictors 116 along the basal flow path 108. Additional flow restrictors 116 may be disposed along the basal flow path 108. In some instances, the flow restrictors 116 may be omitted from the basal flow path 108.

In certain embodiments, the bolus flow path 110 includes a flow restrictor disposed upstream of the bolus delivery system 112 along the bolus flow path 110. In such instances, the filter 106 may be disposed upstream of the bolus flow path 110 to filter the fluid before it enters the flow restrictor. Additional flow restrictors 116 may be disposed along the bolus flow path 110 upstream and/or downstream of the bolus delivery system 112. In some instances, the flow restrictors 116 may be omitted along the bolus flow path 110.

As used herein for all embodiments, the term "flow restrictor" refers to a component structured to throttle, or limit, a flow of fluid through a microfluidic circuit. It is neither a valve nor operable to shut off the flow of fluid. In some embodiments, the flow restrictor includes one or more channels having passages reduced in size relative to other passages in the microfluidic circuit, such that the dimensions (cross-sectional area and length) are selected to provide a limit on the rate of flow of fluid therethrough for a given range of fluid pressures on the supply side of the restrictor. These flow restrictors may include (i) a microcapillary, such as one produced by drawing or extruding glass tubes, and/or (ii) a microfabricated flow channel—which may be referred to herein as micro-electromechanical system (MEMS)-type flow restrictors—produced using MEMS fabrication techniques and materials, and it therefore may be referred to herein as a "MEMS flow restrictor." The presently disclosed flow restrictor also may be produced using other suitable manufacturing techniques known in the art, such as additive manufacturing (e.g., 3D-printing) methods and systems.

The basal flow path 108 and/or the bolus flow path 110 also include one or more check valves 115 disposed thereon. In some instances, at least one check valve 115 is disposed along the bolus flow path 110 upstream and downstream of the bolus delivery system 112. In the illustrated embodiment, one check valve 115 is disposed upstream of the bolus delivery system 112 along the bolus flow path 110, and two check valves 115 are disposed downstream of the bolus delivery system 112 along the bolus flow path 110. The pressure required to open the check valve 115 downstream of the bolus delivery system 112 along the bolus flow path 110 may be greater than the pressure of the reservoir 102. In some embodiments, the check valves 115 may be omitted. In some embodiments, the check valves 115 may be replaced with one or more multi-position valve(s).

The parallel basal flow path 108 and the bolus flow path 110 join at a common channel 118, upstream of a cannula 120. The cannula 120 extends into/through the skin 122 of the user, thus delivering the insulin (or other drug) subcutaneously.

The microfluidic circuit 100 may include additional components. Conversely, certain components may be omitted. In any case, the microfluidic circuit 100 is configured to deliver one or more drugs in fluid form. The devices and systems described herein can be used to deliver essentially any suitable drug for therapeutic, prophylactic, or palliative purposes.

Figure 2:
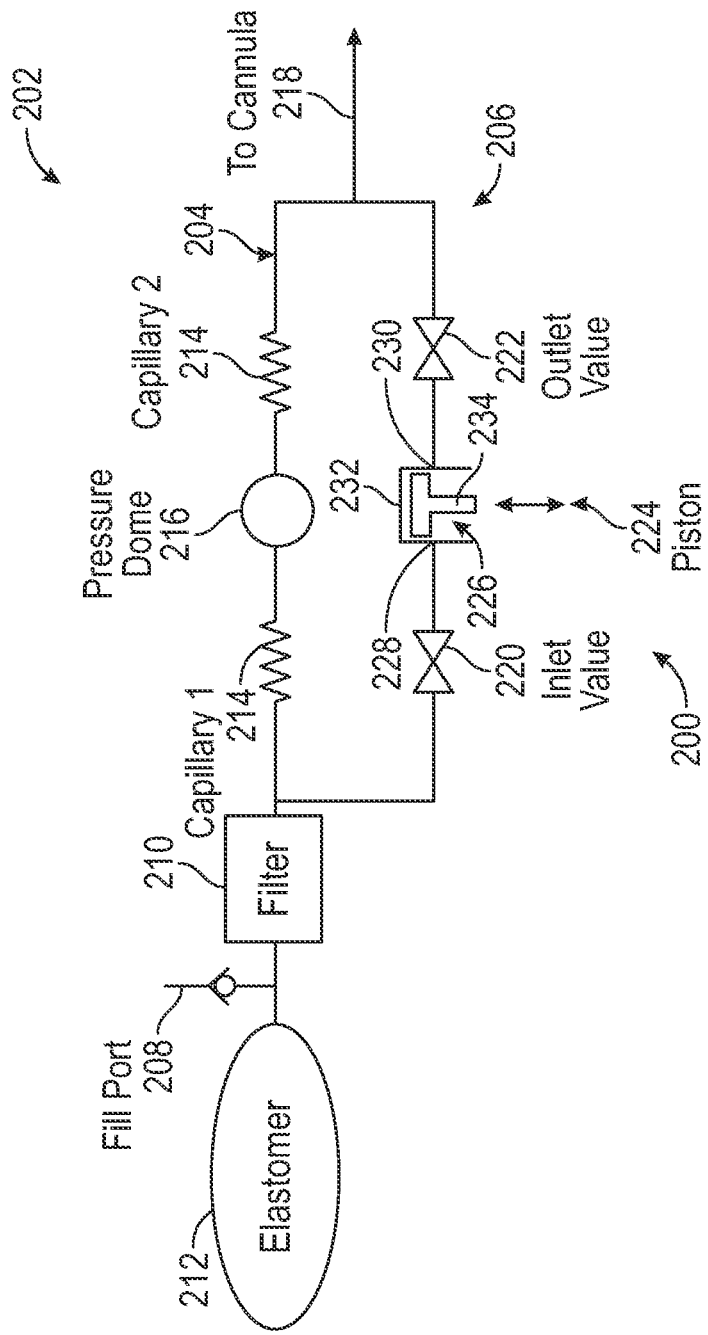
FIG. 2 depicts a microfluidic circuit of a fluid medicament delivery device in accordance with one or more embodiments of the disclosure.

FIG. 2 depicts one embodiment of a bolus dose delivery system 200 incorporated into a microfluidic circuit 202 of a fluid medicament delivery device (e.g., an insulin pump or the like) configured to administer a medication in fluid form. In other instances, the bolus dose delivery system 200 may be incorporated into the microfluidic circuit 100. The bolus dose delivery system 200 may be incorporated into any suitable medicament delivery device.

The microfluidic circuit 202 includes a basal flow path 204 and a bolus flow path 206 in parallel to each other. A fill port 208 is disposed upstream of the basal flow path 204 and the bolus flow path 206 between a filter 210 and a reservoir 212. The filter 210 may be any suitable size, shape, or configuration. The fill port 208 may be positioned at any suitable location within the microfluidic circuit 202. In some instances, the reservoir 212 comprises an elastomeric bladder. The fill port 208 may include a check valve and is used to introduce insulin (or other drug) into the microfluidic circuit 202. Introducing insulin via the fill port 208 fills, among other things, the reservoir 212. The basal flow path 204 includes two flow restrictors 214 in series, with at least one pressure sensor 216 disposed between the two flow restrictors 214. A cannula 218 is disposed downstream of the basal flow path 204 and the bolus flow path 206. The cannula 218 extends into/through the skin of the user, thus delivering the insulin subcutaneously. The microfluidic circuit 202 may include additional components. Conversely, certain components may be omitted. In any case, the microfluidic circuit 202 may be configured to deliver one or more medicaments or combinations thereof in fluid form.

The bolus dose delivery system 200 is disposed along the bolus flow path 206. Generally speaking, the bolus dose delivery system 200 includes a first valve 220, a second valve 222 downstream of the first valve 220, and a piston pump 224 disposed between the first valve 220 and the second valve 222.

As depicted in FIGS. 2 and 6-8, the piston pump 224 includes a bolus chamber 226. The bolus chamber 226 comprises an inlet 228 and an outlet 230. In this manner, the first valve 220 controls fluid flow into the inlet 228 of the bolus chamber 226, and the second valve 222 controls fluid flow out of the outlet 230 of the bolus chamber 226. The bolus chamber 226 is formed within an enclosure 232 or the like. In some instances, the bolus chamber 226 accommodates 20 µl of fluid. The bolus chamber 226 may be any suitable size, shape, or configuration. In certain embodiments, the size (i.e., the internal volume) of the bolus chamber 226 corresponds to the bolus dose.

The bolus dose delivery system 200 also includes a piston 234 at least partially disposed within the bolus chamber 226.

The piston 234 may be any suitable size, shape, or configuration. The piston 234 is moveable between a first position and a second position. For example, the piston 234 moves (or slides, translates) within the bolus chamber 226 between the first position and the second position. To prevent leaks, the piston 234 includes one or more seals 236 (e.g., O-rings or the like) disposed thereabout. The seals 236 form a seal between the piston 234 and the bolus chamber 226. In this manner, the seals 236 prevent leaks from the bolus chamber 226 as the piston 234 moves between the first position and the second position.

In addition, the bolus dose delivery system 200 includes a latch 238. The latch 238 may be any suitable size, shape, or configuration. The latch 238 comprises a latched position configured to secure the piston 234 in the second position (as depicted in FIG. 8) and an unlatched position configured to release the piston 234 to the first position.

In order to actuate the bolus dose delivery system 200, the piston pump 224 comprises a button 240 that is moveable. The button 240 is configured to, among other things, open the first valve 220 and close the second valve 222, or vice versa. In addition, the button 240 is configured to move the latch 238 between the latched position and the unlatched position. For example, the button 240 includes a first cam 242, a second cam 244, and a third cam 246. The first cam 242 is in mechanical communication with the first valve 220 and the second valve 222. In one embodiment, the first cam 242 comprises a surface 245 of the button 240 with one or more cam profiles 247 (or surfaces). As a result, movement of the button 240 (e.g., depressing or axially displacing) causes the first cam 242 to open the first valve 220 and close the second valve 222, or vice versa.

Figure 3:
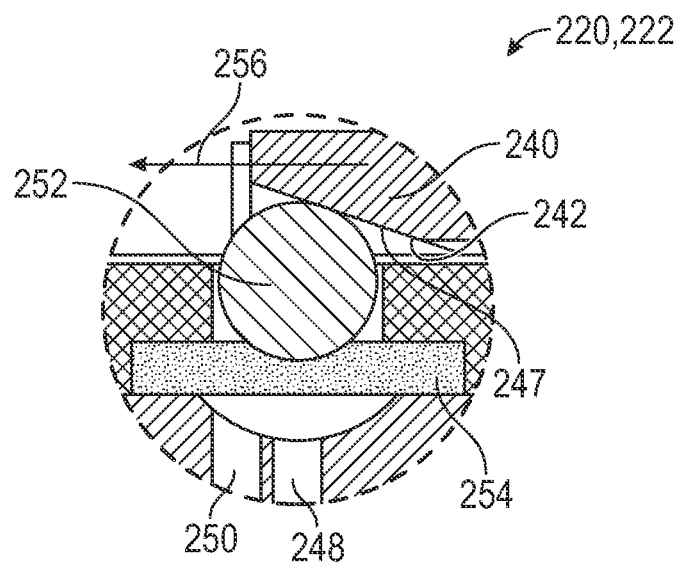
FIGS. 3-5 depict a valve in accordance with one or more embodiments of the disclosure.
Figure 4:
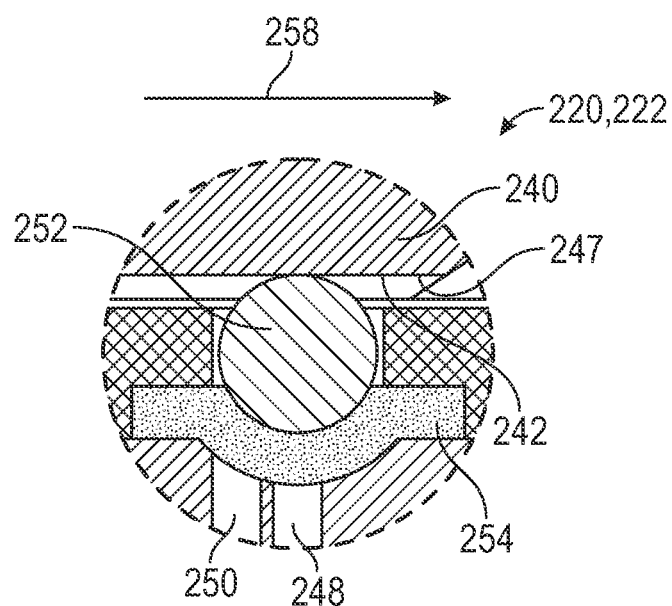
Figure 5:
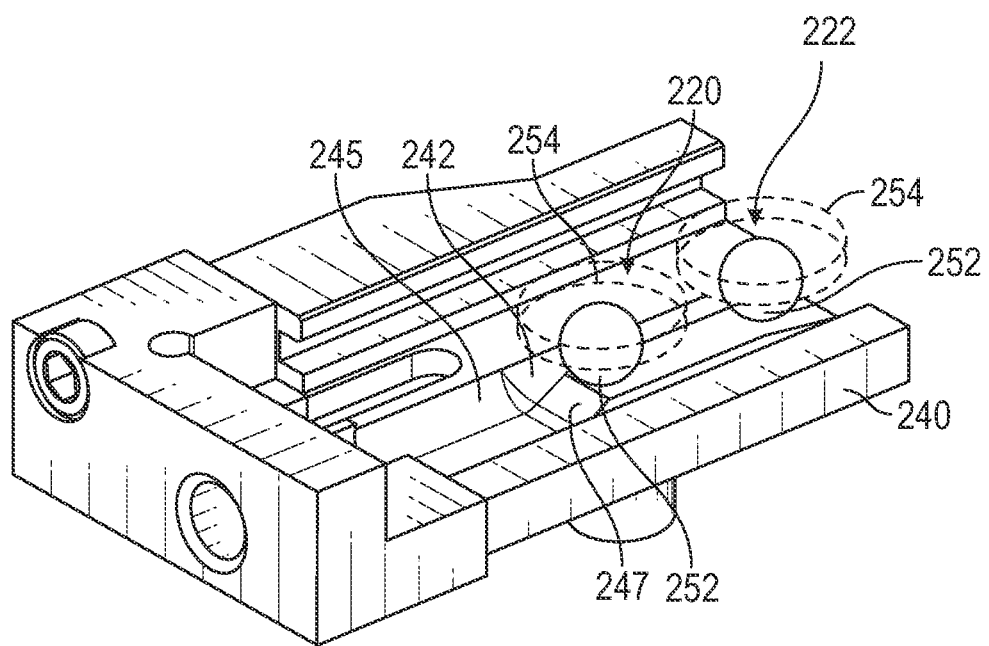

As depicted in FIGS. 3-5, to facilitate opening and closing via the first cam 242, the first valve 220 and the second valve 222 each comprise an inlet 248, an outlet 250, a ball 252, and a diaphragm 254. The ball 252 is moveably disposed between the first cam 242 of the button 240 and the diaphragm 254. The diaphragm 254 is located between the ball 252 and the inlet 248 and the outlet 250. In this manner, movement of the first cam 242 in a first direction 256 causes the first cam 242 to engage the ball 252, which presses the ball 252 against the diaphragm 254 to close the inlet 248 and the outlet 250 of the first valve 220 or the second valve 222. That is, the force of the ball 252 against the diaphragm 254 causes the diaphragm 254 to press against the inlet 248 and the outlet 250 to form a seal thereabout. Conversely, movement of the first cam 242 in a second direction 258 opposite the first direction 256 causes the first cam 242 to disengage the ball 252, which releases the diaphragm 254 back to its repose position, thereby allowing fluid flow between the inlet 248 and the outlet 250. Any valve described in relation to any embodiment disclosed herein may incorporate a similar structure as the first valve 220 and the second valve 222.

Figure 6:
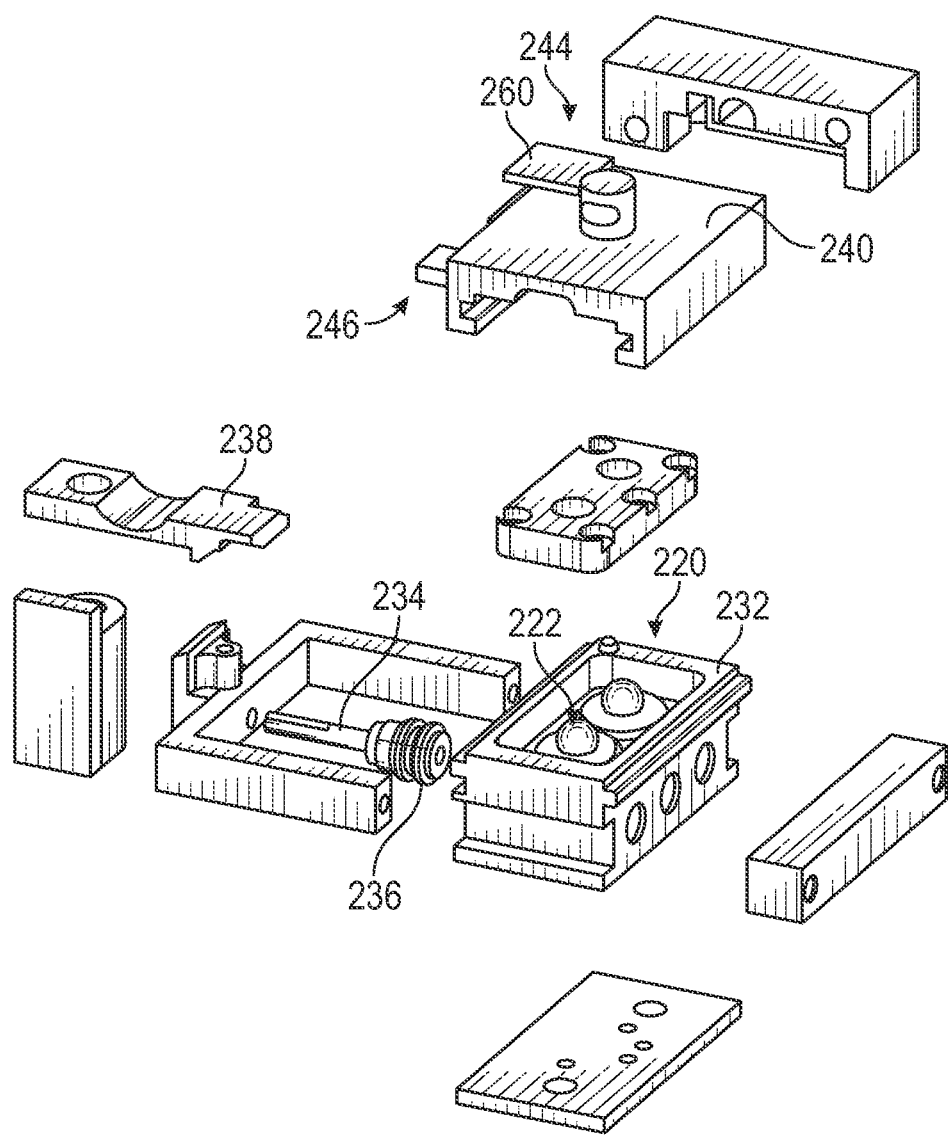
FIGS. 6-8 depict a bolus dose delivery system in accordance with one or more embodiments of the disclosure.
Figure 7:
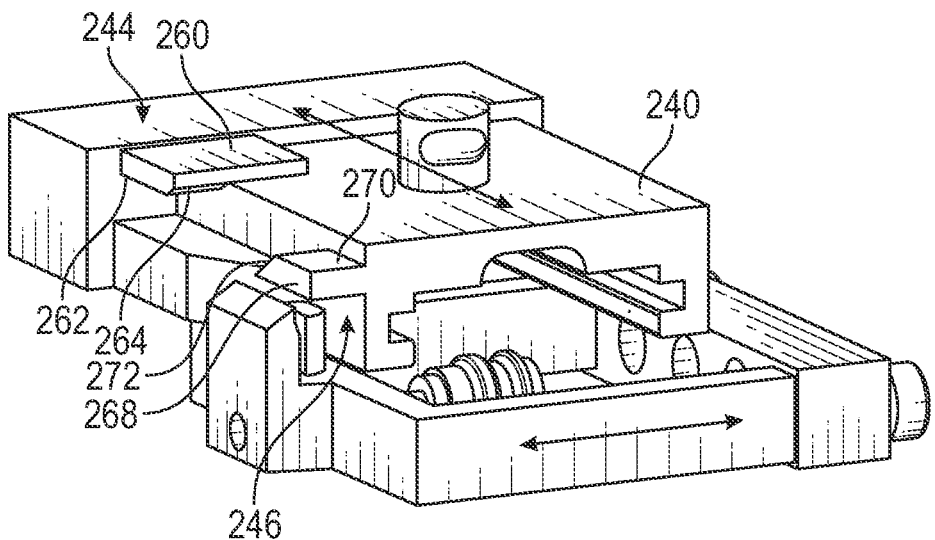
Figure 8:
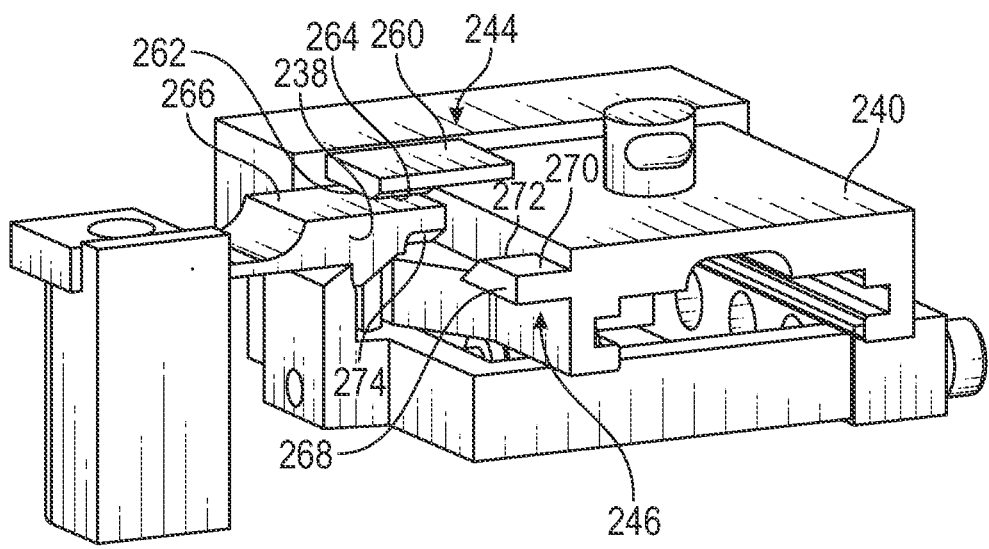
Figure 9A:
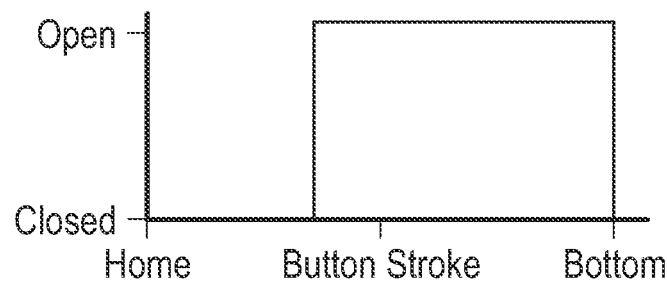
FIGS. 9A-9C depict a sequence in accordance with one or more embodiments of the disclosure.
Figure 9B:
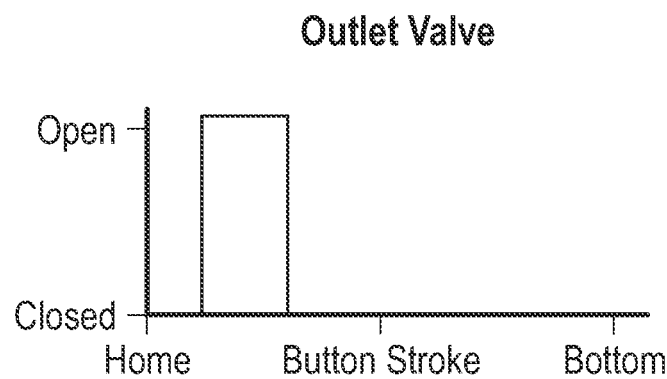
Figure 9C:
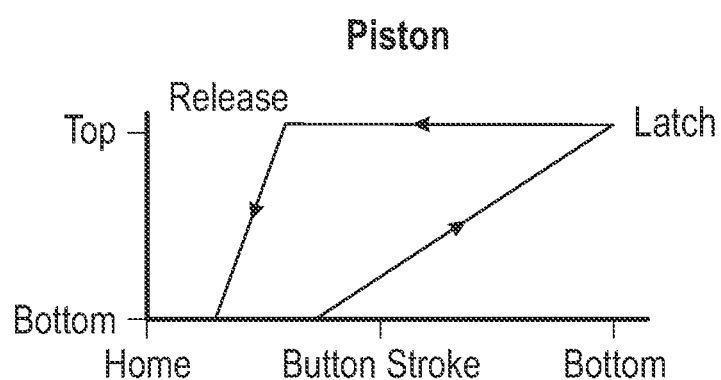

As depicted in FIGS. 6-8, in some instances, the second cam 244 is in mechanical communication with the latch 238. For example, the second cam 244 may contact the latch 238 or a portion thereof. In one embodiment, the second cam 244 comprises a protrusion 260 having a surface 262 with a cam profile 264. As a result, movement of the button 240 causes the second cam 244 to engage and move the latch 238 to the latched position. For example, the cam profile 264 engages a backside 266 of the latch 238. Similarly, in some instances, the third cam 246 is in mechanical communication with the latch 238. In some embodiments, the third cam 246 comprises a protrusion 268 having a surface 270 with a cam profile 272 opposite the second cam 244. As a result, movement of the button 240 in the opposite direction causes the third cam 246 to engage and move the latch 238 to the unlatched position, while the second cam 244 disengages the latch 238. For example, the cam profile 272 engages a front side 274 of the latch 238. The first cam 242, the second cam 244, and the third cam 246 may be any suitable cam device. For example, the first cam 242, the second cam 244, and the third cam 246 may be linear cams or the like. FIGS. 9A-9C depict the sequence of the opening and closing of the first valve 220 and the second valve 222, as well as the movement of the piston 234 between the first position and the second position after being latched and unlatched to the latch 238 due to the movement of the button 240.

In use, a user can deliver a bolus dose from the microfluidic circuit 202 by actuating the button 240. For example, actuation of the button 240 opens the first valve 220 and closes the second valve 222. In this valve configuration, the piston 234 is in the second and latched position via the second cam 244 and the latch 238 to enable fluid from the reservoir 212 to fill the bolus chamber 226. The fluid within the bolus chamber 226 constitutes the bolus dose. Next, the first valve 220 is closed and the second valve 222 is opened via movement of the button 240 in the opposite direction. At the same time (or very close thereto), the piston 234 is released from the latch position via the third cam 246. As a result, the piston 234 moves to the second position, which permits or enables transfer/flow of the bolus dose from the bolus chamber 226 to the cannula 218. This process may be repeated as needed to deliver bolus doses to the user.

Figure 23:
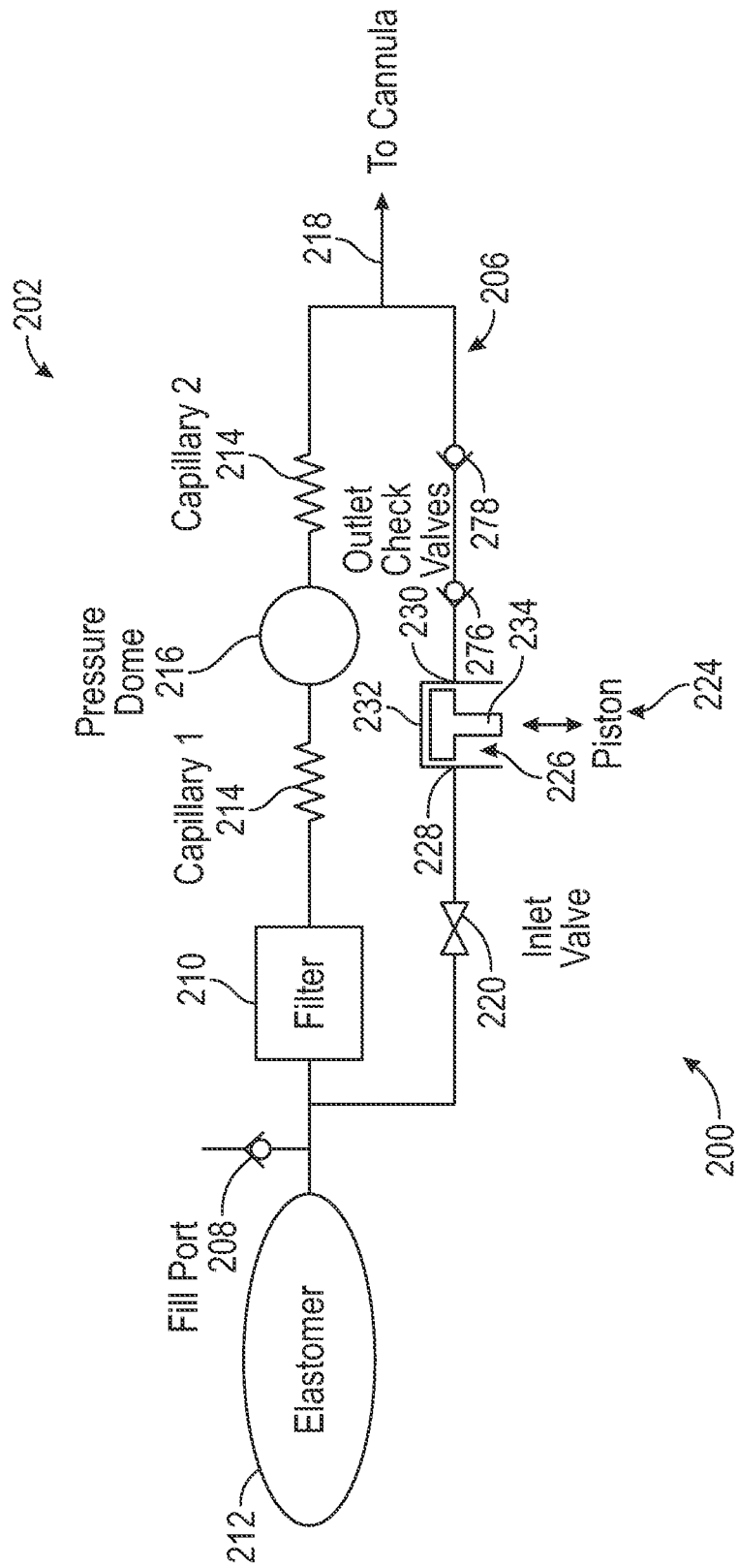
FIG. 23 depicts a microfluidic circuit of a fluid medicament delivery device in accordance with one or more embodiments of the disclosure.

In an alternate embodiment, the second valve 222 may be omitted. In such instances, as depicted in FIG. 23, a first outlet check valve 276 and a second outlet check valve 278 are disposed downstream of the piston pump 224 in series along the bolus flow path 206. The operation of the bolus dose delivery system 200 may be essential the same as described above, except that as the piston 234 moves to the second position, the pressure within the bolus chamber 226 is increased above the cracking pressure of the outlet check valves 276, 278, which causes the outlet check valves 276, 278 to open instead of the button 240. In some instances, a first outlet check valve 276 and a second outlet check valve 278 comprise PD valves. The first outlet check valve 276 and the second outlet check valve 278 may be any suitable check valve or the like.

Figure 10:
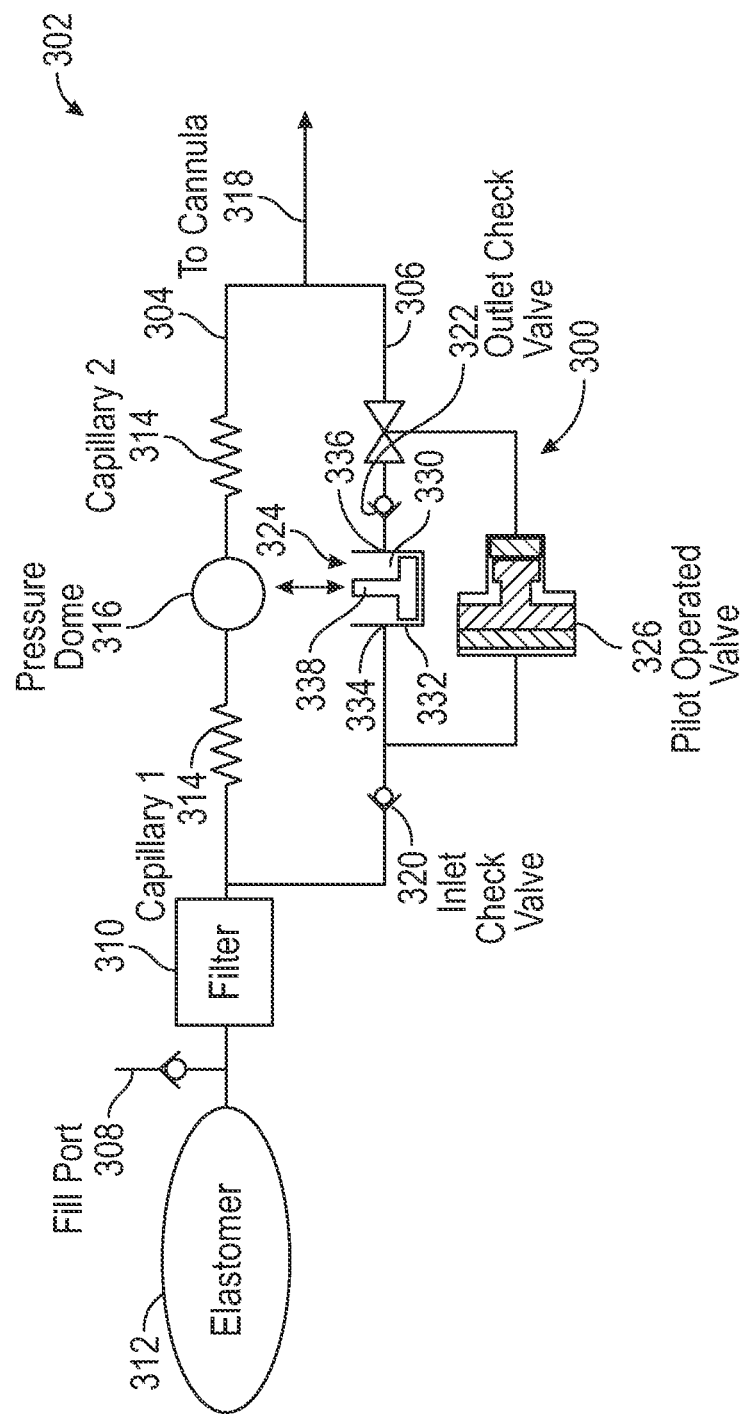
FIG. 10 depicts a microfluidic circuit of a fluid medicament delivery device in accordance with one or more embodiments of the disclosure.

FIG. 10 depicts one example of a bolus dose delivery system 300 incorporated into a microfluidic circuit 302 of a fluid medicament delivery device (e.g., an insulin pump or the like) configured to administer a medication in fluid form. In other instances, the bolus dose delivery system 300 may be incorporated into the microfluidic circuit 100. The bolus dose delivery system 300 may be incorporated into any suitable medicament delivery device.

The microfluidic circuit 302 includes a basal flow path 304 and a bolus flow path 306 in parallel to each other. A fill port 308 is disposed upstream of the basal flow path 304 and the bolus flow path 306 between a filter 310 and a reservoir 312. The filter 310 may be any suitable size, shape, or configuration. The fill port 308 may be positioned at any suitable location within the microfluidic circuit 302. In some instances, the reservoir 312 comprises an elastomeric bladder. The fill port 308 may include a check valve and is used to introduce insulin (or other medication) to the microfluidic circuit 302. Introducing insulin via the fill port 308 fills, among other things, the reservoir 312. The basal flow path 304 includes two flow restrictors 314 in series, with at least one pressure sensor 316 disposed between the two flow restrictors 314. A cannula 318 is disposed downstream of the basal flow path 304 and the bolus flow path 306. The cannula 318 extends into/through the skin of the user, thus delivering the insulin subcutaneously. The microfluidic circuit 302 may include additional components. Conversely, certain components may be omitted. In any case, the microfluidic circuit 302 may be configured to deliver one or more medicaments or combinations thereof in fluid form.

Figure 11:
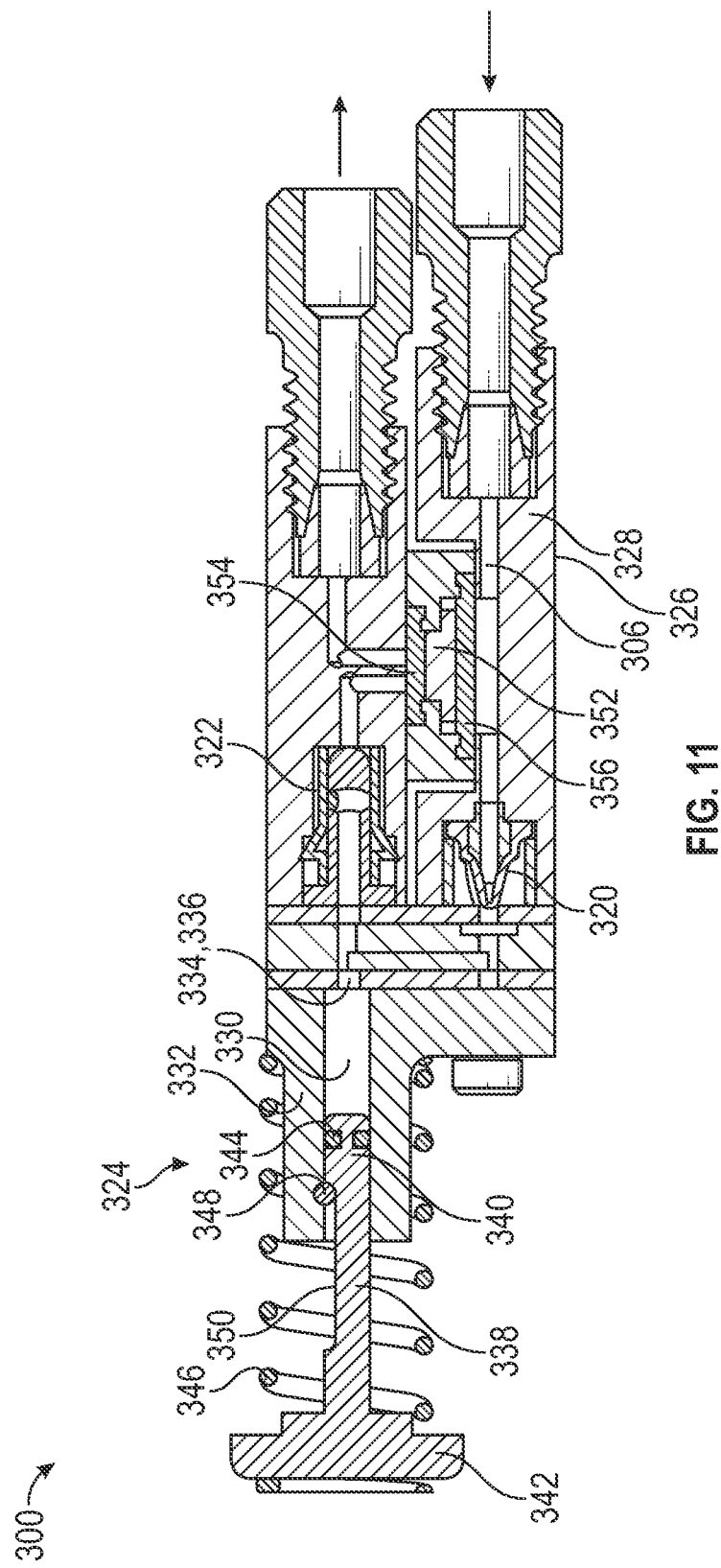
FIG. 11 depicts a bolus dose delivery system in accordance with one or more embodiments of the disclosure.

The bolus dose delivery system 300 is disposed along the bolus flow path 306. Generally speaking, the bolus dose delivery system 300 includes a first check valve 320, a second check valve 322 downstream of the first check valve 320, a piston pump 324 disposed between the first check valve 320 and the second check valve 322, and a pilot operated valve 326 in parallel to the piston pump 324. As depicted in FIGS. 10 and 11, in some instances, the first check valve 320, the second check valve 322, and the pilot operated valve 326 are disposed within a housing 328.

In some instances, the first check valve 320 comprises a duckbill valve, and the second check valve 322 comprises a PD valve. The first check valve 320 and the second check valve 322 may be any suitable check valve or the like.

In certain embodiments, the piston pump 324 comprises a bolus chamber 330. The bolus chamber 330 is formed within an enclosure 332 or the like. The enclosure 332 may be attached to or formed as part of the housing 328. In some instances, the size of the bolus chamber 330 corresponds to the bolus dose. In certain embodiments, the bolus chamber 330 accommodates 20 µl of fluid. The bolus chamber 330 may be any suitable size, shape, or configuration. The bolus chamber 330 includes an inlet 334 and an outlet 336. In some instances, the inlet 334 and the outlet 336 are one and the same. That is, the inlet 334 and the outlet 336 are relative depending on the status (i.e., filling or dispensing) of the bolus dose delivery system 300.

The piston pump 324 also includes a piston 338 at least partially disposed within the bolus chamber 330. The piston 338 is moveable. For example, a first end 340 of the piston 338 is disposed within the bolus chamber 330, while a second end 342 (e.g., a button portion) of the piston 338 opposite the first end 340 is disposed outside of the bolus chamber 330. In this manner, a user may engage (e.g., press) the button portion 342 of the piston 338 in order to administer the bolus dose. To prevent leaks, the piston 338 includes one or more seals 344 (e.g., O-rings or the like) disposed about the first end 340 of the piston 338 within the bolus chamber 330. The seals 344 form a seal between the piston 338 and the bolus chamber 330. In this manner, the seals 344 prevent leaks from the bolus chamber 330 as the piston 338 moves between a first position (i.e., bolus dose dispensing position), as depicted in FIG. 10, and a second position (i.e., bolus chamber filling position), as depicted in FIG. 11.

A spring 346 disposed about the piston 338 between the second end 342 of the piston 338 and the enclosure 332 biases the piston 338 in the second position. A user therefore has to press the piston 338 with enough force to overcome the spring force (resistance) of the spring 346 to move the piston 338 from the second position to the first position to administer the bolus dose. To prevent the spring 346 from removing the piston 338 from the bolus chamber 330 and to limit a stroke of the piston 338, a pin stop 348 is disposed within the enclosure 332 and located within a channel 350 in the piston 338.

In certain embodiments, the pilot operated valve 326 comprises a first position and a second position. In the first position, as depicted in FIG. 11, the bolus flow path 306 is closed downstream of the piston pump 324 and open upstream of the piston pump 324. Conversely, in the second position, the bolus flow path 306 is open downstream of the piston pump 324 and closed upstream of the piston pump 324. For example, the pilot operated valve 326 comprises a valve 352 moveably disposed between a first diaphragm 354 and a second diaphragm 356. As the valve 352 moves back and forth between the first position and the second position, the valve 352 may push or release the first diaphragm 354 and the second diaphragm 356. For instance, the first diaphragm 354 is configured to close (i.e., seal) the bolus flow path 306 downstream of the piston pump 324 when the valve 352 is in the first position. At the same time, the second diaphragm 356 will not obstruct the flow through the bolus flow path 306 when the valve 352 is in the first position. In this manner, in the first position, fluid flows from the reservoir 312, through the first check valve 320, and into the bolus chamber 330. The first position of the pilot operated valve 326 is the fill position. The pilot operated valve 326 is biased in the first position. Conversely, in some instances, the second diaphragm 356 is configured to close (i.e., seal) the bolus flow path 306 upstream of the piston pump 324 when the valve 352 is in the second position. At the same time, the first diaphragm 354 will not obstruct the flow through the bolus flow path 306 when the valve 352 is in the second position. In this manner, in the second position, fluid flows from the bolus chamber 330, through the second check valve 322, and into the cannula 318. The second position of the pilot operated valve 326 is the bolus dispensing position. In other instances, second diaphragm 356 will not obstruct the flow through the bolus flow path 306 when the valve 352 is in the second position. That is, the second diaphragm 356 will remain open, and the first check valve 320 will prevent backflow in the second position.

In use, the bolus chamber 330 is filled with the bolus dose when the pilot operated valve 326 is in the first position. A user can deliver the bolus dose from the microfluidic circuit 302 by actuating the piston 338. For example, a user can press the button portion 342 of the piston 338 to move the piston 338 from the second position to the first position. In such instances, a pressure within the bolus chamber 330 increases. At a certain pressure, the pilot operated valve 326 moves from the first position to the second position. That is, the pilot operated valve 326 moves from the first position, in which the bolus flow path 306 is closed downstream of the bolus chamber 330 and open upstream of the bolus chamber 330, to the second position, in which the bolus flow path 306 is open downstream of the bolus chamber 330 and closed upstream of the bolus chamber 330. When the pilot operated valve 326 is in the second position, the bolus dose is delivered to the cannula 318. Once the user releases the button portion 342 of the piston 338, the spring 346 biases the piston 338 back to the second position. In this configuration, the pressure within the bolus chamber 330 is decreased, and the pilot operated valve 326 moves back from the second position to the first position, allowing the bolus chamber 330 to fill with another bolus dose. This process may be repeated as needed to deliver bolus doses to the user.

Figure 12:
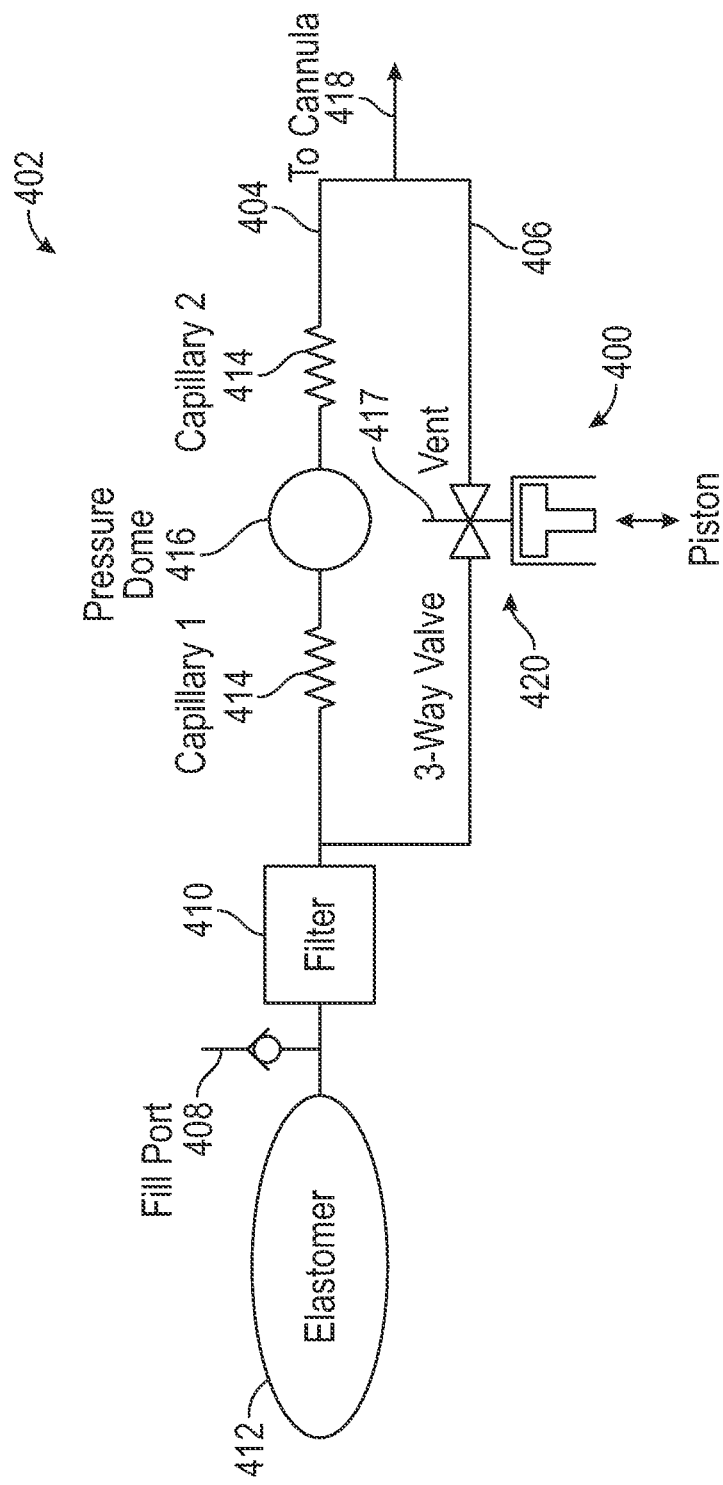
FIG. 12 depicts a microfluidic circuit of a fluid medicament delivery device in accordance with one or more embodiments of the disclosure.

FIG. 12 depicts one example of a bolus dose delivery system 400 incorporated into a microfluidic circuit 402 of a fluid medicament delivery device (e.g., an insulin pump or the like) configured to administer a medication in fluid form. In other instances, the bolus dose delivery system 400 may be incorporated into the microfluidic circuit 100. The bolus dose delivery system 400 may be incorporated into any suitable medicament delivery device.

The microfluidic circuit 402 includes a basal flow path 404 and a bolus flow path 406 in parallel to each other. A fill port 408 is disposed upstream of the basal flow path 404 and the bolus flow path 406 between a filter 410 and a reservoir 412. The filter 410 may be any suitable size, shape, or configuration. The fill port 408 may be positioned at any suitable location within the microfluidic circuit 402. In some instances, the reservoir 412 comprises an elastomeric bladder. The fill port 408 may include a check valve and is used to introduce insulin (or other medication) to the microfluidic circuit 402. Introducing insulin via the fill port 408 fills, among other things, the reservoir 412. The basal flow path 404 includes two flow restrictors 414 in series, with at least one pressure sensor 416 disposed between the two flow restrictors 414. A cannula 418 is disposed downstream of the basal flow path 404 and the bolus flow path 406. The cannula 418 extends into/through the skin of the user, thus delivering the insulin subcutaneously. The microfluidic circuit 402 may include additional components. Conversely, certain components may be omitted. In any case, the microfluidic circuit 402 may be configured to deliver one or more medicaments or combinations thereof in fluid form.

The bolus dose delivery system 400 is disposed along the bolus flow path 406. Generally speaking, the bolus dose delivery system 400 comprises a combined piston pump and rotatable valve 420, which includes a vent 417. As depicted in FIGS. 13-16F, the combined piston pump and rotatable valve 420 includes a base 422. The base 422 includes a tubular portion 424 extending therefrom. The base 422 includes an inlet 426 and an outlet 428. The inlet 426 and the outlet 428 are in fluid communication with the bolus flow path 406 and the tubular portion 424. The base 422 may be any suitable size, shape, or configuration.

Figure 16A:
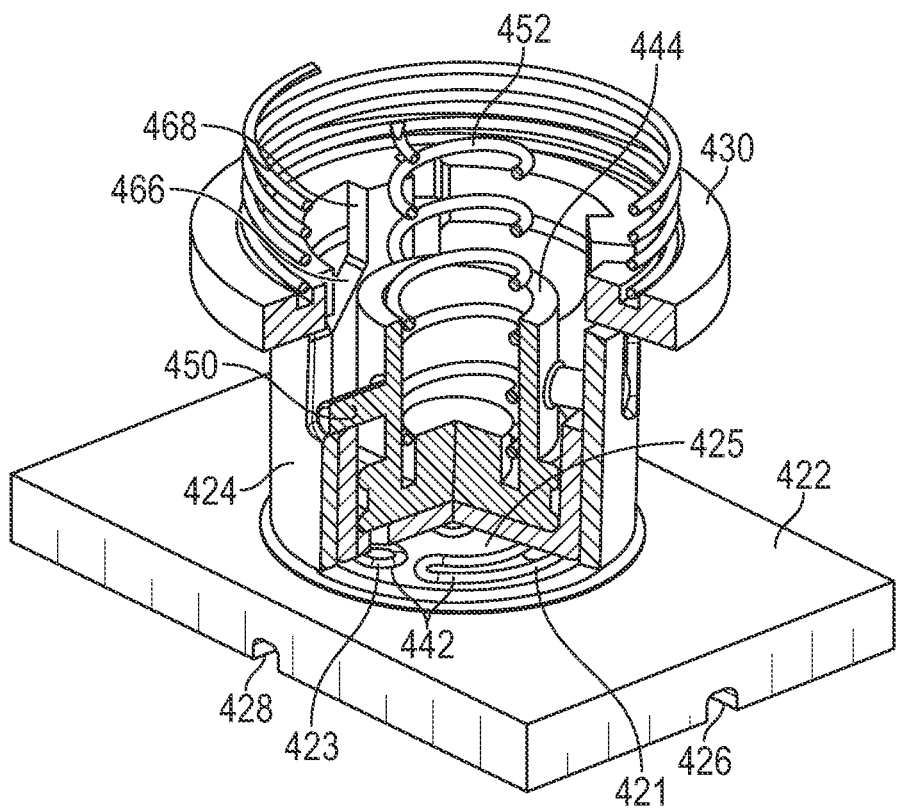
FIGS. 16A-16F depict a sequence of a bolus dose delivery system in accordance with one or more embodiments of the disclosure.
Figure 16B:
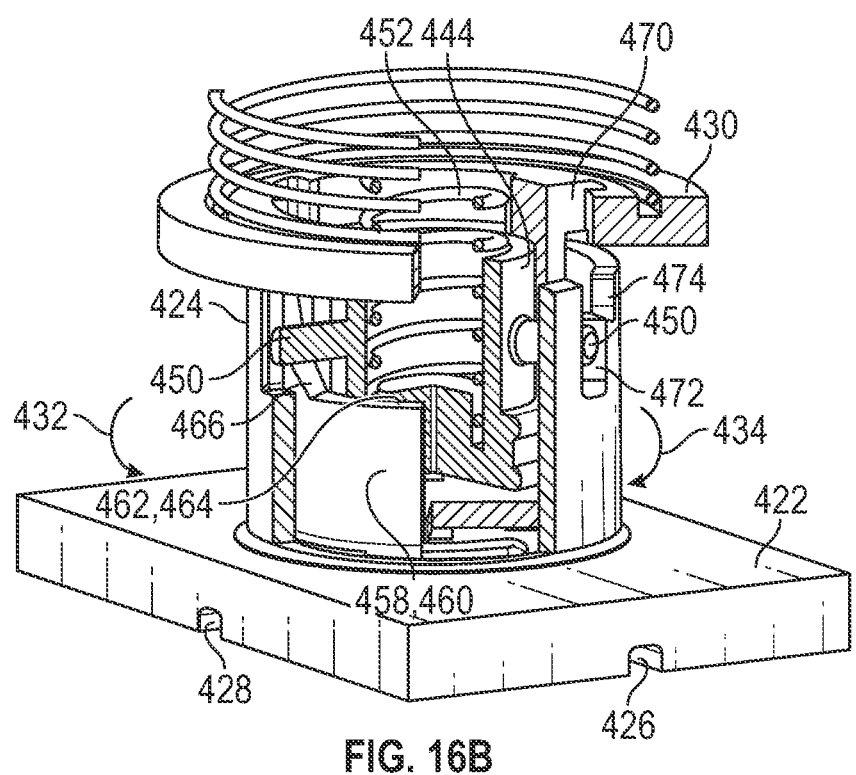
Figure 16C:
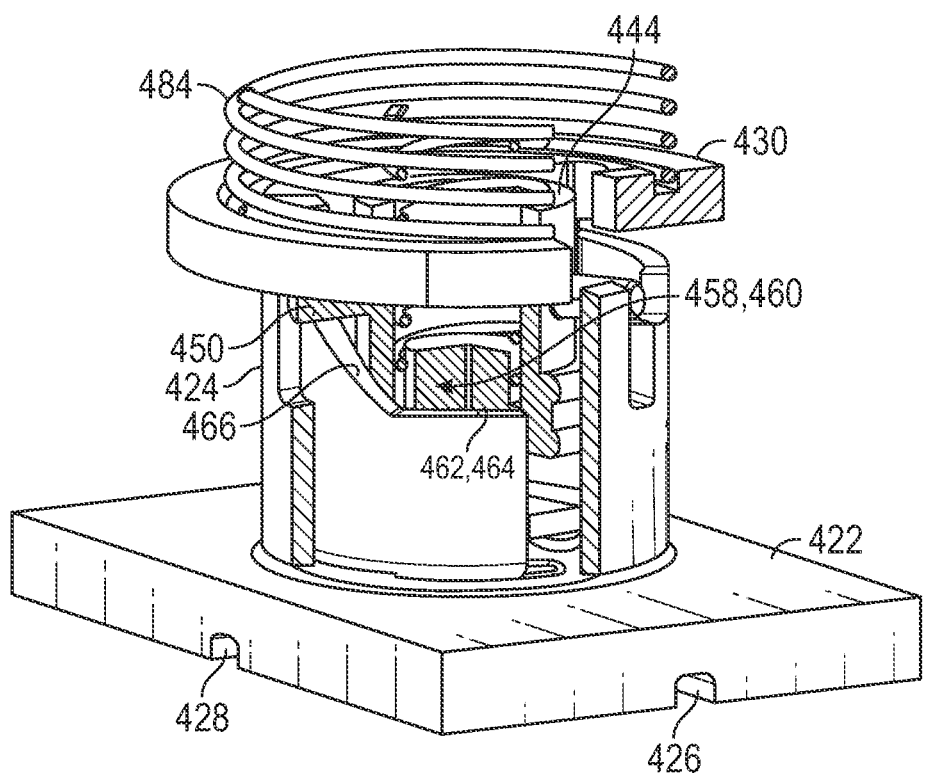
Figure 16D:
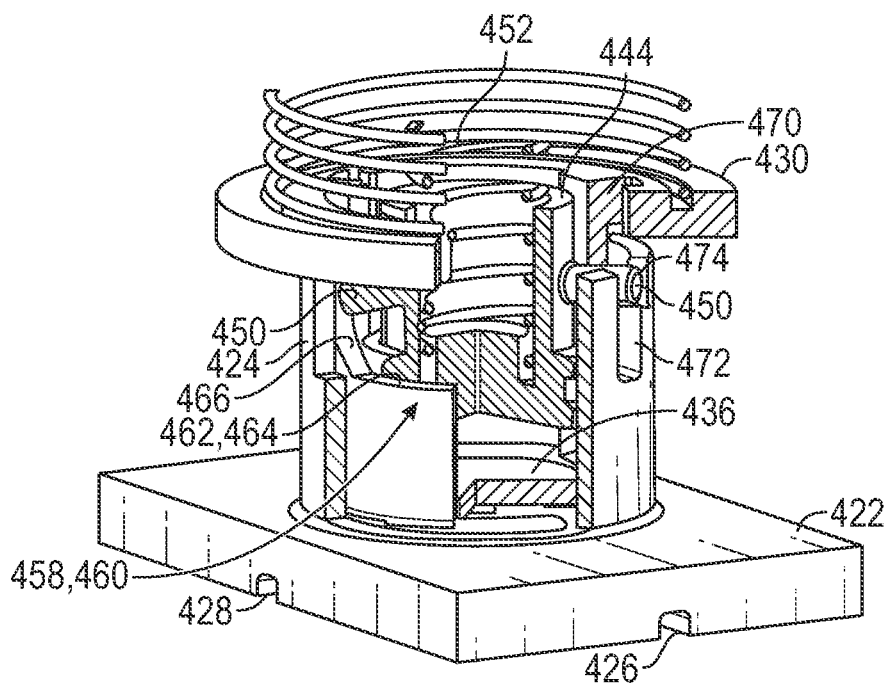
Figure 16E:
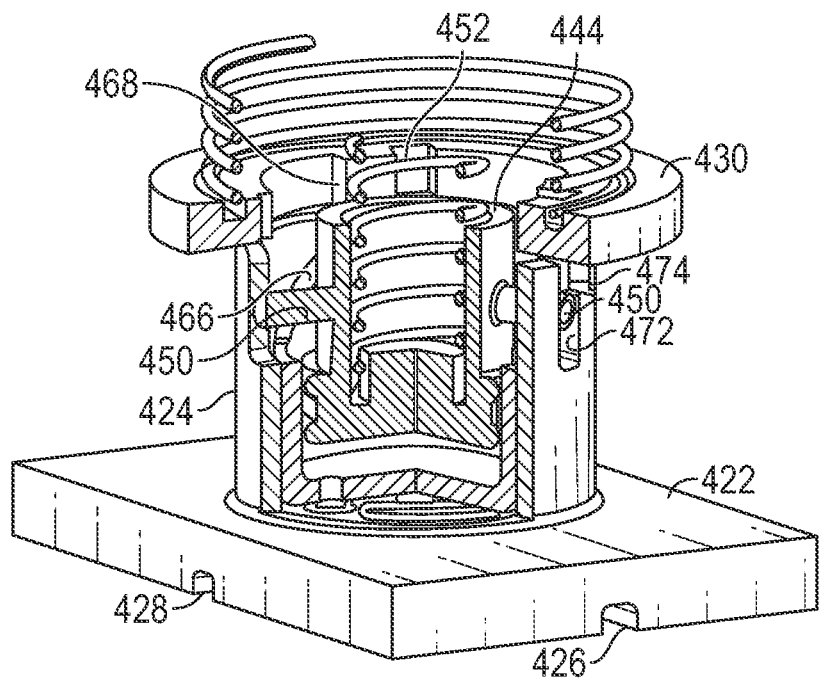
Figure 16F:
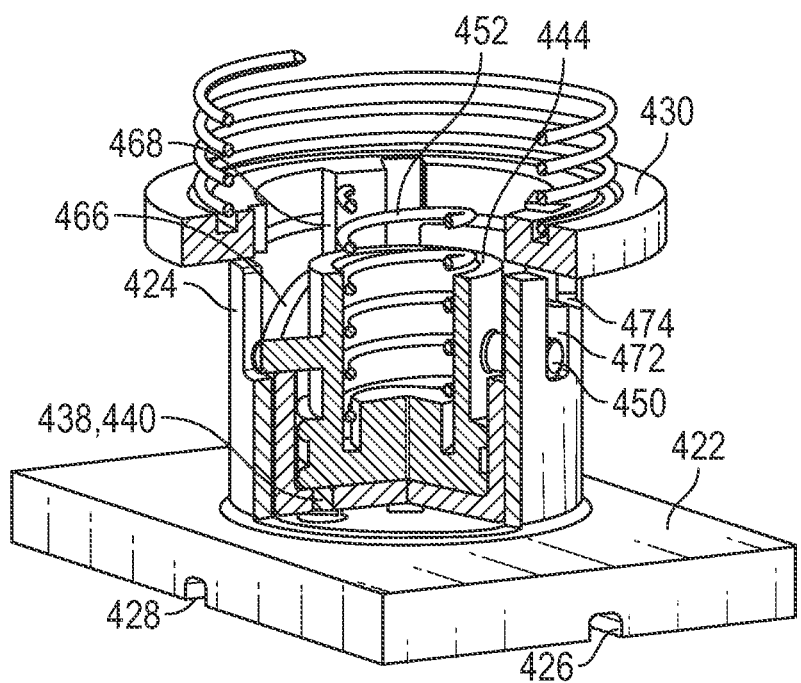

A rotatable valve body 430 is rotatably disposed about the base 422. In certain embodiments, the valve body 430 is rotatably disposed at least partially within the tubular portion 424. In this manner, the valve body 430 can rotate a first direction 432 or a second direction 434, as depicted in FIG. 16B, within the tubular portion 424. The valve body 430 includes a bolus chamber 436 formed therein, as depicted in FIG. 16D. In some instances, the size of the bolus chamber 436 corresponds to the bolus dose. In certain embodiments, the bolus chamber 436 accommodates 20 μl of fluid. The bolus chamber 436 may be any suitable size, shape, or configuration. The bolus chamber 436 includes an inlet 438 and an outlet 440, as depicted in FIG. 16F. In some instances, the inlet 438 and the outlet 440 are one in the same. That is, the inlet 438 and the outlet 440 of the bolus chamber 436 are relative depending on the status (i.e., filling or dispensing) of the bolus dose delivery system 400. In some instances, the inlet 426 of the base 422 is in fluid communication with the inlet 438 of the bolus chamber 436 via a fill pocket 421. In other instances, the outlet 428 of the base 422 is in fluid communication with the outlet 440 of the bolus chamber 436 via a dose pocket 423. To prevent leaks between the bolus chamber 436 and the base 422, seals 442 are disposed about the inlet 426 and the outlet 428 of the base 422. The seals 442 form the fill pocket 421 and the dose pocket 423. The valve body 430 rotates about the seals 442. Additional seals or structures may be disposed about the base 422 to provide symmetry along the interface between the valve body 430 and the base 422.

Figure 14:
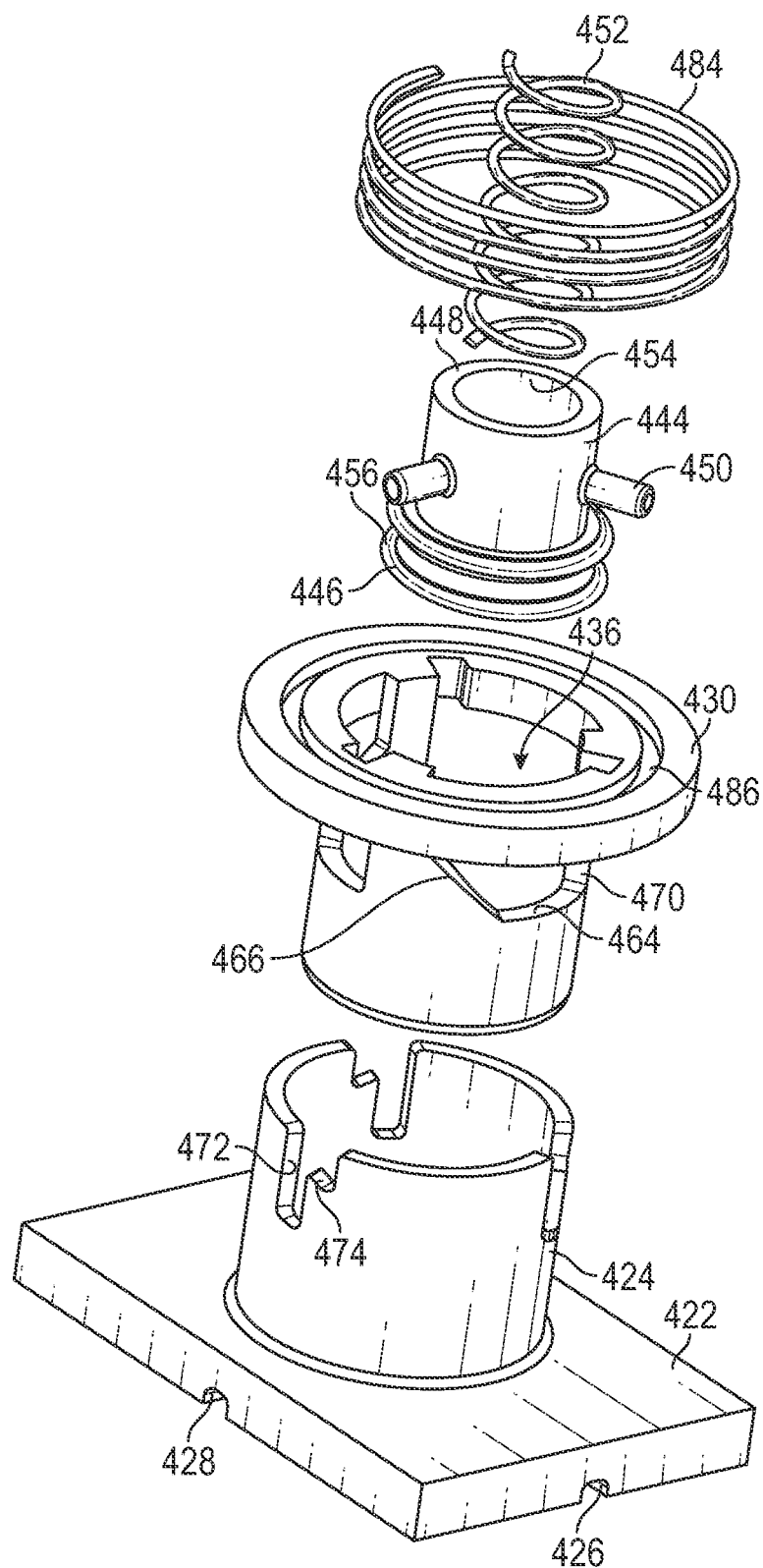
Figure 15:
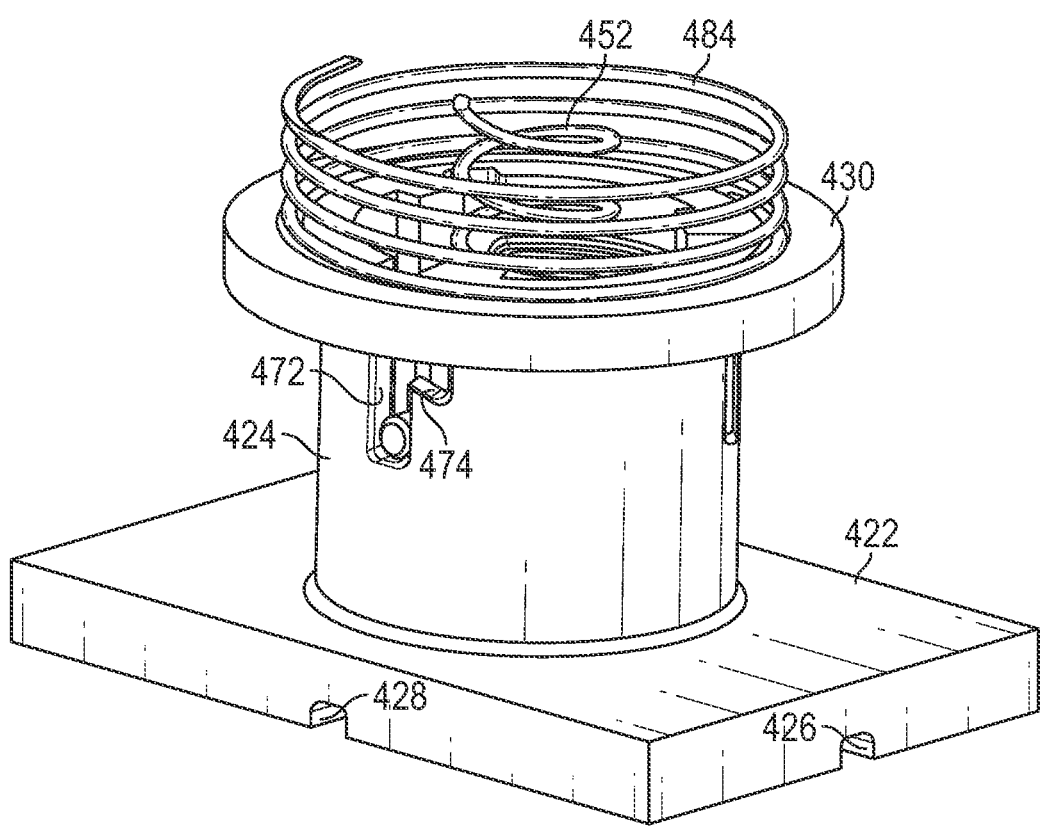

As depicted in FIG. 14, the combined piston pump and rotatable valve 420 includes a moveable and rotatable piston 444 at least partially disposed within the bolus chamber 436 and in mechanical communication with (e.g., disposed within and in rotatable contact with) the valve body 430. For example, a first end 446 of the piston 444 is disposed within the bolus chamber 436, while a second end 448 of the piston 444 opposite the first end 446 is disposed outside of the bolus chamber 436 and comprises a protrusion 450 in mechanical communication with (e.g., contacting) the valve body 430. In this manner, as depicted in FIGS. 16A-16F, when the valve body 430 rotates, the piston 444 moves between a first position and a second position in order to administer the bolus dose. A piston spring 452 is disposed about the piston 444. The piston spring 452 biases the piston 444 in the first position. In some instances, the piston spring 452 is disposed within an opening 454 in the second end 448 of the piston 444.

To prevent leaks, the piston 444 includes one or more seals 456 (e.g., O-rings or the like) disposed about the first end 446 of the piston 444 within the bolus chamber 436. The seals 456 form a seal between the piston 444 and the bolus chamber 436. In this manner, the seals 456 prevent leaks from the bolus chamber 436 as the piston 444 moves between the first position (i.e., bolus dose dispensing position), as depicted in FIG. 16A, and the second position (i.e., bolus chamber filling position), as depicted in FIG. 16D.

To move the piston 444 from the first position to the second position, the valve body 430 comprises a cam 458. The cam 458 may be any suitable size, shape, or configuration. As depicted in FIGS. 16A-16F, the cam 458 is configured to rotate and move the piston 444 between the first position and the second position. In this manner, the cam 458 transforms the rotational movement of the valve body 430 into linear movement of the piston 444. In some instances, the cam 458 comprises a cutout 460 having a cam surface 462 in a side of the valve body 430. The protrusion 450 is disposed within the cutout 460 and is in contact with the cam surface 462. For example, the piston spring 452 biases the protrusion 450 against at least a portion of the cam surface 462.

In certain embodiments, the cam surface 462 includes a first portion 464, a second portion 466, a third portion 468, and a fourth portion 470. The first portion 464 may be substantially transverse to the linear movement of the piston 444. In this manner, the first portion 464 of the cam surface 462 does not move the protrusion 450 as the valve body 430 rotates. In some instances, the first portion 464 of the cam surface 462 may be omitted. The second portion 466 of the cam surface 462 is inclined relative to the first portion 464 of the cam surface 462. In this manner, the protrusion 450 rides up the second portion 466 of the cam surface 462 as the valve body 430 rotates in the first direction 432, which causes the piston 444 to move from the first position to the second position. The third portion 468 of the cam surface 462 is located at an end of the second portion 466 of the cam surface 462 and is substantially parallel to the linear movement of the piston 444. In this manner, the third portion 468 of the cam surface 462 causes the protrusion 450 to rotate the piston 444 in the first direction 432 as the valve body 430 rotates in the first direction 432. The fourth portion 470 of the cam surface 462 is located opposite the third portion 468 and is substantially parallel to the linear movement of the piston 444. As discussed below, the fourth portion 470 of the cam surface 462 moves the piston 444 from the second position to the first position.

To maintain the piston 444 in the second position, the tubular portion 424 of the base 422 includes a channel 472 with a lip 474. The protrusion 450 is also located within the channel 472. The channel 472 is substantially parallel to the linear movement of the piston 444. In some instances, the length of the channel 472 corresponds to the second portion 466 of the cam surface 462. For example, the protrusion 450 moves from a bottom of the channel 472 to a top of the channel 472 adjacent the lip 474 as the protrusion 450 rides up the second portion 466 of the cam surface 462 during rotation of the valve body 430 in the first direction 432. Similarly, the location of the lip 474 corresponds to the third portion 468 of the cam surface 462. For example, the protrusion 450 can rotate from the top of the channel 472 and into the lip 474 as the protrusion 450 is rotated (e.g., pushed) by the third portion 468 of the cam surface 462 during rotation of the valve body 430 in the first direction 432. When the protrusion 450 is located within the lip 474, the piston 444 is "locked" in the second position.

Figure 13:
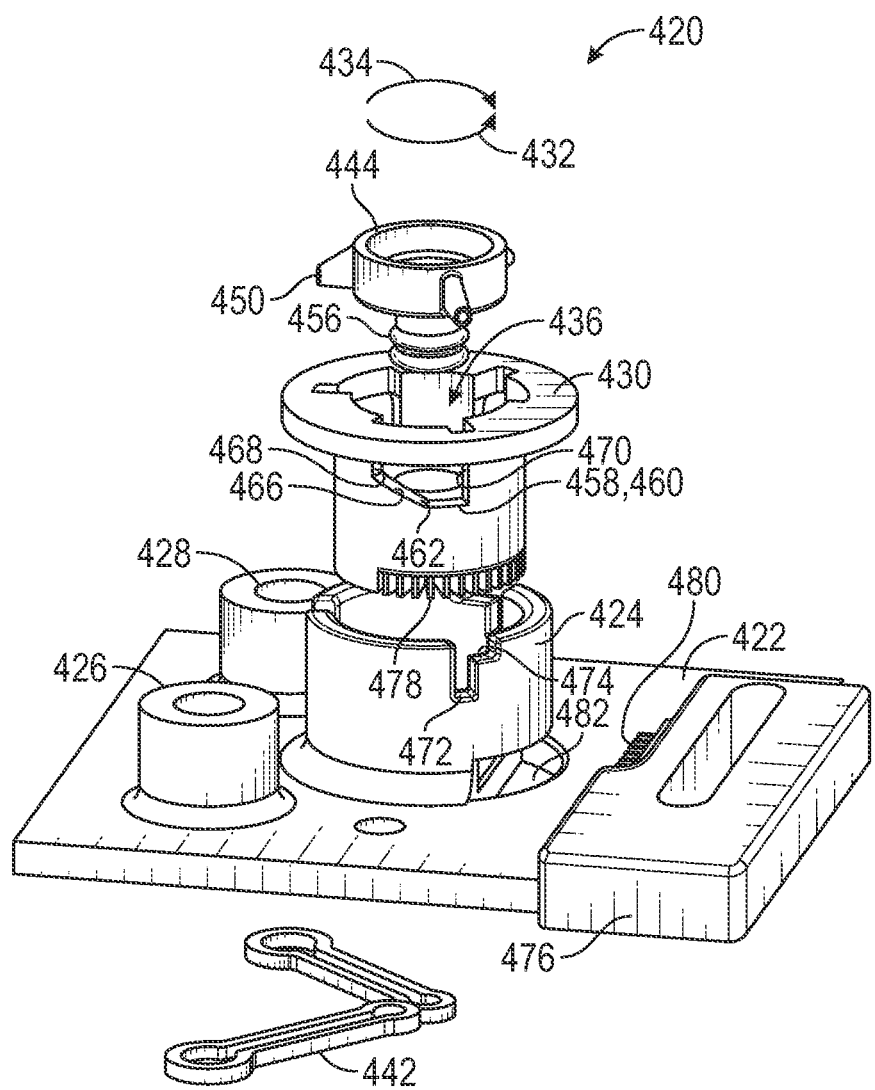
FIGS. 13-15 depict a bolus dose delivery system in accordance with one or more embodiments of the disclosure.

As depicted in FIG. 13, the valve body 430 can be rotated in the first direction 432 or the second direction 434 via an actuator 476 or the like in mechanical communication with the valve body 430. The actuator 476 may comprise a button or the like that a user pushes. In some instances, the actuator 476 is in mechanical communication with the valve body 430 via a rack and pinion. For example, the valve body 430 includes a circular gear 478 (or pinion), and the actuator 476 includes a linear gear 480 (or rack). In this manner, teeth on the linear gear 480 of the actuator 476 pass through a void 482 in the tubular portion 424 to engage teeth on the circular gear 478 of the valve body 430 to rotate the valve body 430 in the first direction 432 or the second direction 434.

A valve spring 484 is disposed about the valve body 430. The valve spring 484 is located within a groove 486 in the valve body 430. The valve spring 484 biases the rotation of the valve body 430 in the second direction 434. In this manner, to move the piston 444 from the second position to the first position, the valve body 430 rotates in the second direction 434, which causes the fourth portion 470 of the cam surface 462 to contact and rotate the protrusion 450 out of the lip 474 and back into the top of the channel 472. The piston spring 452 then forces the protrusion 450 from the top of the channel 472 to the bottom of the channel 472, which in turn moves the piston 444 from the second position to the first position. That is, the protrusion 450 rotates from the lip 474 and into the top of the channel 472 as the protrusion 450 is rotated (e.g., pushed) by the fourth portion 470 of the cam surface 462 during rotation of the valve body 430 in the second direction 434. The combined piston pump and rotatable valve 420 can include a plurality of protrusions 450, a plurality of cams 458, and a plurality of channels 472.

In use, the bolus chamber 436 is filled with the bolus dose when the piston 444 is moved from the first position to the second position. In the first position, as depicted in FIG. 16F, the inlet 438 to the bolus chamber 436 is blocked. That is, the inlet 438 to the bolus chamber is not in fluid communication with the inlet 426 of the base 422. The actuator 476 rotates the valve body 430 in the first direction 432, which causes the protrusion 450 to ride up the second portion 466 of the cam surface 462 from the bottom of the channel 472 to the top of the channel 472, which causes the piston 444 to move from the first position to the second position. The third portion 468 of the cam surface 462 then contacts the protrusion 450 to rotate the piston 444 in the first direction 432 from the top of the channel 472 and into the lip 474 to "lock" the piston 444 in the second position. In the second position, as depicted in FIG. 16D, the inlet 438 to the bolus chamber 436 is in fluid communication with the inlet 426 of the base 422, enabling the bolus chamber 436 to be filled with the bolus dose. The valve body 430 then rotates in the second direction 434, which causes the fourth portion 470 of the cam surface 462 to contact and rotate the protrusion 450 out of the lip 474 and back into the top of the channel 472. The piston spring 452 then forces the protrusion 450 from the top of the channel 472 to the bottom of the channel 472, which in turn moves the piston 444 from the second position to the first position. At the same time (or very close thereto), the outlet 440 of the bolus chamber 436 is in fluid communication with the outlet 428 of the base 422, which permits or enables transfer/flow of the bolus dose from the bolus chamber 436 to the cannula 418. This process may be repeated as needed to deliver bolus doses to the user. In some instances, as the piston 444 moves between the first position and the second position (or vice versa), the inlet 438/outlet 440 is located in the area between the fill pocket 421 and the dose pocket 423 as the rotatable valve body 430 rotates. In such instances, medicament may be released into a void 425 between the rotatable valve body 430 and the base 422. The medicament located in the void 425 between the rotatable valve body 430 and the base 422 is vented via the vent 417 to a location outside of the combined piston pump and rotatable valve 420 and away from the patient. That is, any medicament located in the void 425 between the rotatable valve body 430 and the base 422 is not delivered to the patient.

Figure 17:
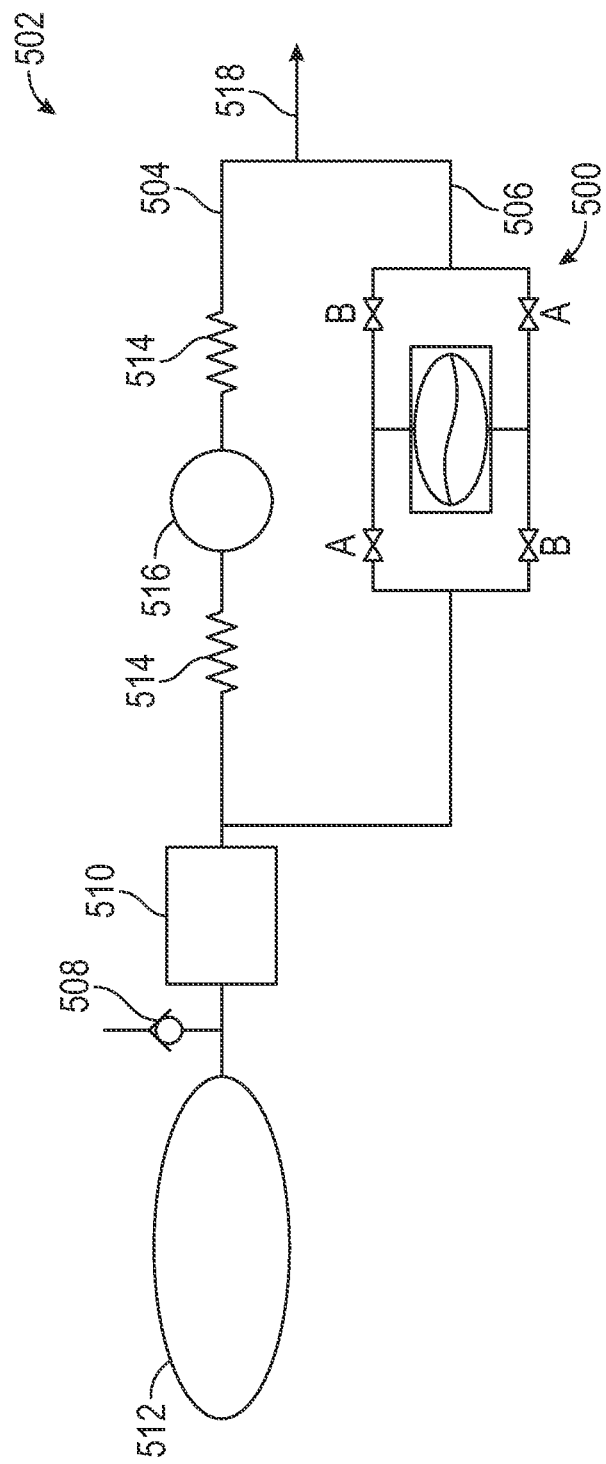
FIG. 17 depicts a microfluidic circuit of a fluid medicament delivery device in accordance with one or more embodiments of the disclosure.

FIG. 17 depicts one example of a bolus dose delivery system 500 incorporated into a microfluidic circuit 502 of a fluid medicament delivery device (e.g., an insulin pump or the like) configured to administer a medication in fluid form. In other instances, the bolus dose delivery system 500 may be incorporated into the microfluidic circuit 100. The bolus dose delivery system 500 may be incorporated into any suitable medicament delivery device.

The microfluidic circuit 502 includes a basal flow path 504 and a bolus flow path 506 in parallel to each other. A fill port 508 is disposed upstream of the basal flow path 504 and the bolus flow path 506 between a filter 510 and a reservoir 512. The filter 510 may be any suitable size, shape, or configuration. The fill port 508 may be located at any location within the microfluidic circuit 502. In some instances, the reservoir 512 comprises an elastomeric bladder. The fill port 508 may include a check valve and is used to introduce insulin (or other medication) to the microfluidic circuit 502. Introducing insulin via the fill port 508 fills, among other things, the reservoir 512. The basal flow path 504 includes two flow restrictors 514 in series, with at least one pressure sensor 516 disposed between the two flow restrictors 514. A cannula 518 is disposed downstream of the basal flow path 504 and the bolus flow path 506. The cannula 518 extends into/through the skin of the user, thus delivering the insulin subcutaneously. The microfluidic circuit 502 may include additional components. Conversely, certain components may be omitted. In any case, the microfluidic circuit 502 may be configured to deliver one or more medicaments or combinations thereof in fluid form.

Figure 18A:
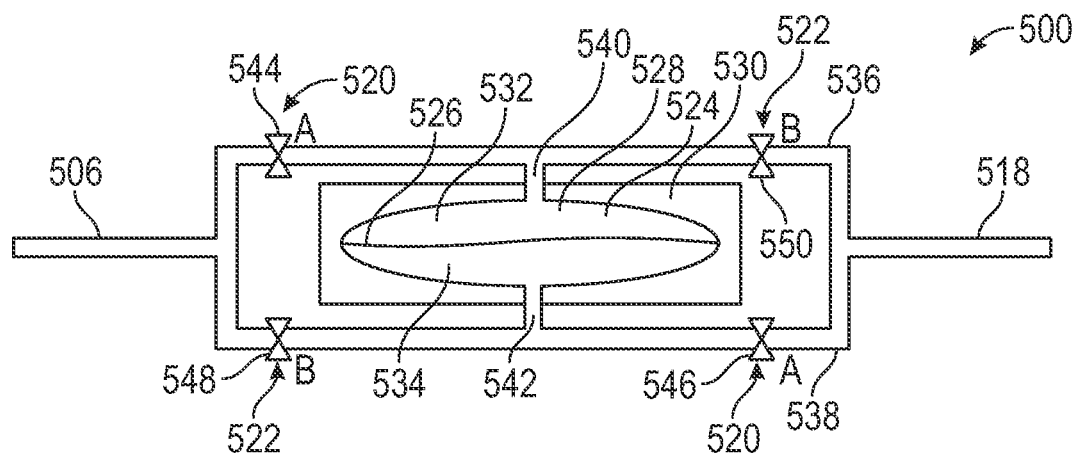
FIGS. 18A-18C depict a bolus dose delivery system in accordance with one or more embodiments of the disclosure.

The bolus dose delivery system 500 is disposed along the bolus flow path 506. The bolus dose delivery system 500 does not include a pump, a cylinder, or a piston in order to administer the bolus dose. Instead, as depicted in FIG. 18A, the bolus dose delivery system 500 comprises a first valve set 520 ("A" valves), a second valve set 522 ("B" valves), a bolus chamber 524, and a flexible membrane 526 disposed within the bolus chamber 524. In some instances, the size of the bolus chamber 524 corresponds to the bolus dose. In certain embodiments, the bolus chamber 524 accommodates 20 μl of fluid. The bolus chamber 524 may be any suitable size, shape, or configuration. In certain embodiments, the bolus chamber 524 is formed as a fixed cavity 528 within a body 530. The flexible membrane 526 divides the bolus chamber 524 into a first portion 532 and a second portion 534 and is configured to cycle back and forth within the bolus chamber 524 to force the medication from the bolus chamber 524 to the cannula 518 due to the opening of the first valve set 520 and the closing of the second valve set 522, or vice versa. That is, the flexible membrane 526 cycles back and forth within the bolus chamber 524 due to the pressure differential created by the opening of the first valve set 520 and the closing of the second valve set 522, or vice versa.

The bolus flow path 506 comprises a first flow path 536 and a second flow path 538 in parallel. Although the first flow path 536 and the second flow path 538 are in parallel, as discussed below, the arrangement and operation of the first valve set 520 and the second valve set 522 prevents parallel fluid flow through the bolus dose delivery system 500. The bolus chamber 524 is disposed in fluid communication with the first flow path 536 and the second flow path 538. That is, the first portion 532 of the bolus chamber 524 comprises a first opening 540 between the first flow path 536, and the second portion 534 of the bolus chamber 524 comprises a second opening 542 between the second flow path 538. In some instances, the bolus chamber 524 is disposed between the first flow path 536 and the second flow path 538.

Figure 18B:
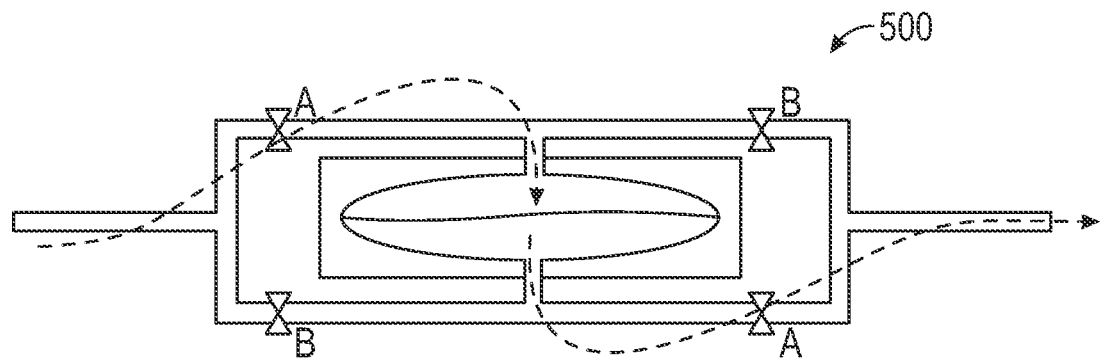
Figure 18C:
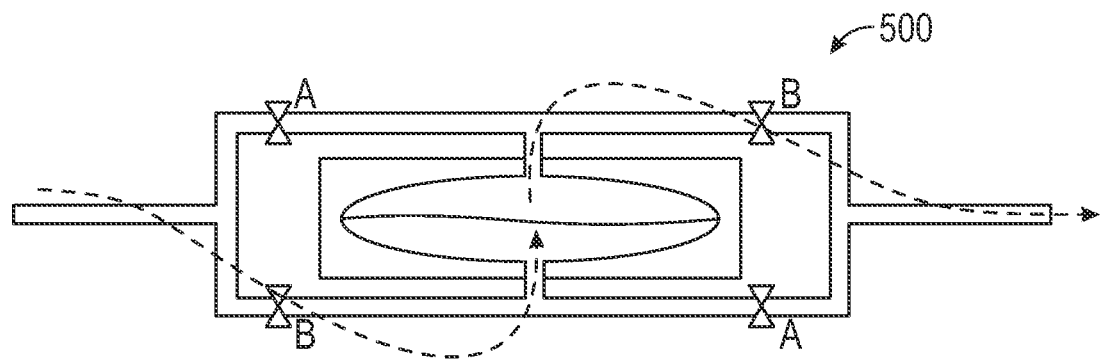

The first valve set 520 comprises a first valve 544 and a second valve 546. Similarly, the second valve set 522 comprises a third valve 548 and a fourth valve 550. The first valve 544 is disposed along the first flow path 536 upstream of the bolus chamber 524, and the second valve 546 is disposed along the second flow path 538 downstream of the bolus chamber 524. Similarly, the third valve 548 is disposed along the second flow path 538 upstream of the bolus chamber 524, and the fourth valve 550 is disposed along the first flow path 536 downstream of the bolus chamber 524. In this manner, when the first valve 544 and the second valve 546 are open, the third valve 548 and the fourth valve 550 are closed. In this configuration, as depicted in FIG. 18B, the first opening 540 in the bolus chamber 524 acts as an inlet to the first portion 532 of the bolus chamber 524, and the second opening 542 in the bolus chamber 524 acts as an outlet to the second portion 534 of the bolus chamber 524. Conversely, when the third valve 548 and the fourth valve 550 are open, the first valve 544 and the second valve 546 are closed. In this configuration, as depicted in FIG. 18C, the first opening 540 in the bolus chamber 524 acts as an outlet to the first portion 532 of the bolus chamber 524, and the second opening 542 in the bolus chamber 524 acts as an inlet to the second portion 534 of the bolus chamber 524.

In use, the first valve set 520 and the second valve set 522 cannot be opened at the same time. Rather, when one valve set is open, the other valve set is closed. In this manner, the flexible membrane 526 cycles back and forth within the bolus chamber 524 due to the pressure differential created by the opening of the first valve set 520 and the closing of the second valve set 522, or vice versa. As a result, the bolus dose delivery system 500 simultaneously administers the bolus dose to the cannula 518 and fills the bolus chamber 524 with a future bolus dose. For example, as depicted in FIG. 18B, when the first valve set 520 is opened, the second valve set 522 is closed. In this configuration, the first portion 532 of the bolus chamber 524 is filled with a bolus dose. At the same time, the bolus dose disposed within the second portion 534 of the bolus chamber 524 is forced out of the second opening 542 to the cannula 518 via the flexible membrane 526. In the opposite configuration, as depicted in FIG. 18C, when the first valve set 520 is closed, the second valve set 522 is opened. In this configuration, the second portion 534 of the bolus chamber 524 is filled with a bolus dose. At the same time, the bolus dose disposed within the first portion 532 of the bolus chamber 524 is forced out of the first opening 540 to the cannula 518 via the flexible membrane 526. Thus, as noted above, the flexible membrane 526 cycles back and forth within the bolus chamber 524 due to the pressure differential created by the opening of the first valve set 520 and the closing of the second valve set 522, or vice versa. This process may be repeated as needed to deliver bolus doses to the user. In some instances, an actuator (e.g., a button) may control the operation of the valve sets. In other instances, the actuator may be in communication with a controller or the like.

Figure 19:
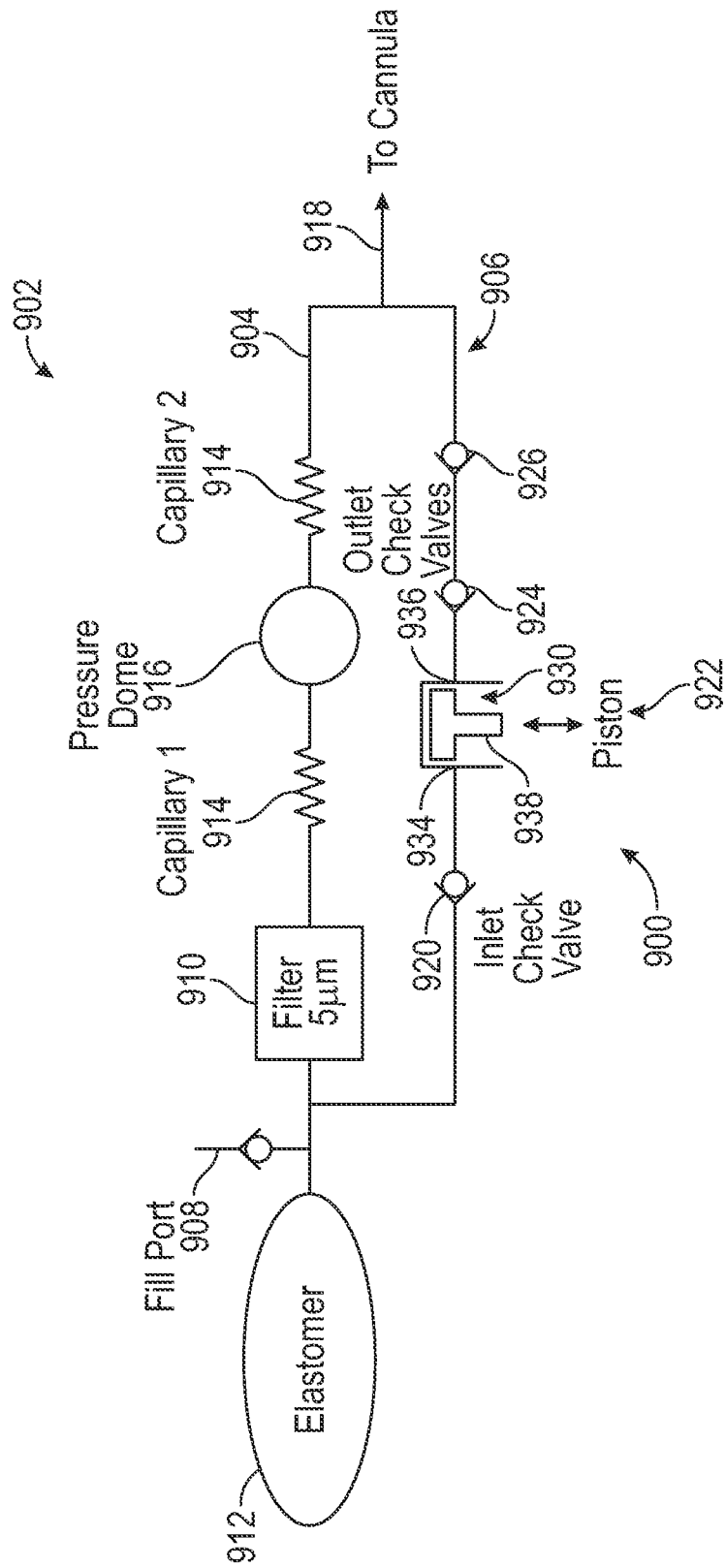
FIG. 19 depicts a microfluidic circuit of a fluid medicament delivery device in accordance with one or more embodiments of the disclosure.

FIG. 19 depicts an example bolus dose delivery system 900 incorporated into a microfluidic circuit 902 of a fluid medicament delivery device (e.g., an insulin pump or the like) configured to administer a medication in fluid form. In other instances, the bolus dose delivery system 900 may be incorporated into the microfluidic circuit 100. The bolus dose delivery system 900 may be incorporated into any suitable medicament delivery device.

The microfluidic circuit 902 includes a basal flow path 904 and a bolus flow path 906 in parallel to each other. A fill port 908 is disposed upstream of the basal flow path 904 and the bolus flow path 906 between a filter 910 and a reservoir 912. The filter 910 may be any suitable size, shape, or configuration. The fill port 908 may be located at any location within the microfluidic circuit 902. In some instances, the reservoir 912 comprises an elastomeric bladder. The fill port 908 may include a check valve and is used to introduce insulin (or other medication) to the microfluidic circuit 902. Introducing insulin via the fill port 908 fills, among other things, the reservoir 912. The basal flow path 904 includes two flow restrictors 914 in series, with at least one pressure sensor 916 disposed between the two flow restrictors 914. A cannula 918 is disposed downstream of the basal flow path 904 and the bolus flow path 906. The cannula 918 extends into/through the skin of the user, thus delivering the insulin subcutaneously. The microfluidic circuit 902 may include additional components. Conversely, certain components may be omitted. In any case, the microfluidic circuit 902 may be configured to deliver one or more medicaments or combinations thereof in fluid form.

Figure 20A:
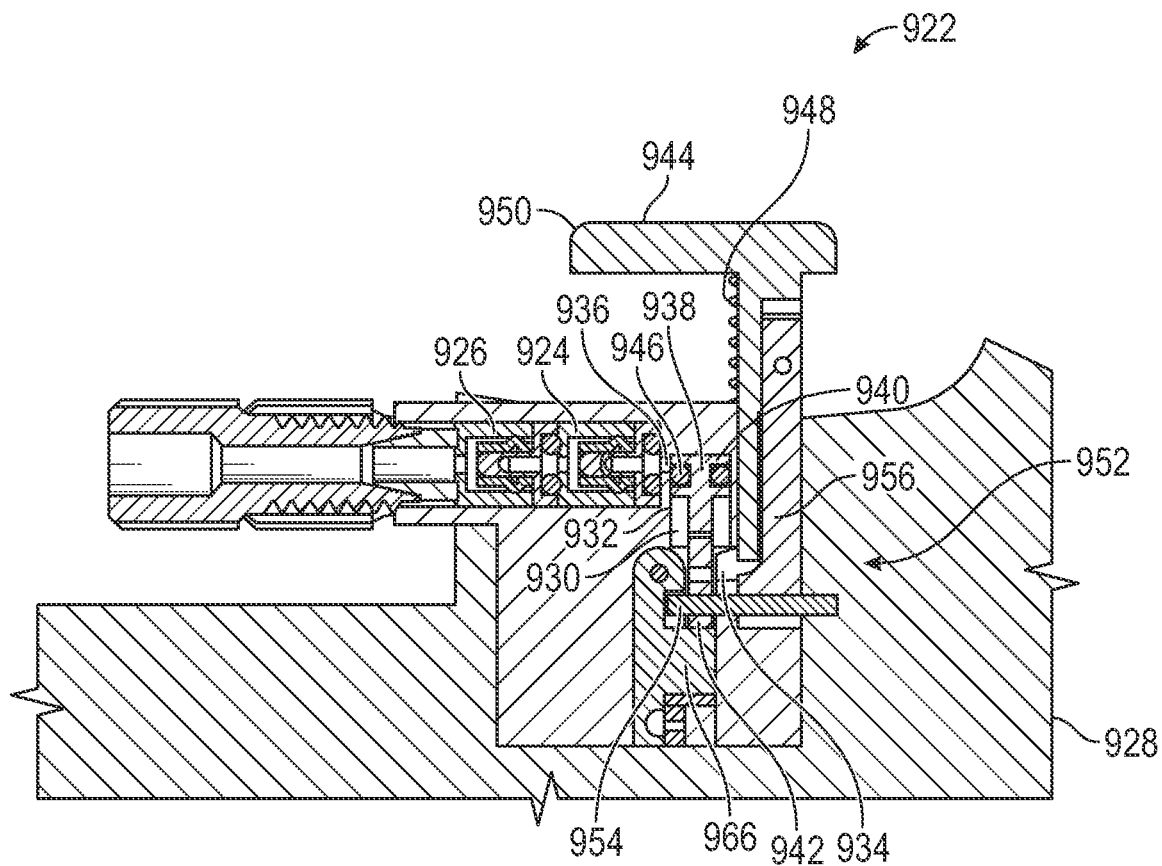
FIGS. 20A-20C depict a bolus dose delivery system in accordance with one or more embodiments of the disclosure.
Figure 20B:
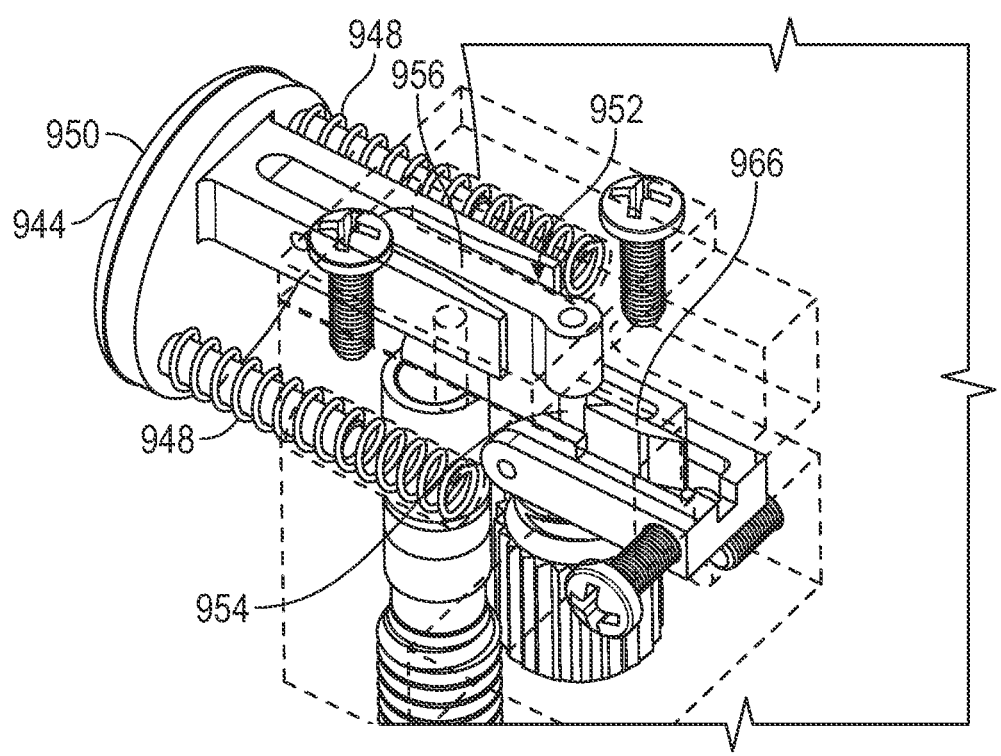
Figure 20C:
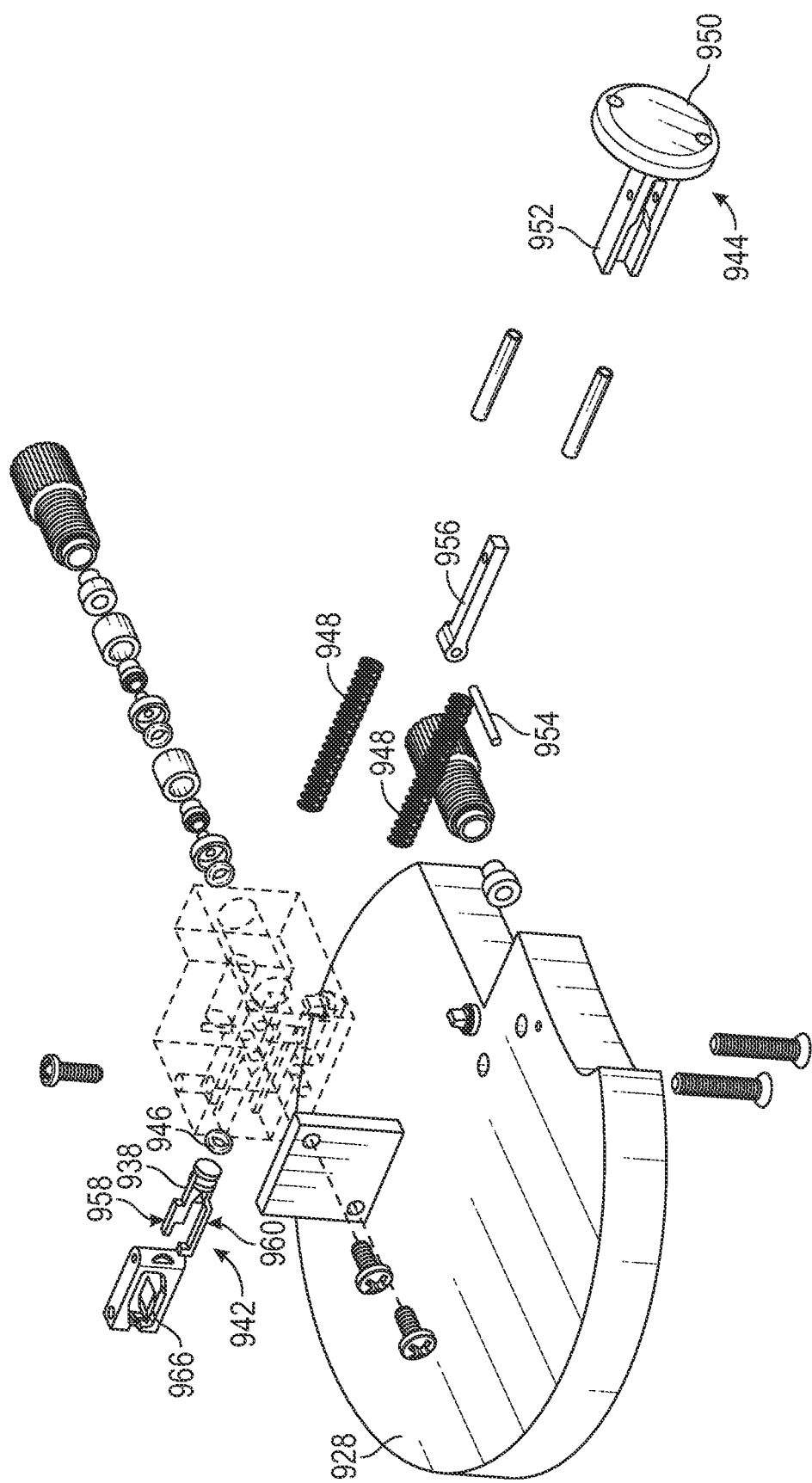
Figure 20D:
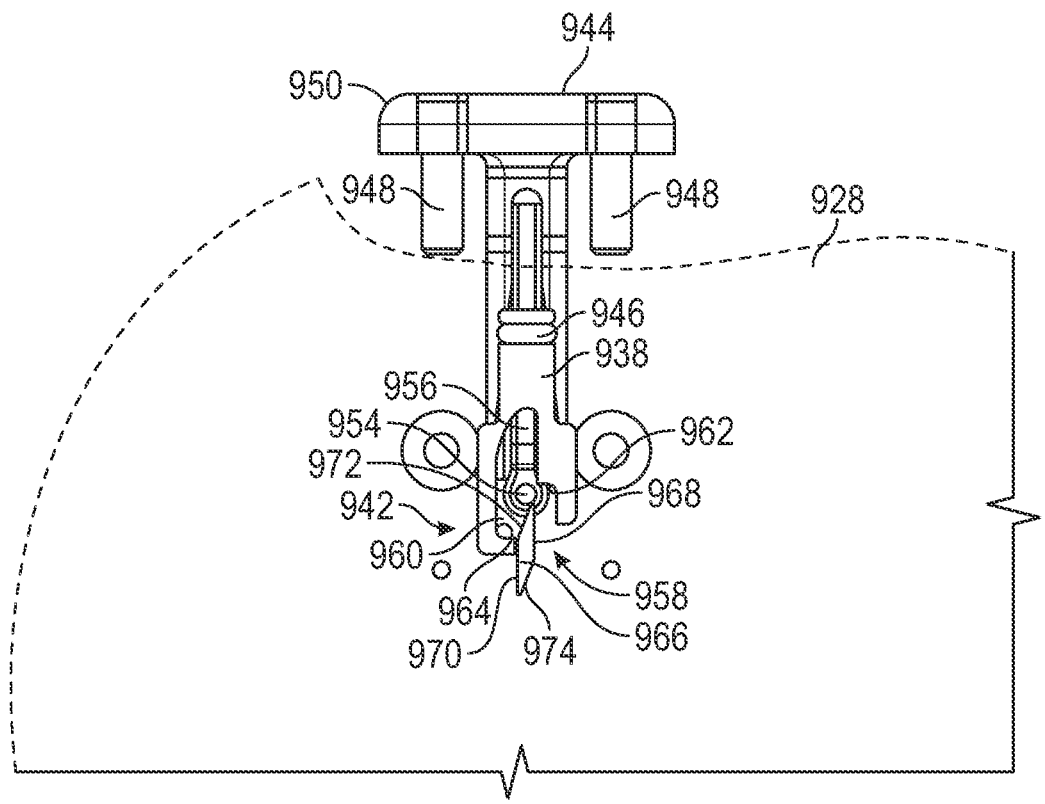
FIGS. 20D-20M depict a sequence of a bolus dose delivery system in accordance with one or more embodiments of the disclosure.
Figure 20E:
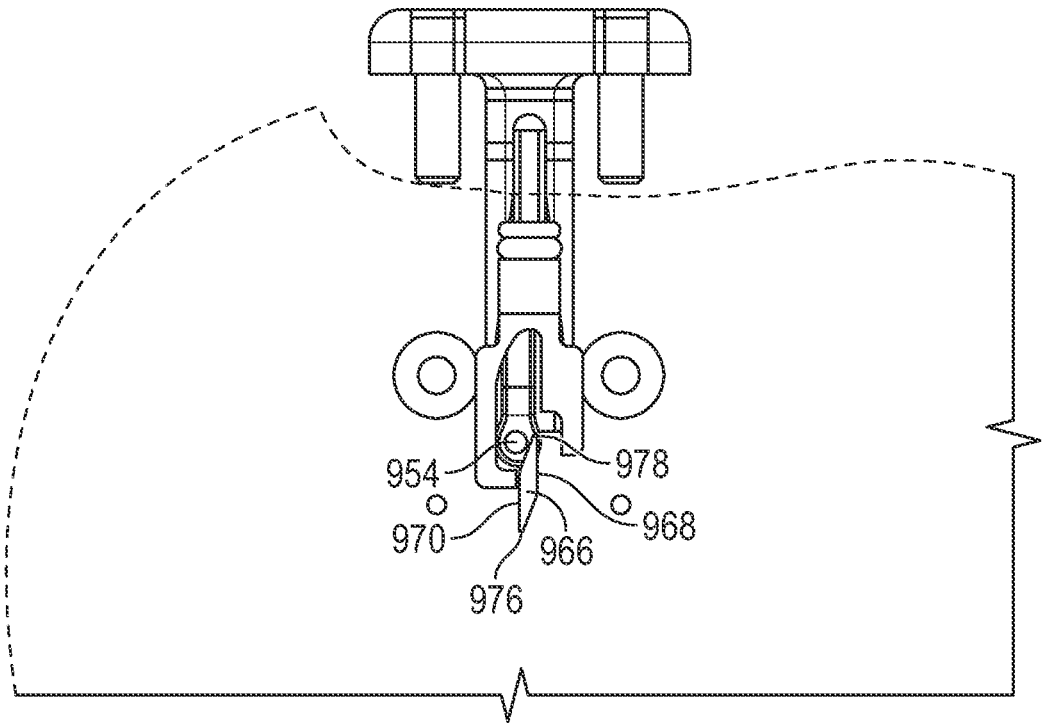
Figure 20F:
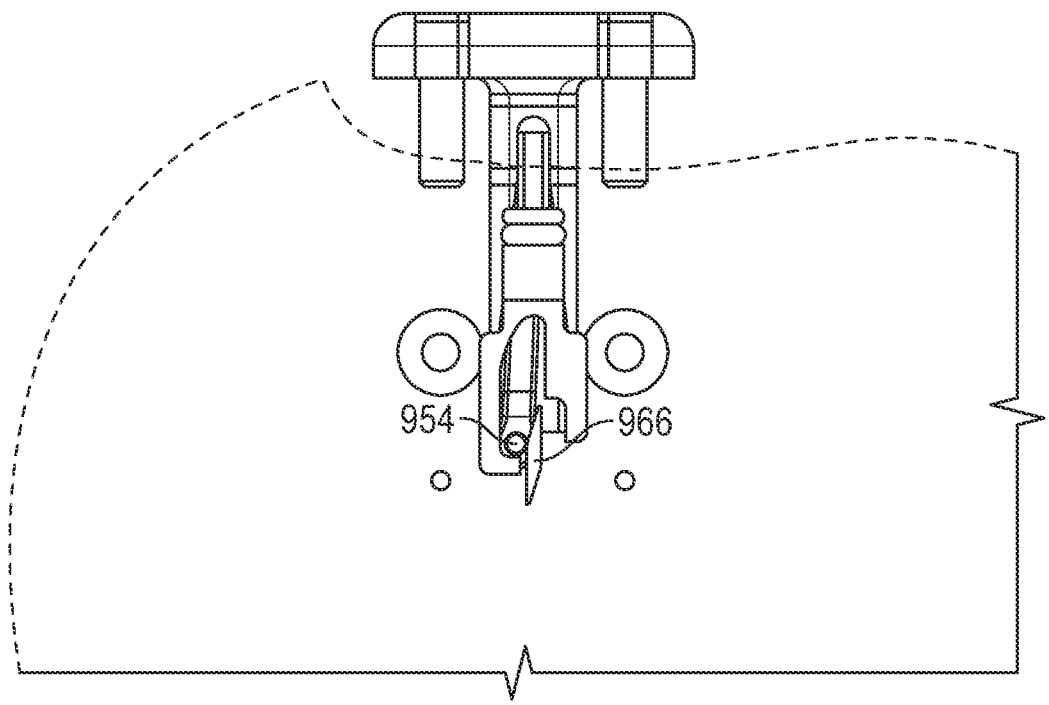
Figure 20G:
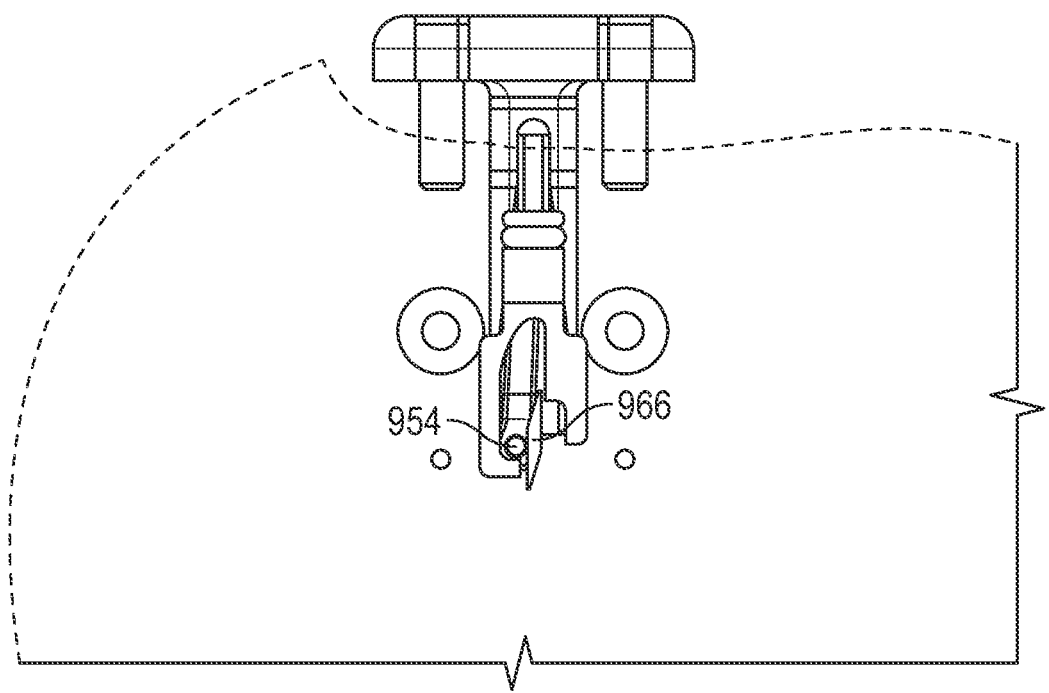
Figure 20H:
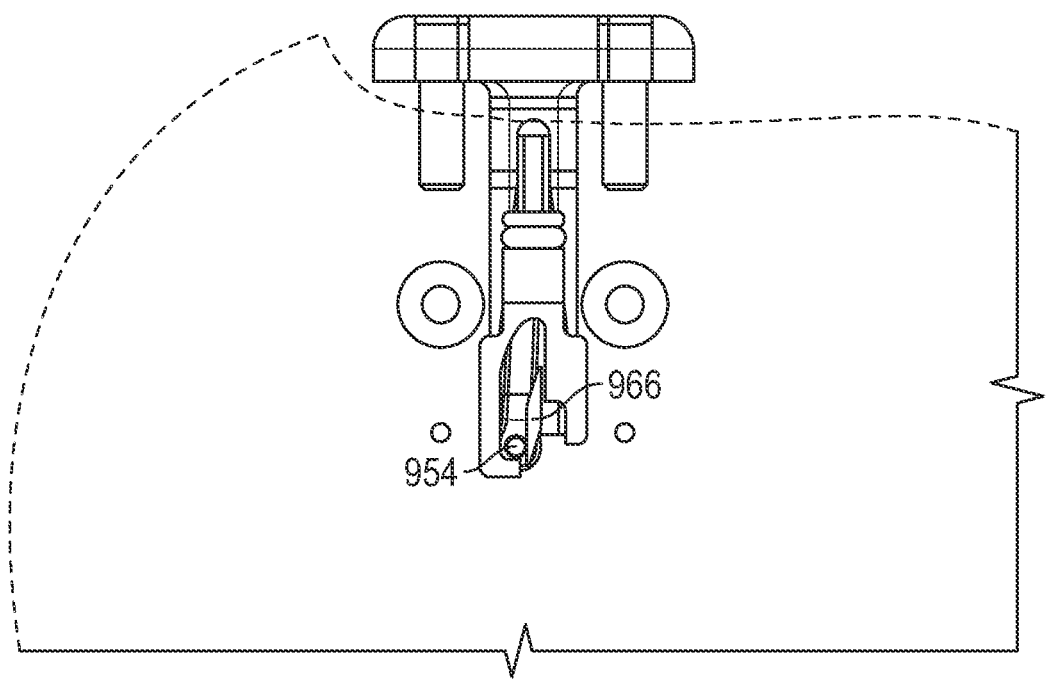
Figure 20I:
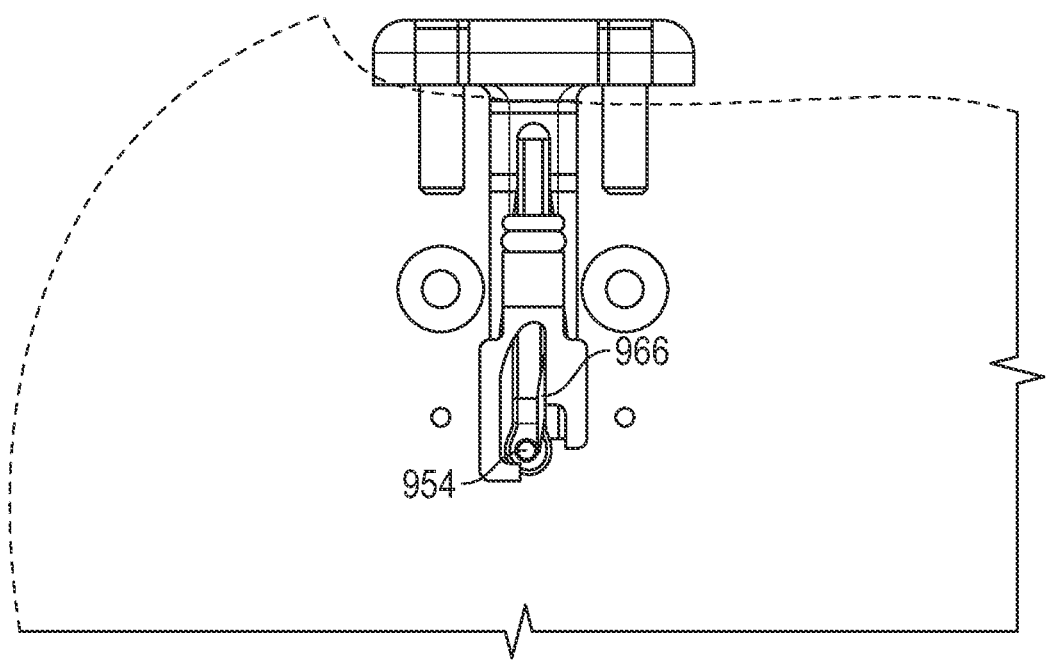
Figure 20J:
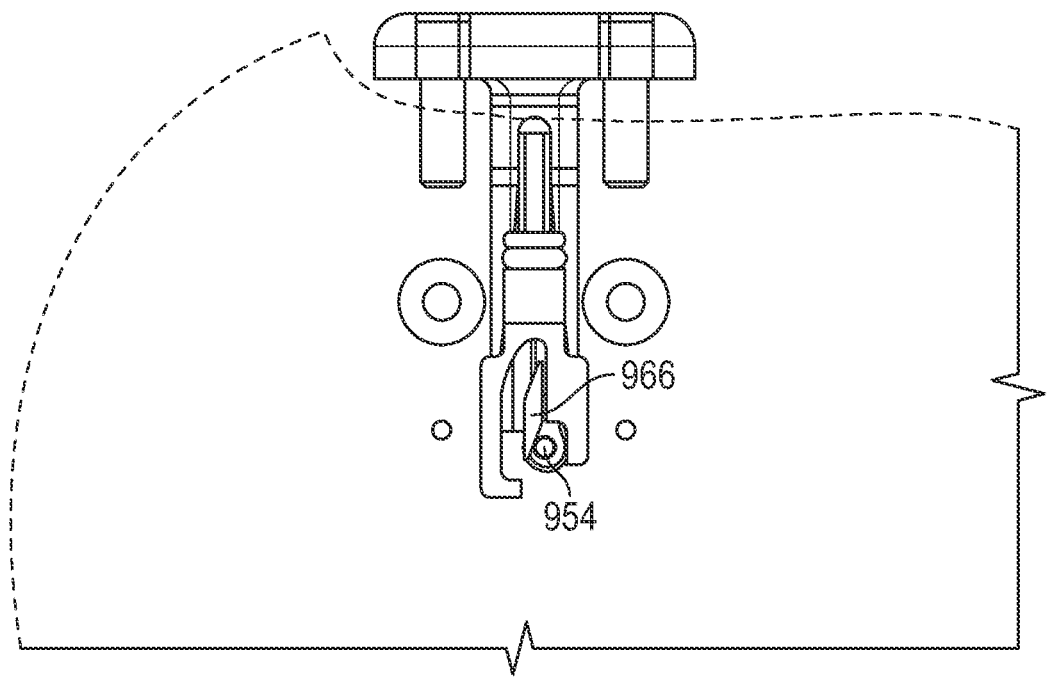
Figure 20K:
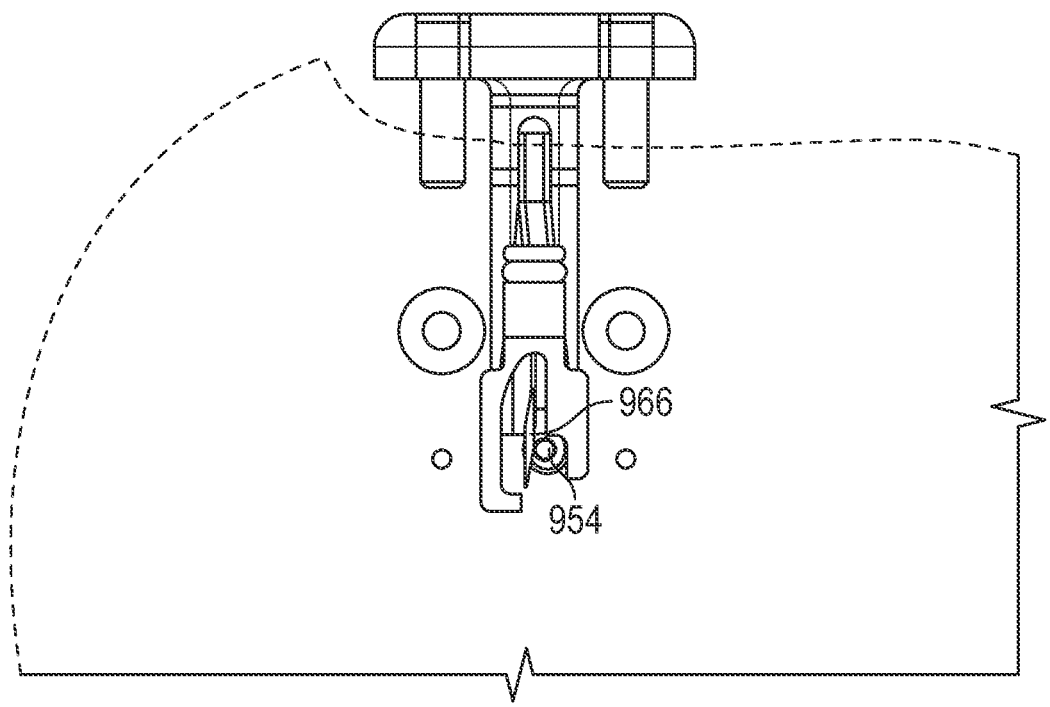
Figure 20L:
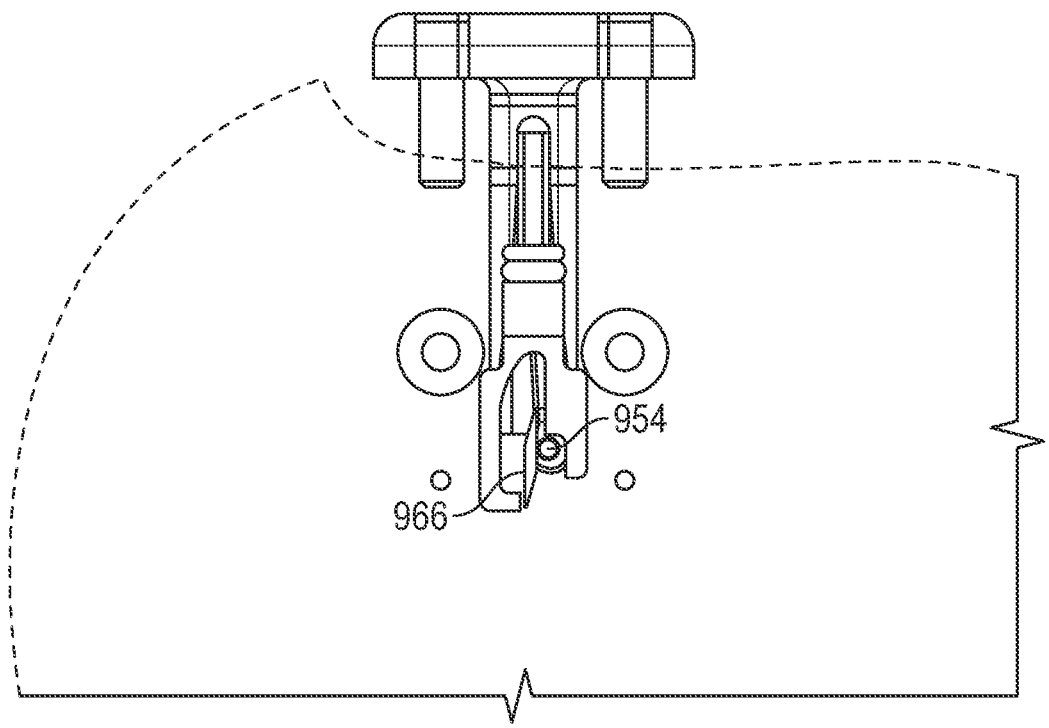
Figure 20M:
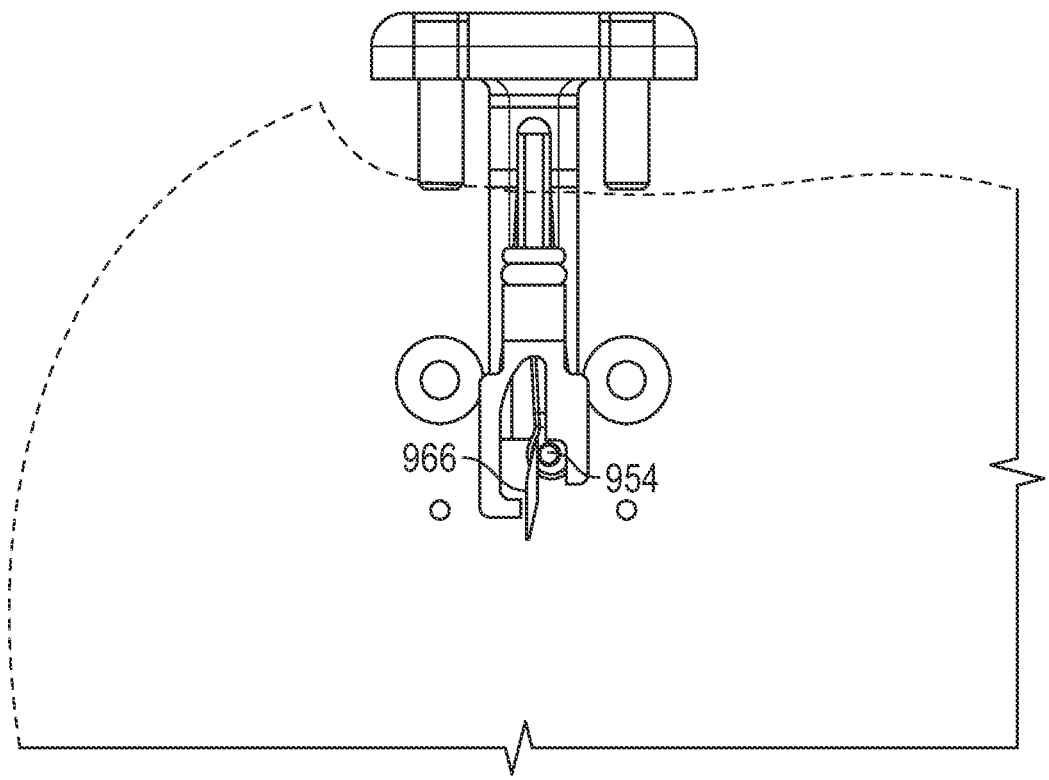

The bolus dose delivery system 900 is disposed along the bolus flow path 906. Generally speaking, the bolus dose delivery system 900 includes an inlet check valve 920, a piston pump 922, a first outlet check valve 924, and a second outlet check valve 926. The piston pump 922 is disposed between the inlet check valve 920 and the first outlet check valve 924. The first outlet check valve 924 and the second outlet check valve 926 are disposed in series along the bolus flow path 906. As depicted in FIGS. 19-20C, in some instances, the inlet check valve 920, the piston pump 922, the first outlet check valve 924, and the second outlet check valve 926 are disposed within a housing 928.

In some instances, the inlet check valve 920 comprises a duckbill valve, and the first outlet check valve 924 and the second outlet check valve 926 each comprise a PD valve. The inlet check valve 920, the first outlet check valve 924, and the second outlet check valve 926 may be any suitable check valve or the like.

In certain embodiments, the piston pump 922 comprises a bolus chamber 930. The bolus chamber 930 is formed within an enclosure 932 or the like. The enclosure 932 may be attached to or formed as part of the housing 928. In some instances, the size of the bolus chamber 930 corresponds to the bolus dose. In certain embodiments, the bolus chamber 930 accommodates 20 μl of fluid. The bolus chamber 930 may be any suitable size, shape, or configuration. The bolus chamber 930 includes an inlet 934 and an outlet 936.

The piston pump 922 also includes a piston 938 at least partially disposed within the bolus chamber 930. The piston 938 is moveable. For example, a first end 940 of the piston 938 is disposed within the bolus chamber 930, while a second end 942 of the piston 938 opposite the first end 940 is disposed outside of the bolus chamber 930. The second end 942 of the piston 938 may be in mechanical communication with a button 944. The button 944 is moveable. In this manner, as discussed in greater detail below, a user may engage (e.g., press and release) the button 944 in order to administer the bolus dose. To prevent leaks, the piston 938 includes one or more seals 946 (e.g., O-rings or the like) disposed about the first end 940 of the piston 938 within the bolus chamber 930. The seals 946 form a seal between the piston 938 and the bolus chamber 930. In this manner, the seals 946 prevent leaks from the bolus chamber 930 as the piston 938 moves between a first position (i.e., bolus dose dispensing position), as depicted in FIGS. 19 and 20, and a second position (i.e., bolus chamber filling position).

A spring 948 (or multiple springs) is disposed about the button 944 between a first end 950 of the button 944 and the enclosure 932. The spring 948 biases the button 944 in an extended position, which corresponds to the first position of the piston 938. A user therefore may press the first end 950 of the button 944 with enough force to overcome the spring force (resistance) of the spring 948 to depress the button 944 from the extended position, which in turn moves the piston 938 from the first position to the second position. In the second position, the bolus chamber 930 fills with the bolus dose via the inlet 934. Once the user releases the button 944, the spring 948 forces the button 944 back to the extended position, which in turn moves the piston 938 from the second position to the first position to administer the bolus dose to the cannula 918 via the outlet 936.

As depicted in FIG. 20D-20M, the piston pump 922 is configured to prevent partial dosing of the bolus dose. That is, in some instances, the button 944 must be fully depressed in order to move the piston 938 from the first position (FIG. 20D) to the second position (FIG. 20I) and back to the first position in order to fill the bolus chamber 930 with the bolus dose and thereafter administer the bolus dose to the cannula 918 via the outlet 936. Partial engagement of the button 944 will not fill the bolus chamber 930 with any medicament and thus partial dosing is prevented. That is, the button 944 must be fully depressed in order to align the inlet 934 in fluid communication with the bolus chamber 930 in order to fill the bolus chamber 930. For example, a second end 952 of the button 944 includes a protrusion 954 (or follower) attached to a resilient arm 956. The protrusion 954 may include a circular or elliptical cross-section. The protrusion 954 may be any suitable size, shape, or configuration. The protrusion 954 is in mechanical communication with the second end 942 of the piston 938. The second end 942 of the piston 938 includes a first channel 958 and a second channel 960. The first channel 958 ("the dispensing channel") corresponds to the bolus dose dispensing position, and the second channel 960 ("the fill channel") corresponds to the bolus chamber filling position. The first channel 958 includes a dispense lip 962, and the second channel 960 includes a fill lip 964. In this manner, the protrusion 954 moves between the first channel 958 and the second channel 960 to engage the fill lip 964 or the dispense lip 962 in order to fill the bolus chamber 930 and dispense the bolus dose.

A track 966 (or island) moves/guides the protrusion 954 between the first channel 958 and the second channel 960. For example, the track 966 includes a first side 968 and a second side 970. The second side 970 of the track 966 is configured to direct the protrusion 954 into the second channel 960 and against the fill lip 964 when the button 944 is depressed. That is, the second side 970 includes a cam surface 972 configured to direct the protrusion 954 into the second channel 960 and against the fill lip 964 when the button 944 is depressed. Conversely, the first side 968 of the track 966 is configured to direct the protrusion 954 into the first channel 958 and against the dispense lip 962 when the button 944 is released after being fully depressed. That is, the first side 968 includes a cam surface 974 configured to direct the protrusion 954 into the first channel 958 and against the dispense lip 962 when the button 944 is fully depressed and released. The track 966 may be any suitable size, shape, or configuration.

When the button 944 is depressed, the cam surface 972 on the second side 970 of the track 966 flexes the resilient arm 956 towards the second channel 960. In this manner, when the protrusion 954 reaches the distal end 976 of the track 966 (which corresponds to the button 944 being fully depressed), the resilient arm 956 moves the protrusion 954 from the second side 970 of the track 966 to the first side 968 of the track 966. Once on the first side 968 of the track 966, the cam surface 974 on the first side 968 of the track 966 flexes the resilient arm 956 towards the first channel 958. In this manner, when the protrusion 954 reaches the proximal end 978 of the track 966 (which corresponds to the button 944 being fully released back to the repose position via the spring 948), the resilient arm 956 moves the protrusion 954 from the first side 968 of the track 966 to the second side 970 of the track 966. As a result, in some instances, the protrusion 954 moves along an oval path during a stroke of the piston 938 as the button 944 is fully depressed and released. The protrusion 954 may move along any suitable path about the track 966 in a clockwise or counterclockwise manner. This process may be repeated as needed to deliver bolus doses to the user. The length of the first channel 958 and the second channel 960, as well as the location of the fill lip 964 and the dispense lip 962, at least partially dictate the piston stroke.

In order to prevent partial dosing, the bolus chamber 930 does not align with the inlet 934 until the protrusion 954 (in engagement with the fill lip 964) reaches the distal end 976 of the track 966, at which point the protrusion 954 moves from the second side 970 to the first side 968 of the track 966. Once on the first side 968 of the track 966, the protrusion 954 is directed against the dispense lip 962. The protrusion 954 then pushed the piston 938 (via the spring 948) from the second position to the first position in order to dispense a bolus dose. Because the bolus chamber 930 does not align with the inlet 934 until the protrusion 954 reaches the distal end 976 of the track 966, partial strokes of the button 944 will not result in any medicament entering the bolus chamber 930, and therefore no medicament will be delivered to the patient as the result of a partial stroke of the button 944.

In use, the bolus chamber 930 is filled with the bolus dose when the button 944 is depressed by the user. For example, a user can press the first end 950 of the button 944 to move the piston 938 from the first position to the second position. In this configuration, the bolus chamber is filled with the bolus dose via the inlet 934. Once the user releases the first end 950 of the button 944, the spring 948 biases the button 944 back to the extended position, which in turn moves the piston 938 from the second position to the first position. In this configuration, the pressure within the bolus chamber 930 is increased above the first outlet check valve 924 and the second outlet check valve 926 cracking pressure, allowing the bolus dose to flow from the bolus chamber 930 via the outlet 936 to the cannula 918. This process may be repeated as needed to deliver bolus doses to the user.

Figure 21:
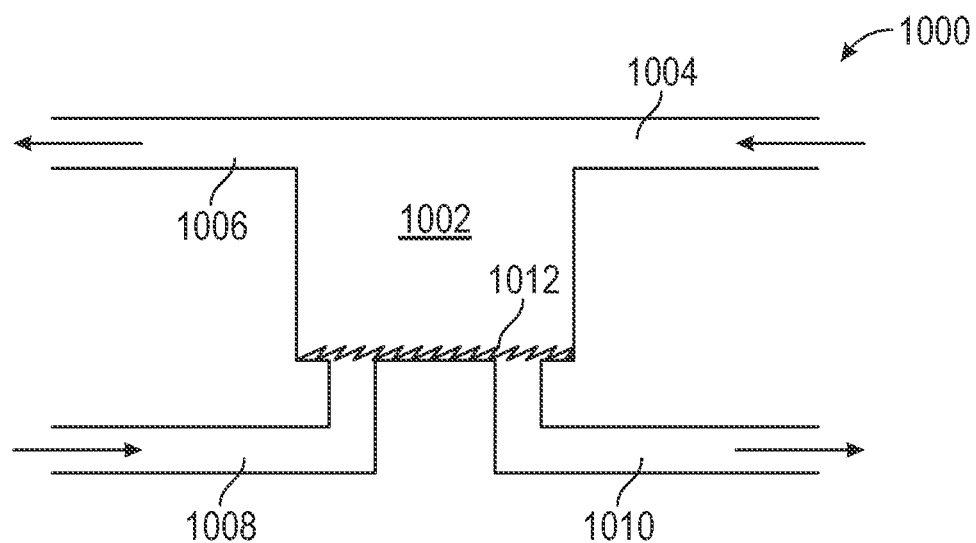
FIG. 21 depicts a self-sealing valve in accordance with one or more embodiments of the disclosure.

FIG. 21 depicts a valve 1000 that may be incorporated into any of the bolus dose delivery systems disclosed herein, particularly the bolus delivery system 900. The valve 1000 is a self-sealing valve. For example, the valve 1000 includes a chamber 1002 having an inlet 1004 from a supply line (e.g., the elastomeric bladder reservoirs described above), an outlet 1006 to a piston pump, an inlet 1008 from the piston pump, and an outlet 1010 to a cannula.

The chamber 1002 includes a flexible membrane 1012 disposed therein, which divides the chamber 1002 into two parts. The flexible membrane 1012 includes a first position and a second position. In the first position, the flexible membrane 1012 forms a seal between the inlet 1008 from the piston pump and the outlet 1010 to the cannula. The pressure within the chamber 1002 from the inlet 1004 of the supply line maintains the flexible membrane 1012 in the first position. An increase in pressure from the inlet 1008 from the piston pump above the pressure from the inlet 1004 from the supply line moves the flexible membrane 1012 from the first position to the second position. In the second position, fluid is able to flow from the inlet 1008 to the outlet 1010. In some instances, when in the second position, the flexible membrane 1012 can form a seal between the inlet 1004 and the outlet 1006. In other instances, the flexible membrane 1012 may not form a seal between the inlet 1004 and the outlet 1006 when in the second position. In such instances, a check valve or the like (not shown) may be positioned along the line to the piston pump after the outlet 1006 to the piston pump and before the inlet 1008 from the piston pump.

Figure 22:
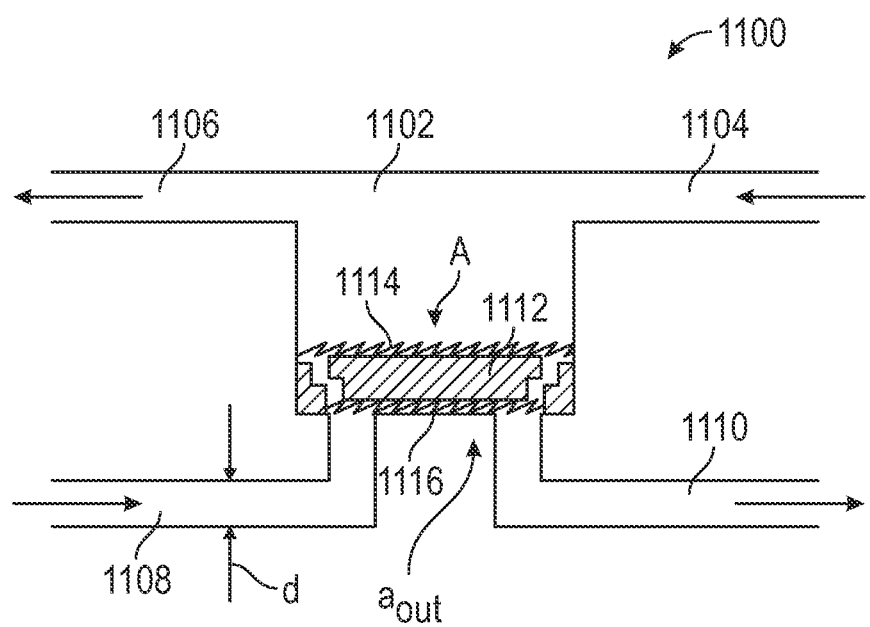
FIG. 22 depicts a pilot valve in accordance with one or more embodiments of the disclosure.

FIG. 22 depicts a pilot valve 1100 that may be incorporated into any of the bolus dose delivery systems disclosed herein, particularly the bolus delivery system 900. The pilot valve 1100 is similar to the pilot operated valve 326. For example, the pilot valve 1100 includes a chamber 1102 having an inlet 1104 from a supply line (e.g., the elastomeric bladder reservoirs described above), an outlet 1106 to a piston pump, an inlet 1108 from the piston pump, and an outlet 1110 to a cannula.

The chamber 1102 includes a valve 1112 moveably disposed between a first diaphragm 1114 and a second diaphragm 1116, which collectively divide the chamber 1102 into two parts. The pilot valve 1100 comprises a first position and a second position. In the first position, the pilot valve 1100 forms a seal between the inlet 1108 from the piston pump and the outlet 1110 to the cannula. The pressure within the chamber 1102 from the inlet 1104 line maintains the pilot valve 1100 in the first position. An increase in pressure from the inlet 1108 from the piston pump above the pressure from the inlet 1104 from the supply line moves the pilot valve 1100 from the first position to the second position. In the second position, fluid is able to flow from the inlet 1108 to the outlet 1110. In some instances, when in the second position, the pilot valve 1100 can form a seal between the inlet 1104 and the outlet 1106. In other instances, the pilot valve 1100 may not form a seal between the inlet 1104 and the outlet 1106 when in the second position. In such instances, a check valve or the like (not shown) may be positioned along the line to the piston pump after the outlet 1106 to the piston pump and before the inlet 1108 from the piston pump.

As the valve 1112 moves back and forth between the first position and the second position, the valve 1112 may push or release the first diaphragm 1114 and the second diaphragm 1116. For instance, the second diaphragm 1116 is configured to close (i.e., seal) the bolus flow path between the inlet 1108 and the outlet 1110 in the first position. At the same time, the first diaphragm 1114 will not obstruct the flow between the inlet 1104 and the outlet 1106 in the first position. Conversely, the first diaphragm 1114 is configured to close (i.e., seal) the bolus flow path between the inlet 1104 and the outlet 1106 in the second position. At the same time, the second diaphragm 1116 will not obstruct the flow between the inlet 1108 and the outlet 1110 in the first position. The pressures and geometries necessary to operate the valve 1100 may be determined as follows:

$$P_{close} = (P_{supply} * A)/a_{out}$$

$$P_{open} = (4P_{supply} * A)/(\Pi d^2)$$

FIGS. 29-32 depict a bolus dose delivery system 1400 having a combined piston pump and linear valve 1420, which operates in a similar manner to the combined piston pump and rotatable valve 420 depicted in FIGS. 13-16F. In the embodiment depicted in FIGS. 29-32, however, the valve moves in a linear direction instead of rotating. The combined piston pump and linear valve 1420 may be incorporated into any of the microfluidic circuits disclosed herein. For example, the combined piston pump and linear valve 1420 may be incorporated into a microfluidic circuits of a fluid medicament delivery device (e.g., an insulin pump or the like) configured to administer a medication in fluid form. The combined piston pump and linear valve 1420 may be incorporated into any suitable medicament delivery device.

The combined piston pump and linear valve 1420 includes a base 1422. The base 1422 includes a wall 1424 extending therefrom. In some instances, two walls 1424 extend from the base 1422. The base 1422 includes an inlet 1426 and an outlet 1428. The inlet 1426 and the outlet 1428 are in fluid communication with a bolus flow path. The base 1422 may be any suitable size, shape, or configuration.

A linear valve body 1430 is moveably disposed about the base 1422. In certain embodiments, the valve body 1430 is disposed at least partially between the walls 1424. In some instances, the valve body 1430 is disposed on tracks 1402 in the base 1422. That is, the valve body 1430 includes one or more protrusions 1404 disposed within and configured to slide along the tracks 1402. In this manner, the valve body 1430 can move a first direction 1432 or a second direction 1434 along the tracks 1402 between the walls 1424. The valve body 1430 includes a bolus chamber 1436 formed therein. In some instances, the size of the bolus chamber 1436 corresponds to the bolus dose. In certain embodiments, the bolus chamber 1436 accommodates 20 µl of fluid. The bolus chamber 1436 may be any suitable size, shape, or configuration. The bolus chamber 1436 includes an inlet 1438 and an outlet 1440 at a bottom end thereof. In some instances, the inlet 1438 and the outlet 1440 are one and the same. That is, the inlet 1438 and the outlet 1440 of the bolus chamber 1436 are relative depending on the status (i.e., filling or dispensing) of the bolus dose delivery system 1400. In some instances, the inlet 1426 of the base 1422 is in fluid communication with the inlet 1438 of the bolus chamber 1436 via a fill pocket 1421. In other instances, the outlet 1428 of the base 1422 is in fluid communication with outlet 1440 of the bolus chamber 1436 via a dose pocket 1423. To prevent leaks between the bolus chamber 1436 and the base 1422, seals 1442 are disposed about the inlet 1426 and the outlet 1428 of the base 422. The seals 1442 form the fill pocket 1421 and the dose pocket 1423. The valve body 1430 moves (e.g., linearly) about the seals 1442. Additional seals or structures may be disposed about the base 1422 to provide symmetry along the interface between the valve body 1430 and the base 1422.

The combined piston pump and linear valve 1420 includes a moveable piston 1444 at least partially disposed within the bolus chamber 1436 and in mechanical communication with (e.g., disposed within and in contact with) the valve body 1430. In some instances, the piston 1444 moves transverse to the linear movement of the valve body 1430. For example, a first end 1446 of the piston 1444 is disposed within the bolus chamber 1436, while a second end 1448 of the piston 1444 opposite the first end 1446 is disposed outside of the bolus chamber 1436 and comprises a protrusion 1450 (or follower pin) attached thereto and in mechanical communication with (e.g., contacting) the valve body 1430. In this manner, when the valve body 1430 moves linearly, the piston 1444 moves between a first position and a second position in order to administer the bolus dose. A piston spring is disposed about the piston 1444. The piston spring biases the piston 1444 in the first position.

To prevent leaks, the piston 1444 includes one or more seals 1456 (e.g., O-rings or the like) disposed about the first end 1446 of the piston 1444 within the bolus chamber 1436. The seals 1456 form a seal between the piston 1444 and the bolus chamber 1436. In this manner, the seals 1456 prevent leaks from the bolus chamber 1436 as the piston 1444 moves between the first position (i.e., bolus dose dispensing position) and the second position (i.e., bolus chamber filling position).

To move the piston 1444 from the first position to the second position, the valve body 1430 comprises a cam 1458. The cam 1458 may be any suitable size, shape, or configuration. In some instances, the cam 1458 is located on the walls 1424. The cam 1458 is configured to move the piston 1444 between the first position and the second position. In this manner, the cam 1458 transforms the linear movement of the valve body 1430 into linear movement of the piston 1444, which may be transverse to the linear movement of the valve body 1430. In some instances, the cam 1458 comprises a cutout 1460 having a cam surface 1462 in the wall 1424 of the valve body 430. The protrusion 1450 is disposed within the cutout 1460 and is in contact with the cam surface 1462.

In certain embodiments, the cam surface 1462 includes a first portion 1464, a second portion 1466, a third portion 1468, and a fourth portion 1470. The first portion 1464 may be substantially transverse to the linear movement of the piston 1444. In this manner, the first portion 1464 of the cam surface 1462 does not move the protrusion 1450 as the valve body 1430 moves. In some instances, the first portion 1464 of the cam surface 1462 may be omitted. The second portion 1466 of the cam surface 1462 is inclined relative to the first portion 1464 of the cam surface 1462. In this manner, the protrusion 1450 rides up the second portion 1466 of the cam surface 1462 as the valve body 430 moves in the first direction 1432, which causes the piston 1444 to move from the first position to the second position. The third portion 1468 of the cam surface 462 is located at an end of the second portion 1466 of the cam surface 1462 and is substantially parallel to the linear movement of the piston 1444. The fourth portion 1470 of the cam surface 1462 is located opposite the third portion 1468 and is substantially parallel to the linear movement of the piston 1444. As discussed below, the fourth portion 1470 of the cam surface 462 moves the piston 1444 from the second position to the first position.

To maintain the piston 1444 in the second position, the valve body 1430 includes a channel 1472 with a lip 1474. The protrusion 1450 is also located within the channel 1472. The channel 1472 is substantially parallel to the linear movement of the piston 1444. In some instances, the length of the channel 1472 corresponds to the second portion 1466 of the cam surface 1462. For example, the protrusion 1450 moves from a bottom of the channel 1472 to a top of the channel 1472 adjacent the lip 1474 as the protrusion 1450 rides up the second portion 1466 of the cam surface 462 during movement of the valve body 1430 in the first direction 1432. Similarly, the location of the lip 1474 corresponds to the third portion 1468 of the cam surface 1462. For example, the protrusion 1450 can move from the top of the channel 1472 and into the lip 1474 as the protrusion 450 is moved (e.g., pushed) by the third portion 1468 of the cam surface 1462 during movement of the valve body 1430 in the first direction 1432. When the protrusion 1450 is located within the lip 1474, the piston 1444 is "locked" in the second position.

The valve body 1430 can be moved in the first direction 1432 or the second direction 1434 via an actuator or the like in mechanical communication with the valve body 1430. The actuator may comprise a button or the like that a user pushes.

A valve spring is disposed about the valve body 1430. The valve spring biases the movement of the valve body 1430 in the second direction 1434. In this manner, to move the piston 1444 from the second position to the first position, the valve body 1430 moves in the second direction 1434, which causes the fourth portion 1470 of the cam surface 1462 to contact and move the protrusion 1450 out of the lip 1474 and back into the top of the channel 1472. The piston spring then forces the protrusion 1450 from the top of the channel 1472 to the bottom of the channel 1472, which in turn moves the piston 1444 from the second position to the first position. That is, the protrusion 1450 moves from the lip 1474 and into the top of the channel 1472 as the protrusion 1450 is pushed by the fourth portion 1470 of the cam surface 1462 during movement of the valve body 1430 in the second direction 1434. The combined piston pump and linear valve 1420 can include a plurality of protrusions 1450, a plurality of cams 1458, and a plurality of channels 1472.

In use, the bolus chamber 1436 is filled with the bolus dose when the piston 1444 is moved from the first position to the second position. In the first position, the inlet 1438 to the bolus chamber 1436 is blocked. That is, the inlet 1438 to the bolus chamber is not in fluid communication with the inlet 1426 of the base 1422. The actuator moves the valve body 1430 in the first direction 1432, which causes the protrusion 1450 to ride up the second portion 1466 of the cam surface 1462 from the bottom of the channel 1472 to the top of the channel 1472, which causes the piston 444 to move from the first position to the second position. The third portion 1468 of the cam surface 1462 then contacts the protrusion 1450 to push the piston 444 from the top of the channel 1472 and into the lip 1474 to "lock" the piston 1444 in the second position. In the second position, the inlet 1438 to the bolus chamber 1436 is disposed in fluid communication with the inlet 1426 of the base 1422, enabling the bolus chamber 1436 to be filled with the bolus dose. The valve body 1430 then moves in the second direction 434, which causes the fourth portion 1470 of the cam surface 1462 to contact and push the protrusion 1450 out of the lip 1474 and back into the top of the channel 1472. The piston spring then forces the protrusion 1450 from the top of the channel 1472 to the bottom of the channel 1472, which in turn moves the piston 1444 from the second position to the first position. At the same time (or very close thereto), the outlet 1440 of the bolus chamber 436 is in fluid communication with the outlet 1428 of the base 1422, which permits or enables transfer/flow of the bolus dose from the bolus chamber 436 to the cannula 418. This process may be repeated as needed to deliver bolus doses to the user.

In some instances, as the piston 1444 moves between the first position and the second position (or vice versa), the inlet 1438/outlet 1440 is located in the area between the fill pocket 1421 and the dose pocket 1423 as the valve body 1430 moves. In such instances, medicament may be released into a void 1425 between the valve body 1430 and the base 1422. The medicament located in the void 1425 between the valve body 1430 and the base 1422 is vented via a vent to a location outside of the combined piston pump and linear valve 1420 and away from the patient. That is, any medicament located in the void 1425 between the valve body 1430 and the base 1422 is not delivered to the patient.

The devices and methods described herein will be further understood by reference to the following non-limiting examples.

Examples

The bolus dose delivery systems disclosed herein were tested to determine the accuracy of the bolus dose being delivered by each device. During the test, the bolus dose volume was measured for 100 doses, and the dose variation for each device was determined. Each device was compared to a base line device, which corresponds to the bolus dose delivery system 136.

Figure 24:
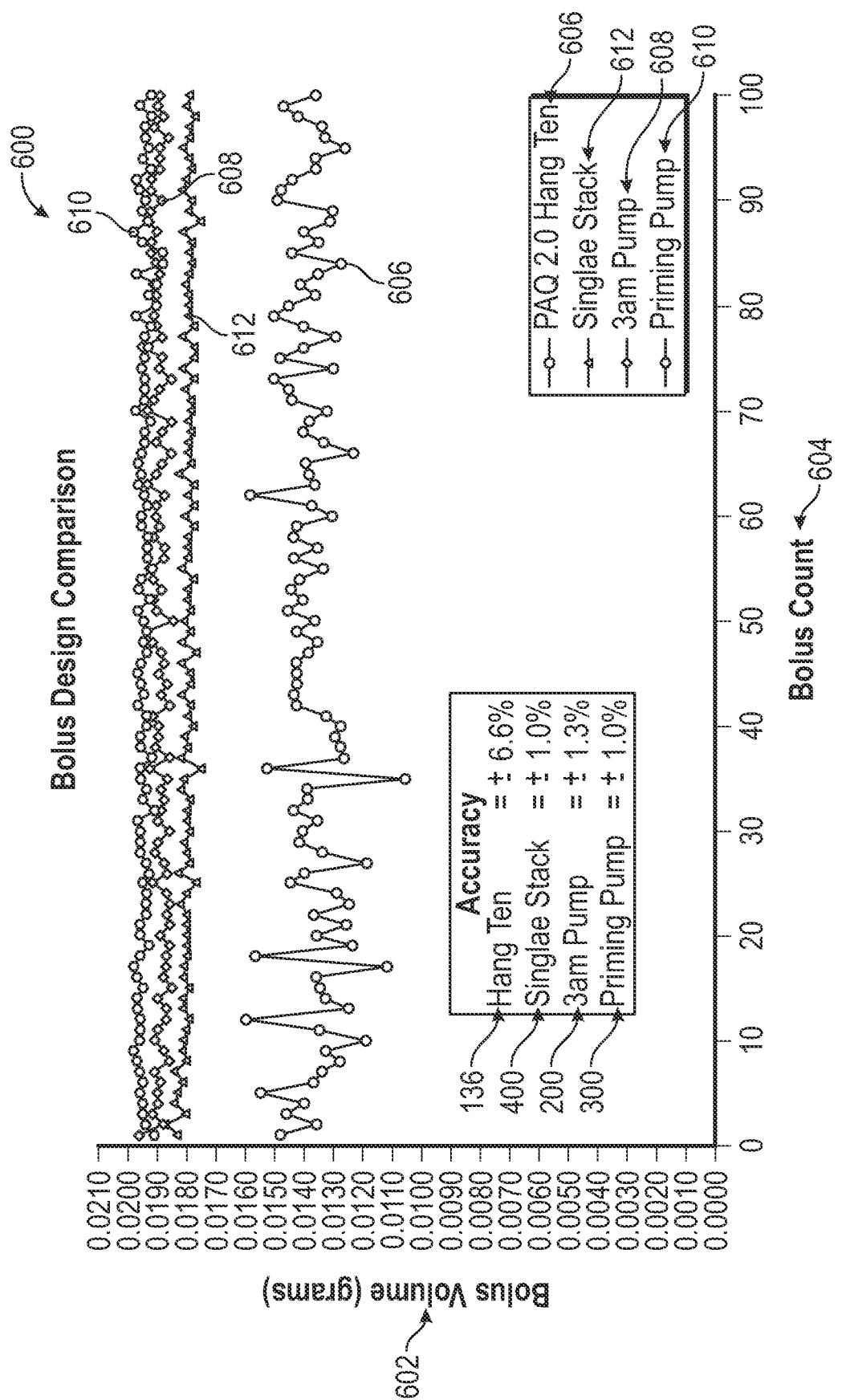
FIGS. 24-28 depict the bolus dose accuracy during testing of the various bolus dose delivery systems in accordance with various embodiments of the disclosure.

FIGS. 24-28 illustrate bolus dose accuracy during testing of the various systems and methods described herein. In particular, FIG. 24 depicts a graph 600 having the bolus dose volume 602 on the y-axis versus the bolus count 604 on the x-axis. The line 606 depicts the bolus dose delivery system 136, which includes an accuracy of +/−6.6%. The line 608 depicts the bolus dose delivery system 200, which includes an accuracy of +/−1.3%. The line 610 depicts the bolus dose delivery system 300, which includes an accuracy of +/−1.0%. The line 612 depicts the bolus dose delivery system 400, which includes an accuracy of +/−1.0%.

Figure 25:
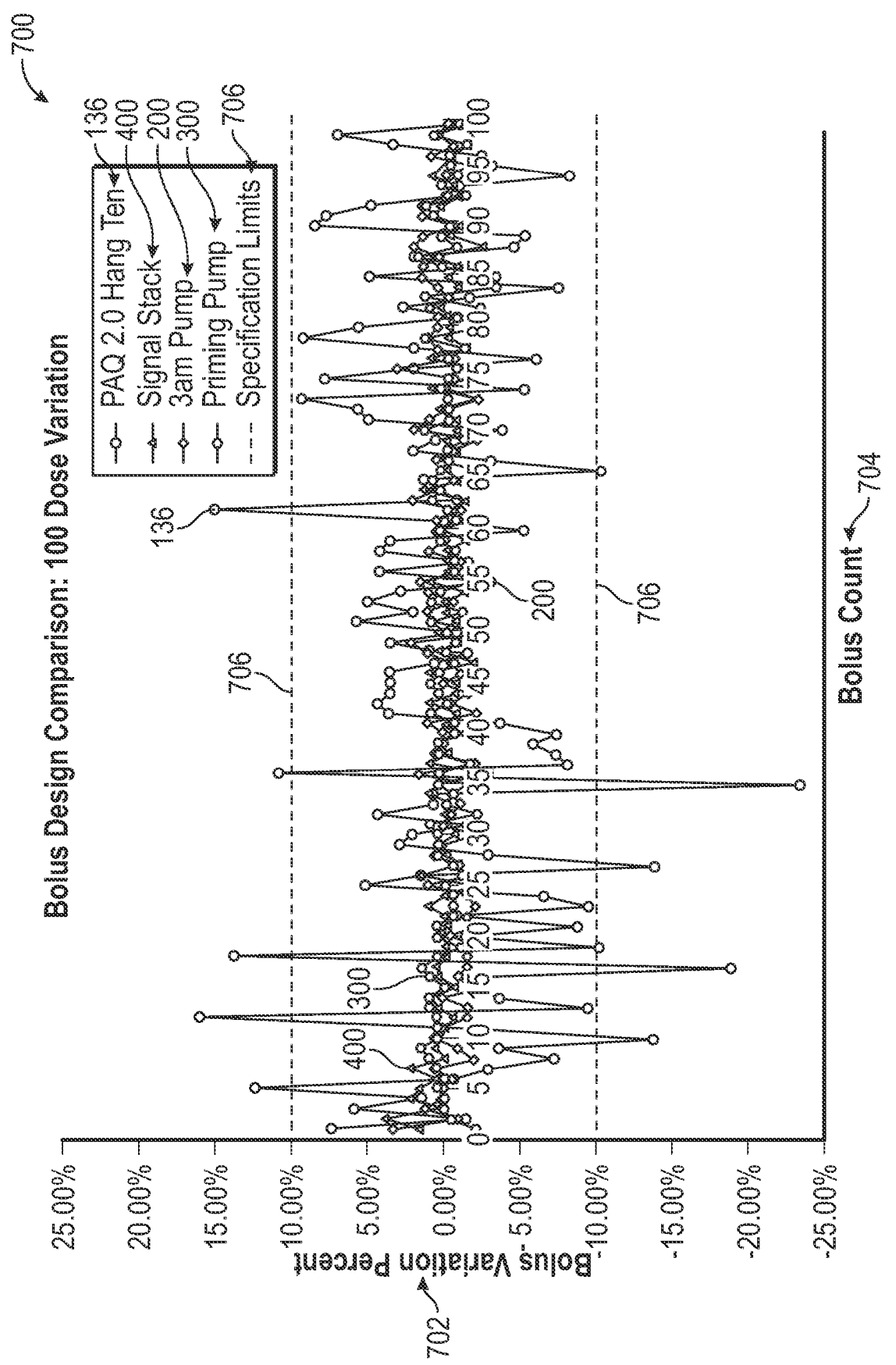

FIG. 25 depicts a graph 700 having the bolus dose variation percentage 702 on the y-axis versus the bolus count 704 on the x-axis. The performance of the bolus dose delivery system 200, the bolus dose delivery system 300, and the bolus dose delivery system 400 are all within the targeted +/−10% bolus dose volume variation margin 706. Indeed, each of the systems was within the ideal +/−5% bolus dose volume variation margin.

Figure 26:
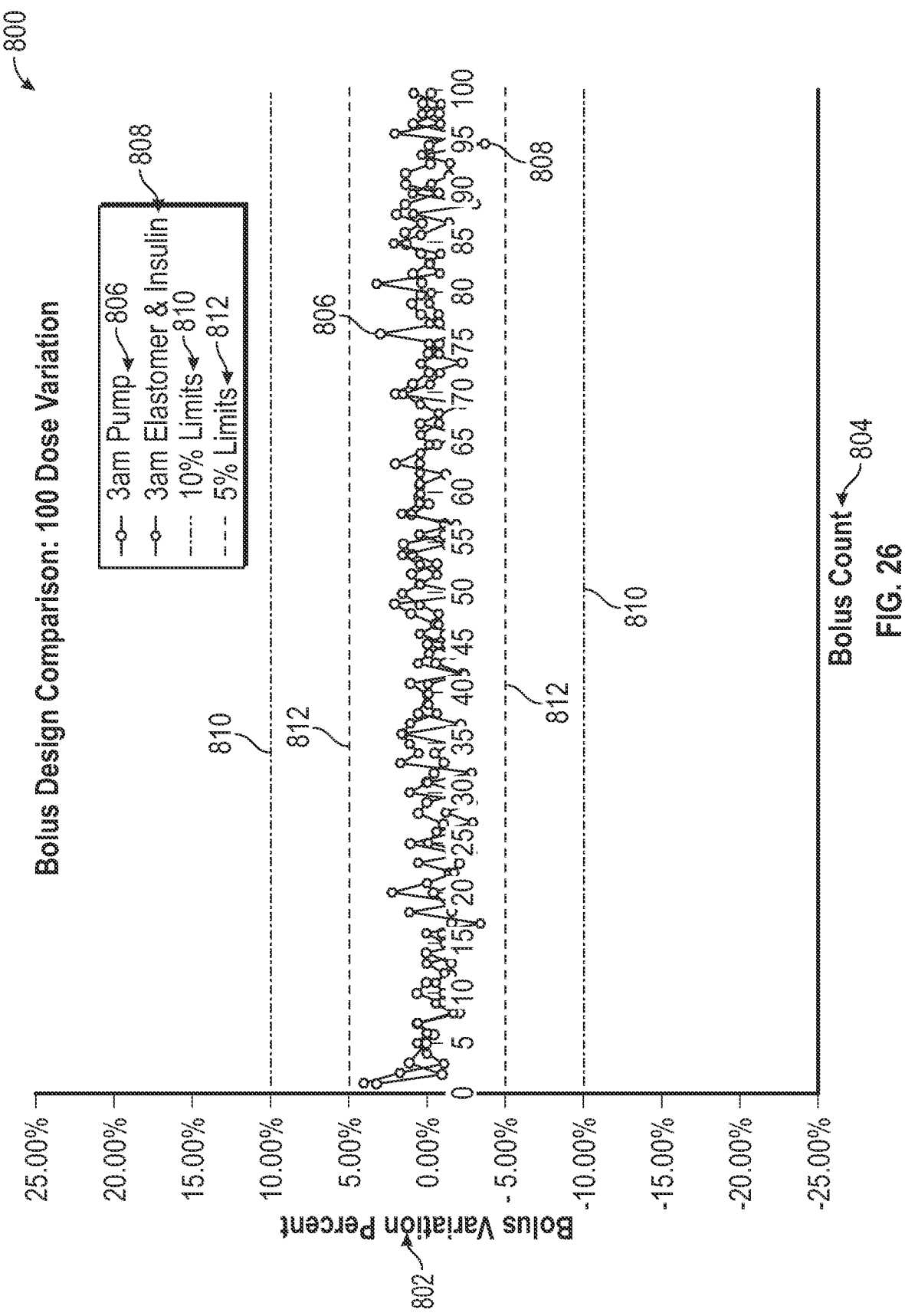

FIG. 26 depicts a graph 800 having the bolus dose variation percentage 802 on the y-axis versus the bolus count 804 on the x-axis for the bolus dose delivery system 200 using water and insulin. The line 806 depicts the bolus dose delivery system 200 using water as the fluid, and line 808 depicts the bolus dose delivery system 200 using insulin as the fluid. The performance of the bolus dose delivery system 200 for both water and insulin were within the targeted +/−10% bolus dose volume variation margin 810 and the ideal +/−5% bolus dose volume variation margin 812.

Figure 27:
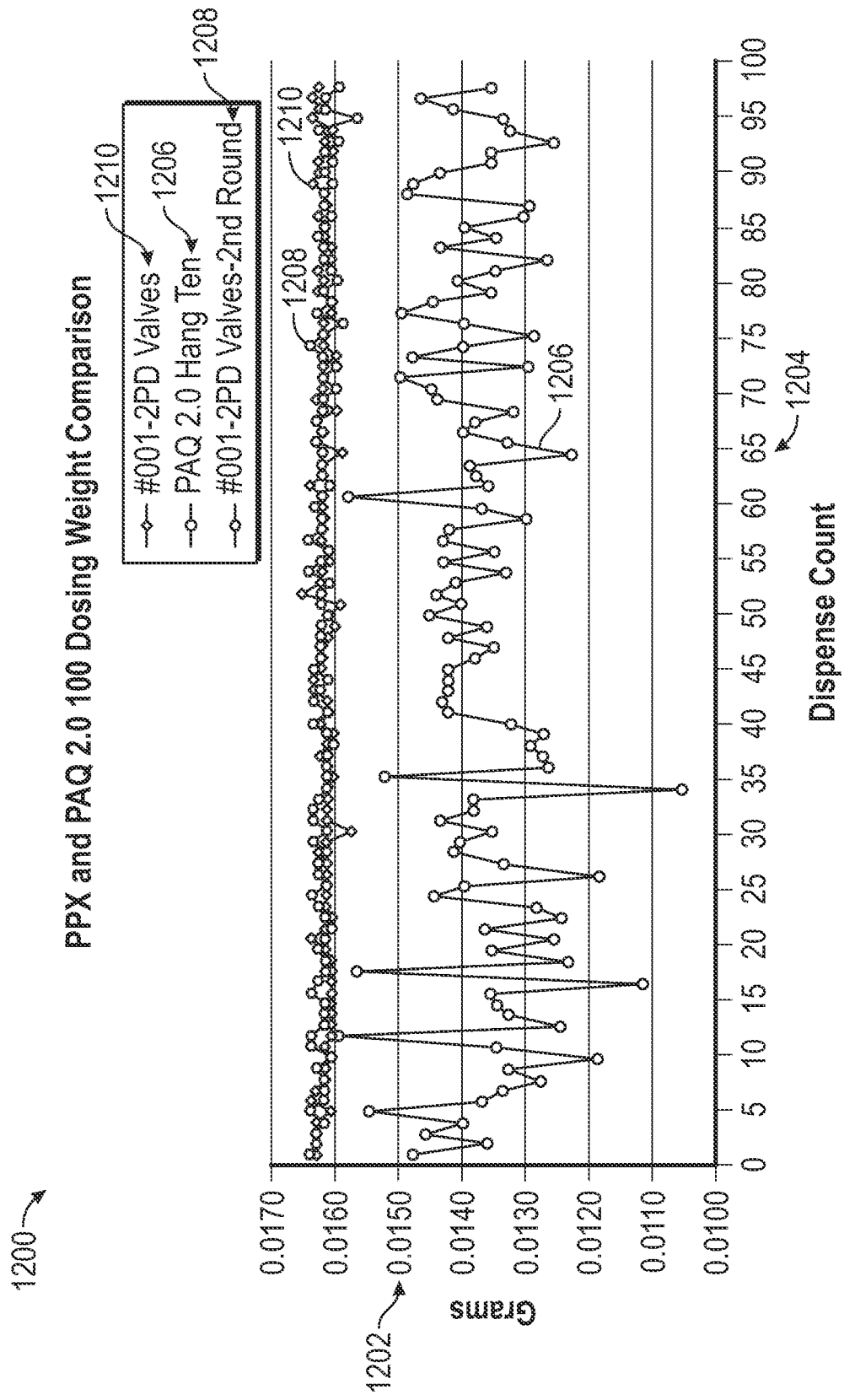

FIG. 27 depicts a graph 1200 having the bolus dose volume 1202 on the y-axis versus the bolus count 1204 on the x-axis. The line 1206 depicts the bolus dose delivery system 136, and the lines 1208 and 1210 depict two different test performed with the bolus dose delivery system 900.

Figure 28:
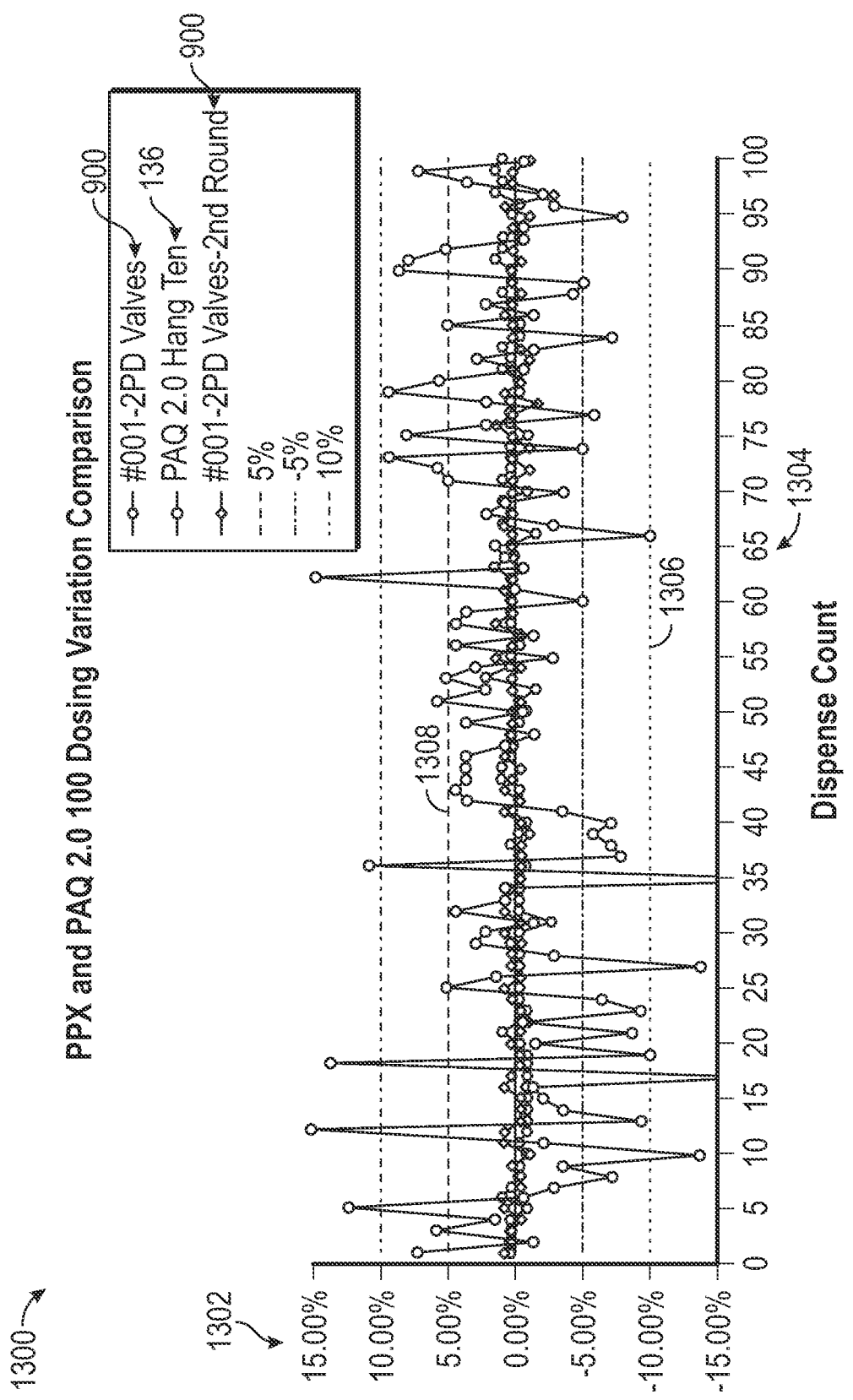
Figure 29:
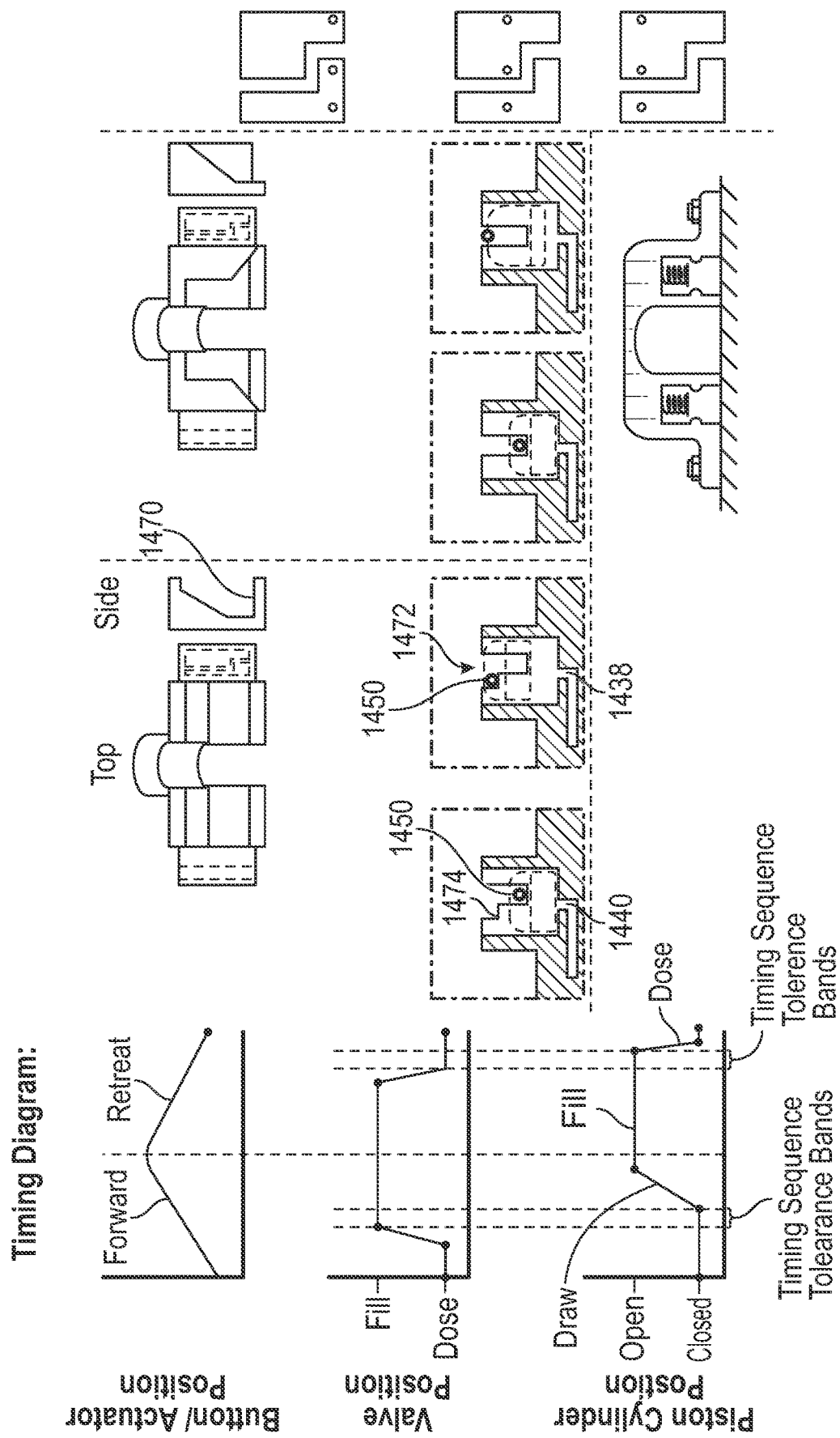
FIGS. 29-32 depict a bolus dose delivery system in accordance with one or more embodiments of the disclosure.
Figure 30:
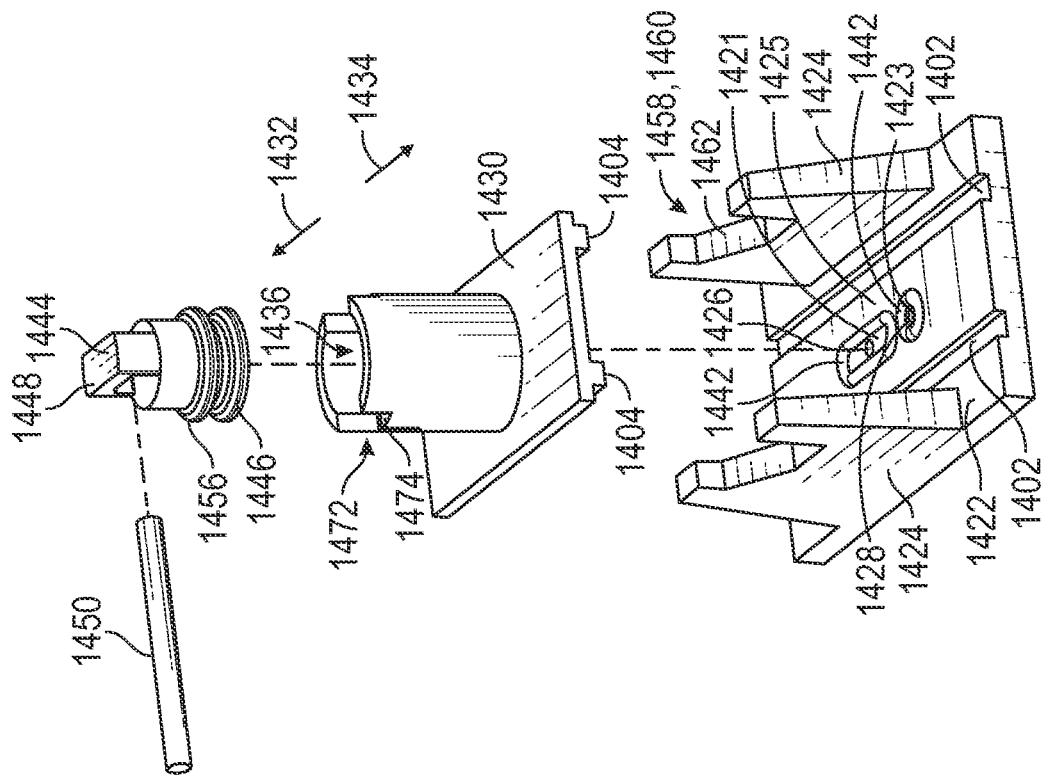
Figure 30:
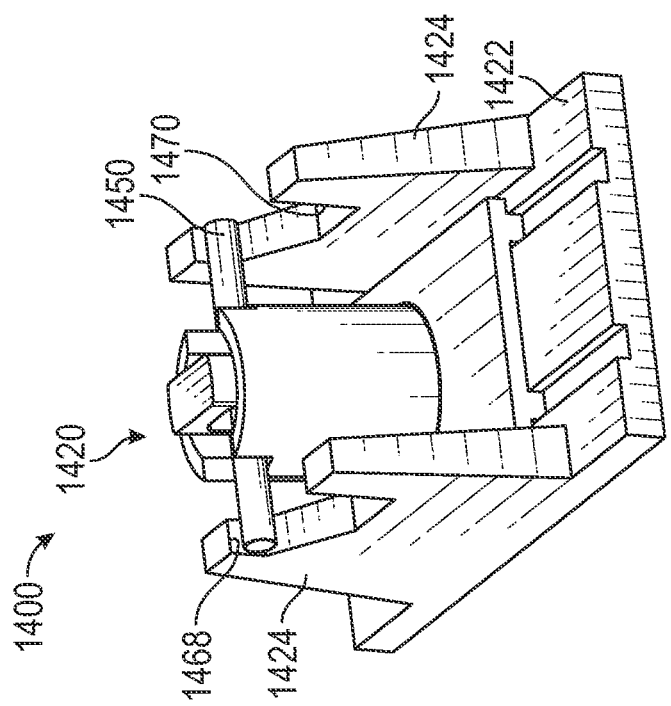
Figure 31:
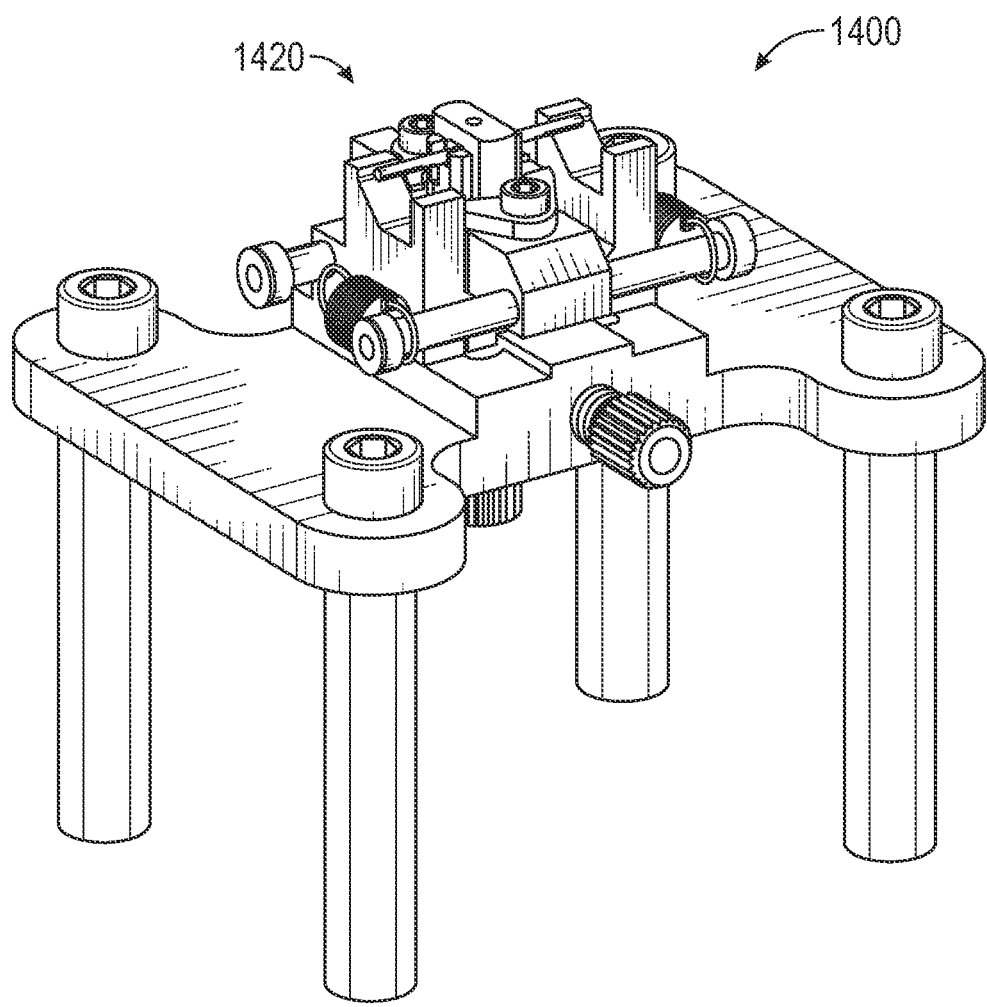
Figure 32:
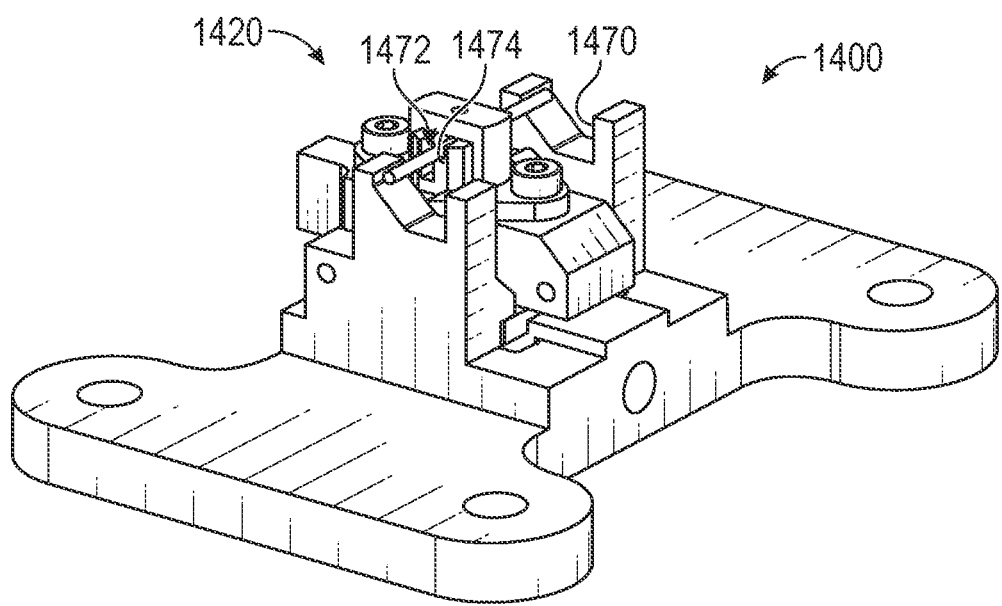

FIG. 28 depicts a graph 1300 having the bolus dose variation percentage 1302 on the y-axis versus the bolus count 1304 on the x-axis. The performance of the bolus dose delivery system 136 and the bolus dose delivery system 900 are both depicted. The performance of the bolus dose delivery system 900 in both test are within the targeted +/−10% bolus dose volume variation margin 1306. Indeed, each of the test of the bolus dose delivery system 900 was within the ideal +/−5% bolus dose volume variation margin 1308.

Exemplary Embodiments

Embodiment 1: A device for administering a medication in fluid form, the device comprising: a basal flow path; and a bolus flow path in parallel to the basal flow path, wherein the bolus flow path comprises a first valve, a second valve downstream of the first valve, and a piston pump disposed between the first valve and the second valve.

Embodiment 2: The device of Embodiment 1, wherein the piston pump comprises: a bolus chamber comprising an inlet and an outlet, wherein the first valve controls fluid flow into the inlet of the bolus chamber and the second valve controls fluid flow out of the outlet of the bolus chamber; a piston at least partially disposed within the bolus chamber, wherein the piston comprises a first position and a second position; and a latch comprising a latched position configured to secure the piston in the second position and an unlatched position configured to release the piston to the first position.

Embodiment 3: The device of Embodiment 2, wherein the piston pump comprises a button configured to open the first valve and close the second valve, or vice versa, and to move the latch between the latched position and the unlatched position.

Embodiment 4: The device of Embodiment 2 or 3, wherein the button comprises a first cam in mechanical communication with the first valve and the second valve, wherein movement of the button causes the first cam to open the first valve and close the second valve, or vice versa.

Embodiment 5: The device of Embodiment 3 or 4, wherein the button comprises a second cam in mechanical communication with the latch, wherein movement of the button causes the second cam to move the latch to the latched position.

Embodiment 6: The device of any one of Embodiments 3 to 5, wherein the button comprises a third cam in mechanical communication with the latch, wherein movement of the button causes the third cam to move the latch to the unlatched position.

Embodiment 7: The device of any one of Embodiments 1 to 6, wherein the first valve and the second valve each comprise an inlet, an outlet, a ball, a cam, and a diaphragm, wherein the ball is disposed between the cam and the diaphragm such that movement of the cam moves the ball against the diaphragm to open or close the inlet and the outlet of the first valve and the second valve.

Embodiment 8: The device of any one of Embodiments 1 to 7, further comprising: a fill port disposed upstream of the basal flow path and the bolus flow path; and a filter disposed upstream of the basal flow path and the bolus flow path.

Embodiment 9: The device of any one of Embodiments 1 to 8, further comprising a cannula disposed downstream of the basal flow path and the bolus flow path.

Embodiment 10: The device of any one of Embodiments 1 to 9, wherein the basal flow path comprises two flow restrictors in series.

Embodiment 11: The device of Embodiment 10, wherein the basal flow path comprises at least one pressure sensor disposed between the two flow restrictors.

Embodiment 12: A method for delivering a bolus dose in a microfluidic circuit of an insulin pump, the method comprising: opening a first valve; closing a second valve downstream of the first valve; moving a piston disposed at least partially within a bolus chamber disposed between the first valve and the second valve from a first position; latching the piston in a second position; filling the bolus chamber with the bolus dose; closing the first valve; opening the second valve; and releasing the piston from the second position to the first position to administer the bolus dose.

Embodiment 13: A device for administering a medication in fluid form, the device comprising: a basal flow path; and a bolus flow path in parallel to the basal flow path, wherein the bolus flow path comprises a first check valve, a second check valve downstream of the first check valve, a piston pump disposed between the first valve and the second valve, and a pilot operated valve in parallel to the piston pump.

Embodiment 14: The device of Embodiment 13, wherein the pilot operated valve comprises: a first position in which the bolus flow path is closed downstream of the piston pump and open upstream of the piston pump; and a second position in which the bolus flow path is open downstream of the piston pump and closed upstream of the piston pump.

Embodiment 15: The device of Embodiment 13 or 14, wherein the pilot operated valve comprises a valve disposed between a first diaphragm and a second diaphragm, wherein the first diaphragm closes the bolus flow path downstream of the piston pump in the first position, and wherein the second diaphragm closes the bolus flow path upstream of the piston pump in the second position.

Embodiment 16: The device of any one of Embodiments 13 to 15, wherein the first check valve comprises a duckbill valve.

Embodiment 17: The device of any one of Embodiments 13 to 16, wherein the second check valve comprises a PD valve.

Embodiment 18: The device of any one of Embodiments 13 to 17, wherein the piston pump comprises: a bolus chamber comprising an inlet and an outlet; a piston at least partially disposed within the bolus chamber, wherein the piston comprises a first position and a second position; and a spring disposed about the piston, wherein the spring biases the piston in the second position.

Embodiment 19: The device of Embodiment 18, wherein the piston pump comprises: a seal formed between the piston and the bolus chamber; and a pin stop disposed within a channel in the piston, wherein the pin stop is configured to limit a stroke of the piston.

Embodiment 20: The device of any one of Embodiments 13 to 19, further comprising: a fill port disposed upstream of the basal flow path and the bolus flow path; and a filter disposed upstream of the basal flow path and the bolus flow path.

Embodiment 21: The device of any one of Embodiments 13 to 20, further comprising a cannula disposed downstream of the basal flow path and the bolus flow path.

Embodiment 22: The device of any one of Embodiments 13 to 21, wherein the basal flow path comprises two flow restrictors in series.

Embodiment 23: The device of Embodiment 22, wherein the basal flow path comprises at least one pressure sensor disposed between the two flow restrictors.

Embodiment 24: A method for delivering a bolus dose in a microfluidic circuit of an insulin pump, the method comprising: filling a bolus chamber along a bolus flow path with the bolus dose; increasing a pressure within the bolus chamber by way of a piston disposed at least partially within the bolus chamber; and moving a pilot operated valve from a first position, in which the bolus flow path is closed downstream of the bolus chamber and open upstream of the bolus chamber, to a second position, in which the bolus flow path is open downstream of the bolus chamber and closed upstream of the bolus chamber.

Embodiment 25: A device for administering a medication in fluid form, the device comprising: a basal flow path; and a bolus flow path in parallel to the basal flow path, wherein the bolus flow path comprises a combined piston pump and rotatable valve.

Embodiment 26: The device of Embodiment 25, wherein the combined piston pump and rotatable valve comprise: a base comprising an inlet and an outlet; a rotatable valve body rotatably disposed about the base; a bolus chamber formed within the rotatable valve body, wherein the bolus chamber comprises an inlet and an outlet; a moveable and rotatable piston at least partially disposed within the bolus chamber and in mechanical communication with the rotatable valve body, wherein the moveable and rotatable piston comprises a first position and a second position; and a spring disposed about the moveable and rotatable piston, wherein the spring biases the moveable and rotatable piston in the first position.

Embodiment 27: The device of Embodiment 26, wherein the rotatable valve body comprises a cam configured to rotate and move the movable and rotatable piston from the first position to the second position.

Embodiment 28: The device of Embodiment 26 or 27, wherein the base comprises a channel having a lip configured to maintain the movable and rotatable piston in the second position.

Embodiment 29: The device of any one of Embodiments 26 to 28, further comprising an actuator in mechanical communication with the rotatable valve body.

Embodiment 30: The device of any one of Embodiments 26 to 29, further comprising an inlet seal disposed about the base to form a fill pocket about the inlet of the bolus chamber; an outlet seal disposed about the base to form a dose pocket about the outlet of the bolus chamber; and a vent disposed in the base, wherein as the moveable and rotatable piston moves between the first position and the second position, the inlet and/or outlet of the bolus chamber is located between the fill pocket and the dose pocket such that medicament released into a void between the rotatable valve body and the base is vented via the vent to a location outside of the combined piston pump and rotatable valve and away from a patient.

Embodiment 31: The device of any one of Embodiments 26 to 30, further comprising a valve spring in mechanical communication with the rotatable valve body.

Embodiment 32: A method for delivering a bolus dose in a microfluidic circuit of an insulin pump, the method comprising: rotating, in a first direction, a rotatable valve body comprising a bolus chamber formed therein; moving a moveable and rotatable piston at least partially disposed within the bolus chamber and in mechanical communication with the rotatable valve body; filling the bolus chamber with the bolus dose; rotating, in a second direction, the rotatable valve body; and releasing the moveable and rotatable piston to administer the bolus dose.

Embodiment 33: A device for administering a medication in fluid form, the device comprising: a basal flow path; and a bolus flow path in parallel to the basal flow path, wherein the bolus flow path comprises a first valve set, a second valve set, a bolus chamber, and a flexible membrane disposed within the bolus chamber, wherein the flexible membrane is configured to force the medication from the bolus chamber due to opening and closing of the first valve set and the second valve set.

Embodiment 34: The device of Embodiment 33, wherein the first valve set comprises a first valve and a second valve and the second valve set comprises a third valve and a fourth valve.

Embodiment 35: The device of Embodiment 33 or 34, wherein the bolus flow path comprises a first flow path and a second flow path in parallel.

Embodiment 36: The device of any one of Embodiments 33 to 35, wherein the bolus chamber is disposed between the first flow path and the second flow path.

Embodiment 37: The device of any one of Embodiments 33 to 36, wherein the first valve is disposed along the first flow path upstream of the bolus chamber and the second valve is disposed along the second flow path downstream of the bolus chamber.

Embodiment 38: The device of any one of Embodiments 33 to 37, wherein the third valve is disposed along the second flow path upstream of the bolus chamber and the fourth valve is disposed along the first flow path downstream of the bolus chamber.

Embodiment 39: The device of any one of Embodiments 33 to 38, wherein when the first valve and the second valve are open, the third valve and the fourth valve are closed, and wherein when the third valve and the fourth valve are open, the first valve and the second valve are closed.

Embodiment 40: A method for delivering a bolus dose in a microfluidic circuit of an insulin pump, wherein the bolus dose is disposed within a first portion or a second portion of a bolus chamber divided by a flexible membrane, the method comprising: closing a first set of valves; opening a second set of valves; dispensing the bolus dose disposed within the first portion of the bolus chamber; and filling the second portion of the bolus chamber with the bolus dose.

Embodiment 41: The method of Embodiment 40, further comprising simultaneously carrying out the dispensing and filling steps.

Embodiment 42: A device for administering a medication in fluid form, the device comprising: a basal flow path; and a bolus flow path in parallel to the basal flow path, wherein the bolus flow path comprises an inlet check valve, a first outlet check valve downstream of the inlet check valve, and a piston pump disposed between the inlet check valve and the first outlet check valve, wherein the piston pump is configured to prevent partial dosing of a bolus dose.

Embodiment 43: The device of Embodiment 42, wherein the piston pump comprises: a button comprising a resilient arm attached to a protrusion; a piston in mechanical communication with the protrusion, wherein the piston comprises a first channel having a dispensing lip and a second channel having a filling lip, wherein the protrusion is configured to move between the first channel and the second channel to engage the fill lip or the dispense lip; and a track configured to move the protrusion between the first channel and the second channel.

Embodiment 44: The device of Embodiment 42 or 43, wherein the piston pump comprises: a bolus chamber comprising an inlet and an outlet; wherein the piston is at least partially disposed within the bolus chamber, wherein the piston comprises a first position and a second position; and a spring disposed about the button, wherein the spring biases the button in an extended position, which corresponds to the first position of the piston.

Embodiment 45: The device of any one of Embodiments 42 to 44, wherein when the button is depressed, the track flexes the resilient arm towards the second channel, and wherein when the protrusion reaches a distal end of the track, the resilient arm and track move the protrusion towards the first channel.

Embodiment 46: The device of any one of Embodiments 42 to 45, wherein the bolus chamber does not align with the inlet until the protrusion reaches the distal end of the track, at which point the protrusion is directed against the dispense lip, wherein the protrusion pushed the piston via the spring in order to dispense a bolus dose.

Embodiment 47: The device of any one of Embodiments 42 to 46, further comprising a second outlet check valve in series with and downstream of the first outlet check valve.

Embodiment 48: The device of any one of Embodiments 42 to 47, wherein the inlet check valve comprises a duckbill valve.

Embodiment 49: The device of any one of Embodiments 42 to 48, wherein the first outlet check valve and the second outlet check valve comprise PD valves.

Embodiment 50: The device of any one of Embodiments 42 to 49, wherein the piston pump comprises a seal formed between the piston and the bolus chamber.

Embodiment 51: The device of any one of Embodiments 42 to 50, further comprising: a fill port disposed upstream of the basal flow path and the bolus flow path; and a filter disposed upstream of the basal flow path and the bolus flow path.

Embodiment 52: The device of any one of Embodiments 42 to 51, further comprising a cannula disposed downstream of the basal flow path and the bolus flow path.

Embodiment 53: The device of any one of Embodiments 42 to 52, wherein the basal flow path comprises two flow restrictors in series.

Embodiment 54: The device of Embodiment 53, wherein the basal flow path comprises at least one pressure sensor disposed between the two flow restrictors.

Embodiment 55: A method for delivering a bolus dose in a microfluidic circuit of an insulin pump, the method comprising: depressing a button to move a piston disposed at least partially within a bolus chamber from a first position to a second position to fill the bolus chamber with the bolus dose; and releasing the button to move the piston disposed at least partially within the bolus chamber from the second position to the first position to increase a pressure within the bolus chamber by way of the piston disposed at least partially within the bolus chamber.

Embodiment 56: The device or method of any one of Embodiments 1 to 55, further comprising a pilot operated valve disposed along the bolus flow path.

Embodiment 57: The device or method of any one of Embodiments 1 to 56, further comprising a self-sealing valve disposed along the bolus flow path.

Embodiment 58: A device for administering a medication in fluid form, the device comprising: a basal flow path; and a bolus flow path in parallel to the basal flow path, wherein the bolus flow path comprises a combined piston pump and linear valve.

Embodiment 59: The device of claim 58, wherein the combined piston pump and linear valve comprises: a base comprising an inlet and an outlet; a linearly moveable valve body disposed about the base; a bolus chamber formed within the valve body, wherein the bolus chamber comprises an inlet and an outlet; a moveable piston at least partially disposed within the bolus chamber and in mechanical communication with the valve body, wherein the moveable piston comprises a first position and a second position.

Embodiment 60: The device of Embodiment 58 or 59, wherein the valve body comprises a cam configured to move the movable piston from the first position to the second position.

Embodiment 61: The device of any one of Embodiments 58 to 60, wherein the valve body comprises a channel having a lip configured to maintain the movable piston in the second position.

Embodiment 62: The device of any one of Embodiments 58 to 61, further comprising an inlet seal disposed about the base to form a fill pocket about the inlet of the bolus chamber; an outlet seal disposed about the base to form a dose pocket about the outlet of the bolus chamber; and a vent disposed in the base, wherein as the moveable and rotatable piston moves between the first position and the second position, the inlet and/or outlet of the bolus chamber is located between the fill pocket and the dose pocket such that medicament released into a void between the valve body and the base is vented via the vent to a location outside of the combined piston pump and linear valve and away from a patient.

Embodiment 63: A method for delivering a bolus dose in a microfluidic circuit of an insulin pump, the method comprising: moving, in a first direction, a valve body comprising a bolus chamber formed therein; moving a piston at least partially disposed within the bolus chamber and in mechanical communication with the valve body; filling the bolus chamber with the bolus dose; moving, in a second direction, the valve body; and releasing the piston to administer the bolus dose.

Embodiment 64: The device or method of any one of Embodiments 1 to 63, wherein the device is configured to deliver a bolus dose which has a volume variation that is within ±10% or within ±5% of a targeted bolus dose volume, e.g., 20 µl of a liquid, e.g., insulin.

Modifications and variations of the methods and devices described herein will be obvious to those skilled in the art from the foregoing detailed description. Such modifications and variations are intended to come within the scope of the appended claims.

We claim:

1. A device for administering a medication in fluid form, the device comprising:
    a basal flow path; and
    a bolus flow path in parallel to the basal flow path, wherein the bolus flow path comprises a combined piston pump and rotatable valve, wherein the combined piston pump and rotatable valve comprises:
        a base comprising an inlet and an outlet;
        a rotatable valve body rotatably disposed about the base;
        a bolus chamber formed within the rotatable valve body, wherein the bolus chamber comprises an inlet and an outlet;
        a moveable and rotatable piston at least partially disposed within the bolus chamber and in mechanical communication with the rotatable valve body, wherein the moveable and rotatable piston comprises a first position and a second position;
        a spring disposed about the moveable and rotatable piston, wherein the spring biases the moveable and rotatable piston in the first position;
        an inlet seal disposed about the base to form a fill pocket about the inlet of the bolus chamber;
        an outlet seal disposed about the base to form a dose pocket about the outlet of the bolus chamber; and
        a vent disposed in the base,
        wherein as the moveable and rotatable piston moves between the first position and the second position, the inlet and/or outlet of the bolus chamber is located between the fill pocket and the dose pocket such that medicament released into a void between the rotatable valve body and the base is vented via the vent to a location outside of the combined piston pump and rotatable valve and away from a patient.

2. The device of claim 1, wherein the rotatable valve body comprises a cam configured to rotate and move the movable and rotatable piston from the first position to the second position.

3. The device of claim 2, wherein the base comprises a channel having a lip configured to maintain the movable and rotatable piston in the second position.

4. The device of claim 1, further comprising an actuator in mechanical communication with the rotatable valve body.

5. The device of claim 1, further comprising a valve spring in mechanical communication with the rotatable valve body.

6. The device of claim 1, further comprising:
    a fill port disposed upstream of the basal flow path and the bolus flow path; and
    a filter disposed upstream of the basal flow path and the bolus flow path.

7. The device of claim 1, further comprising a cannula disposed downstream of the basal flow path and the bolus flow path.

8. The device of claim 1, wherein the basal flow path comprises two flow restrictors in series.

9. The device of claim 8, wherein the basal flow path comprises at least one pressure sensor disposed between the two flow restrictors.

10. The device of claim 1, which is part of a wearable patch pump for administering insulin to a patient.

11. The device of claim 1, wherein the device is configured to deliver a bolus dose which has a volume variation that is within ±10% of a targeted bolus dose volume.

12. A device for administering a bolus dose of a medication to a patient, the device comprising:
    a bolus flow path; and
    a combined piston pump and rotatable valve disposed along the bolus flow path and configured to prevent partial dosing of a bolus dose, wherein the combined piston pump and rotatable valve comprises
        a base comprising an inlet and an outlet:
        a rotatable valve body rotatably disposed about the base:
        a bolus chamber formed within the rotatable valve body, wherein the bolus chamber comprises an inlet and an outlet:
        a moveable and rotatable piston at least partially disposed within the bolus chamber and in mechanical communication with the rotatable valve body, wherein the moveable and rotatable piston comprises a first position and a second position;

a spring disposed about the moveable and rotatable piston, wherein the spring biases the moveable and rotatable piston in the first position;

an inlet seal disposed about the base to form a fill pocket about the inlet of the bolus chamber;

an outlet seal disposed about the base to form a dose pocket about the outlet of the bolus chamber; and a vent disposed in the base, wherein as the moveable and rotatable piston moves between the first position and the second position, the inlet and/or outlet of the bolus chamber is located between the fill pocket and the dose pocket such that medicament released into a void between the rotatable valve body and the base is vented via the vent to a location outside of the combined piston pump and rotatable valve and away from a patient.

13. The device of claim 12, wherein the rotatable valve body comprises a cam configured to rotate and move the movable and rotatable piston from the first position to the second position.

14. The device of claim 13, wherein the base comprises a channel having a lip configured to maintain the movable and rotatable piston in the second position.

15. The device of claim 12, further comprising an actuator in mechanical communication with the rotatable valve body.

16. The device of claim 12, further comprising a valve spring in mechanical communication with the rotatable valve body.

17. The device of claim 12, wherein the device is configured to deliver a bolus dose which has a volume variation that is within ±10% of a targeted bolus dose volume.

18. A method for administering a bolus dose, the method comprising:

providing the device of claim 12;

depressing an actuator to move the moveable and rotatable piston from the first position to the second position and thereby fill the bolus chamber with the bolus dose via the inlet of the bolus chamber; and then releasing the actuator to permit the spring to bias the moveable and rotatable piston back to the first position and allow the bolus dose to flow from the bolus chamber via the outlet to a cannula.

19. The method of claim 18, wherein the bolus dose has a volume variation that is within ±10% of a targeted bolus dose volume.

* * * * *